(12) United States Patent
Yeung et al.

(10) Patent No.: US 7,538,102 B2
(45) Date of Patent: *May 26, 2009

(54) COMPOUNDS FOR THE TREATMENT OF HEPATITIS C

(75) Inventors: Kap-Sun Yeung, Madison, CT (US); John A. Bender, Middletown, CT (US); Robert G. Gentles, Wallingford, CT (US); Zhong Yang, Middletown, CT (US); Min Ding, Glastonbury, CT (US); Yong Tu, Cheshire, CT (US); Piyasena Hewawasam, Middletown, CT (US); Ying Han, Cheshire, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/046,030

(22) Filed: Mar. 11, 2008

(65) Prior Publication Data

US 2008/0226592 A1    Sep. 18, 2008

Related U.S. Application Data

(60) Provisional application No. 60/989,522, filed on Nov. 21, 2007, provisional application No. 60/894,889, filed on Mar. 14, 2007.

(51) Int. Cl.
*A61P 31/00* (2006.01)
*A61K 31/55* (2006.01)
*C07D 223/14* (2006.01)

(52) U.S. Cl. .................. 514/214.01; 540/576
(58) Field of Classification Search ............ 514/214.01; 540/576
See application file for complete search history.

(56) References Cited

U.S. PATENT DOCUMENTS

| 7,153,848 | B2 | 12/2006 | Hudyma et al. | 514/214.01 |
|---|---|---|---|---|
| 7,348,425 | B2 | 3/2008 | Hudyma et al. | 540/576 |
| 2007/0060565 | A1 | 3/2007 | Meanwell et al. | 514/214.01 |
| 2007/0078122 | A1 | 4/2007 | Bergstrom et al. | 514/214.01 |
| 2007/0184024 | A1 | 8/2007 | Meanwell et al. | 424/85.2 |
| 2007/0185083 | A1 | 8/2007 | Bergstrom et al. | 514/214.01 |
| 2007/0270405 | A1 | 11/2007 | Bender et al. | 514/214.01 |
| 2007/0270406 | A1 | 11/2007 | Gentles et al. | 514/214.01 |
| 2007/0275930 | A1 | 11/2007 | Gentles et al. | 514/79 |
| 2007/0275947 | A1 | 11/2007 | Bergstrom | 514/211.15 |
| 2007/0287694 | A1 | 12/2007 | Yeung et al. | 514/210.21 |

FOREIGN PATENT DOCUMENTS

| WO | WO 2005/080399 | 9/2005 |
|---|---|---|
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 12/022,541, filed Jan. 30, 2008, Kap-Sun Yeung et al.
U.S. Appl. No. 12/039,239, filed Feb. 28, 2008, Robert G. Gentles et al.
U.S. Appl. No. 12/045,874, filed Mar. 11, 2008, Robert G. Gentles et al.
U.S. Appl. No. 12/045,766, filed Mar. 11, 2008, John A. Bender et al.
U.S. Appl. No. 12/041,072, filed Mar. 3, 2008, Kap-Sun Yeung et al.
U.S. Appl. No. 12/031,844, filed Feb. 15, 2008, Andrew Nickel et al.
U.S. Appl. No. 12/046,286, filed Mar. 11, 2008, Piyasena Hewawasam et al.
U.S. Appl. No. 11/942,285, filed Nov. 19, 2007, John A. Bender et al.
U.S. Appl. No. 11/971,362, filed Jan. 9, 2008, John A. Bender et al.

*Primary Examiner*—Brenda L Coleman
(74) *Attorney, Agent, or Firm*—James Epperson

(57) ABSTRACT

The invention encompasses compounds of Formula I, pharmaceutically acceptable salts thereof, compositions, and methods of using the compounds. The compounds have activity against hepatitis C virus (HCV) and are useful in treating those infected with HCV.

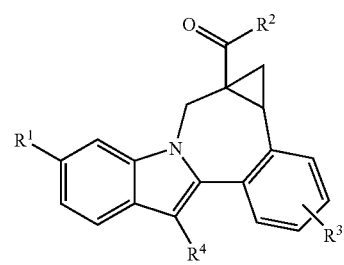

13 Claims, No Drawings

COMPOUNDS FOR THE TREATMENT OF HEPATITIS C

CROSS REFERENCE TO RELATED APPLICATIONS

This application claims the benefit of U.S. provisional application Ser. Nos. 60/894,889 filed Mar. 14, 2007 and 60/989,522 filed Nov. 21, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

The invention encompasses compounds of formula I, pharmaceutically acceptable salts thereof, compositions, and methods of treatment using these compounds.

One aspect of the invention is a compound of formula I

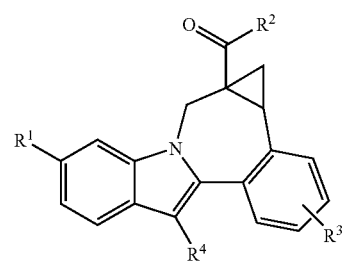

wherein:

$R^1$ is $CO_2R^5$ or $CONR^6R^7$;

$R^2$ is cycloalkoxy or bridged [2.1.1],[2.2.1],[2.2.2],[3.1.1], or [3.2.1] bicycloalkoxy, where the cycloalkyl or bridged bicycloalkyl moiety is substituted with 0-3 alkyl substituents;

or $R^2$ is $N(R^8)(R^9)$;

or $R^2$ is pyrrolidinyl, piperidinyl, piperazinyl, N-alkylpiperazinyl, N-(BOC)piperazinyl, N-benzylmethylpiperazinyl, homomorpholinyl, homopiperidinyl, morpholinyl, or thiomorpholinyl, and is substituted with 1 substituent selected from alkenyl, $R^{11}$, $(R^{11})$alkyl, $(R^{11}CO)$alkyl, pyrazinyl, pyrimidinyl, and phenyl where phenyl is substituted with 0-2 halo, alkyl , haloalkyl, cyano, hydroxy, alkoxy, haloalkoxy, $CONH_2$, $CONH(alkyl)$, or $CON(alkyl)_2$ substituents;

or $R^2$ is homopiperazinyl or diazepanone, and is substituted with 0-2 substituents selected from the group consisting of halo, hydroxy, alkyl, hydroxyalkyl, alkoxyalkyl, amino, alkylamino, dialkylamino, aminoalkyl, alkylaminoalkyl, dialkylaminoalkyl, pyrrolidinyl, piperidinyl, piperazinyl, N-(alkyl)piperazinyl, morpholinyl, thiomorpholinyl, pyridinyl, pyrazinyl, pyrimidinyl, pyrimidinyloxy, phenyl substituted with 0-2 halo, alkyl, or alkoxy substituents, benzyl, (pyridinyl)methyl, benzyloxycarbonyl, alkylcarbonyl, alkoxycarbonyl, $(R^{11})$alkyl, and $(R^{11}CO)$alkyl;

or $R^2$ is

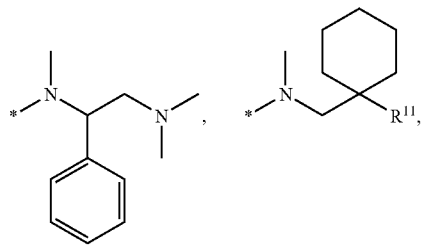

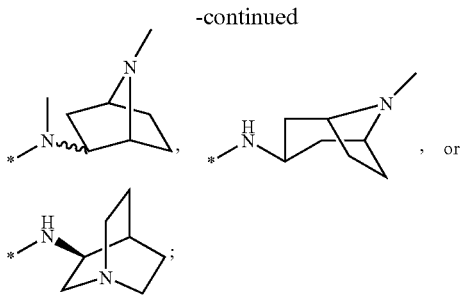

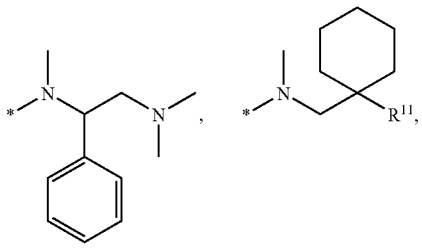

R³ is hydrogen, halo, alkyl, alkenyl, hydroxy, benzyloxy, or alkoxy;
R⁴ is $C_{5-7}$cycloalkyl;
R⁵ is hydrogen or alkyl;
R⁶ is hydrogen, alkyl, cycloalkyl, alkoxy, or $SO_2R^{10}$;
R⁷ is hydrogen, alkyl, or cycloalkyl;
or $NR^6R^7$ taken together is pyrrolidinyl, piperidinyl, piperazinyl, N-(alkyl)piperazinyl, homomorpholinyl, homopiperidinyl, morpholinyl, or thiomorpholinyl;
R⁸ is 4-piperidinyl, 4-(N-alkyl)piperidinyl, 3-(N-alkyl)pyrrolidinyl, ($R^{11}$)alkyl, ($R^{11}$CO)alkyl, (amino)cycloalkyl, (alkylamino)cycloalkyl, or (dialkylamino)cycloalkyl;
R⁹ is hydrogen, alkyl, cycloalkyl, hydroxyalkyl, alkoxyalkyl, aminoalkyl, alkylaminoalkyl, or dialkylaminoalkyl;
R¹⁰ is alkyl, haloalkyl, cycloalkyl, phenyl, amino, alkylamino, dialkylamino, benzylamino, or (benzyl)(alkyl)amino;
or R¹⁰ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl; and
R¹¹ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl;
or a pharmaceutically acceptable salt thereof.

Another aspect of the invention is a compound of formula I where
R¹ is $CO_2R^5$ or $CONR^6R^7$;
R² is cycloalkoxy or bridged [2.1.1], [2.2.1], [2.2.2], [3.1.1], or [3.2.1] bicycloalkoxy, where the cycloalkyl or bridged bicycloalkyl moiety is substituted with 0-3 alkyl substituents;
or R² is $N(R^8)(R^9)$;
or R² is pyrrolidinyl, piperidinyl, piperazinyl, homomorpholinyl, homopiperidinyl, morpholinyl, or thiomorpholinyl, and is substituted with 1 substituent selected from $R^{11}$, ($R^{11}$)alkyl, ($R^{11}$CO)alkyl, pyrazinyl, pyrimidinyl, pyrimidinyloxy, and phenyl where phenyl is substituted with 0-2 halo, alkyl or alkoxy substituents;
or R² is homopiperazinyl or diazepanone, and is substituted with 0-2 substituents selected from the group consisting of halo, hydroxy, alkyl, hydroxyalkyl, alkoxyalkyl, amino, alkylamino, dialkylamino, aminoalkyl, alkylaminoalkyl, dialkylaminoalkyl, pyrrolidinyl, piperidinyl, piperazinyl, N-(alkyl)piperazinyl, morpholinyl, thiomorpholinyl, pyridinyl, pyrazinyl, pyrimidinyl, pyrimidinyloxy, phenyl substituted with 0-2 halo, alkyl, or alkoxy substituents, benzyl, (pyridinyl)methyl, benzyloxycarbonyl, alkylcarbonyl, alkoxycarbonyl, ($R^{11}$)alkyl, and ($R^{11}$CO)alkyl;

or R² is

R³ is hydrogen, halo, alkyl, alkenyl, hydroxy, benzyloxy, or alkoxy;
R⁴ is $C_{5-7}$cycloalkyl;
R⁵ is hydrogen or alkyl;
R⁶ is hydrogen, alkyl, cycloalkyl, alkoxy, or $SO_2R^{10}$;
R⁷ is hydrogen, alkyl, or cycloalkyl;
or $NR^6R^7$ taken together is pyrrolidinyl, piperidinyl, piperazinyl, N-(alkyl)piperazinyl, homomorpholinyl, homopiperidinyl, morpholinyl, or thiomorpholinyl;
R⁸ is 4-piperidinyl, 4-(N-alkyl)piperidinyl, ($R^{11}$)alkyl, ($R^{11}$CO)alkyl, (amino)cycloalkyl, (alkylamino)cycloalkyl, or (dialkylamino)cycloalkyl;
R⁹ is hydrogen, alkyl, cycloalkyl, hydroxyalkyl, alkoxyalkyl, aminoalkyl, alkylaminoalkyl, or dialkylaminoalkyl;
R¹⁰ is alkyl, haloalkyl, cycloalkyl, phenyl, amino, alkylamino, dialkylamino, benzylamino, or (benzyl)(alkyl)amino;
or R¹⁰ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl; and
R¹¹ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl;
or a pharmaceutically acceptable salt thereof.

Another aspect of the invention is a compound of formula I where R¹ is carboxy.

Another aspect of the invention is a compound of formula I where R¹ is $CONR^6R^7$, R⁶ is $SO_2R^{10}$, and R⁷ is hydrogen.

Another aspect of the invention is a compound of formula I where R² is $NR^8R^9$.

Another aspect of the invention is a compound of formula I where R² is pyrrolidinyl, piperidinyl, piperazinyl, N-alkylpiperazinyl, N-(BOC)piperazinyl, N-benzylmethylpiperazinyl, homomorpholinyl, homopiperidinyl, morpholinyl, or thiomorpholinyl, and is substituted with 1 substituent selected from alkenyl, $R^{11}$, ($R^{11}$)alkyl, ($R^{11}$CO)alkyl, pyrazinyl, pyrimidinyl, and phenyl where phenyl is substituted with 0-2 halo, alkyl or alkoxy substituents.

Another aspect of the invention is a compound of formula I where R³ is hydrogen.

Another aspect of the invention is a compound of formula I where R³ is halo, alkyl, or alkoxy.

Another aspect of the invention is a compound of formula I where R⁴ is cyclohexyl.

Another aspect of the invention is a compound of formula I where $R^{10}$ is dialkylamino.

Another aspect of the invention is a compound of formula I where $R^{10}$ is pyrrolidinyl, piperidinyl, piperazinyl, homomorpholinyl, homopiperidinyl, morpholinyl, or thiomorpholinyl, and is substituted with 0-2 substituents selected from halo and alkyl.

Any scope of any variable, including $R^1$, $R^2$, $R^3$, $R^4$, $R^5$, $R^6$, $R^7$, $R^8$, $R^9$, $R^{10}$, and $R^{11}$, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

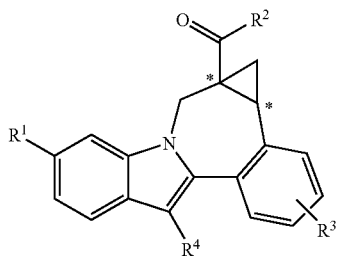

Synthetic Methods

Formula I compounds may be made by methods known in the art including those described below. Some reagents and intermediates are known in the art. Other reagents and intermediates can be made by methods known in the art using readily available materials. The variables used to describe the synthesis of formula I compounds are intended only to illustrate how to make and are not to be confused with variables used in the claims or in other sections of the specification.

Abbreviations used within the schemes generally follow conventions used in the art. Some examples are as follows: THF means tetrahydrofuran; DMF means N,N-dimethylformamide; RCM means ring-closing methasis; Boc means tert-butoxycarbonyl; TFA means trifluoracetic acid; DMA means N,N-dimethylacetamide; $PPh_3$ means triphenylphosphine; OAc means acetate; Me means methyl; COD (or cod) means 1,5-cyclooctadiene; dtbpy means 4,4'-di-tert-butyl-2,2'-bipyridine; dba means dibenzylideneacetone; Xantphos means 4,5-bis(diphenylphosphino)-9,9-dimethylxanthine; aq means aqueous; EtOH means ethanol; MeOH means methanol; TBTU means 2-(1H-benzotriazole-1-yl)-1,1,3,3-tetramethyluronium tetrafluroborate; DMSO means dimethylsulfoxide; HATU means O-(7-azabenzotriazol-1-yl)-N,N,N',N'-tetramethyluronium hexafluorophosphate; EEDQ means 2-ethoxy-1-ethoxycarbonyl-1,2-dihydroquinoline; WSC means 1-[3-(dimethylamino)propyl]-3-ethylcarbodiimide hydrochloride; DMAP means 4-dimethylaminopyridine; n-Bu means n-butyl; BEMP means 2-tert-butylimino-2-diethylamino-1,3-dimethylperhydro-1,3,2-diazaphosphorine, polymer-bound; DIPEA means diisopropylethylamine; and TEA means triethylamine.

Some diester intermediates useful for the synthesis of formula I compounds may be prepared by using the general methodology depicted in Scheme 1.

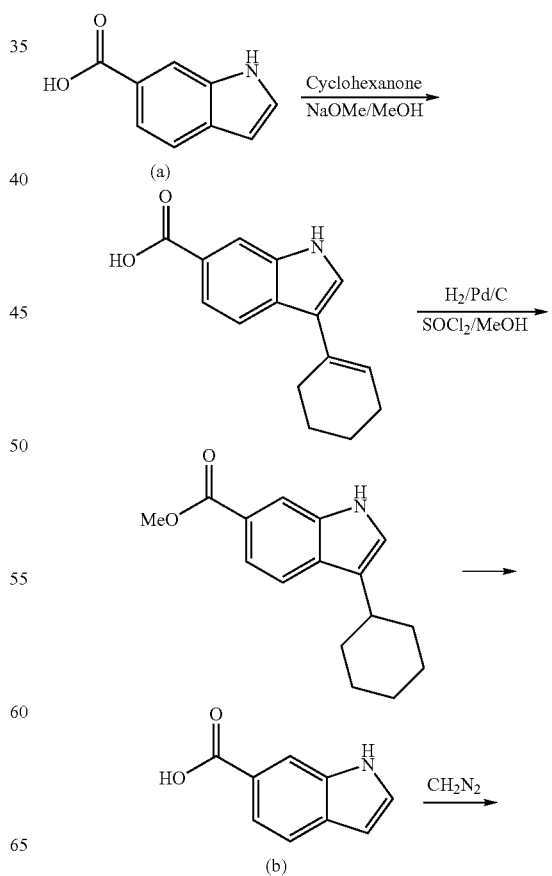

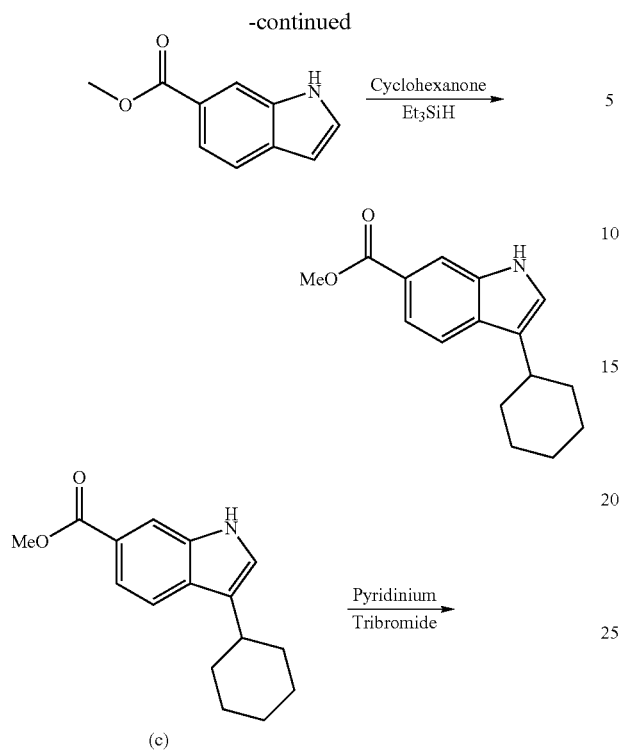

Condensation of 1H-indole-6-carboxylic acid with cyclohexanone can generate 3-cyclohexenyl-1H-indole-6-carboxylic acid. This indole ester can be subjected to sequential reduction and esterification to provide methyl 3-cyclohexanyl-1H-indole-6-carboxylate.

Alternatively, methyl 3-cyclohexanyl-1H-indole-6-carboxylate can be prepared in a two step procedure that involves an initial esterification of 1H-indole-6-carboxylic acid, for example using diazomethane in ether, followed by sequential condensation with cyclohexanone, followed by reduction.

Treatment of the resultant indole ester with pryridinium tribromide in a mixture of THF and chloroform can generate methyl 2-bromo-3-cyclohexanyl-1H-indole-6-carboxylate. This intermediate can be used in a variety of couplings, for example with 2-formyl-phenyl boronic acids using appropriate palladium catalysts, to generate the aromatic aldehyde intermediates shown. NMR analysis of this class of compound indicated that the aryl aldehydes are sometimes observed to exist in equilibrium with the related ring-closed hemiaminals, as shown below.

These intermediates can then be transformed into indolobenzazepine diester intermediates, for example by treating with methyl 2-(dimethoxyphosphoryl)acrylate under the influence of cesium carbonate in DMF via consecutive Michael and Horner Emmons reactions.

The resultant diester intermediates may be converted to cyclopropyl derivatives, for example as shown in Scheme 2.

Scheme 2.

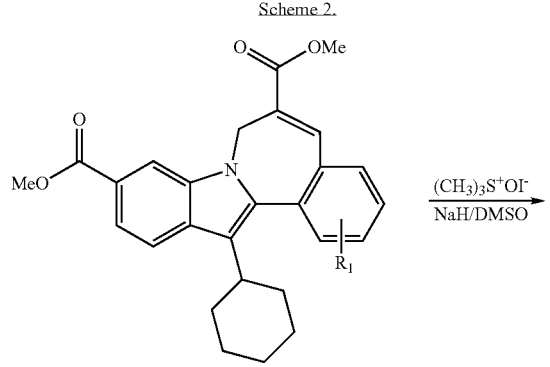

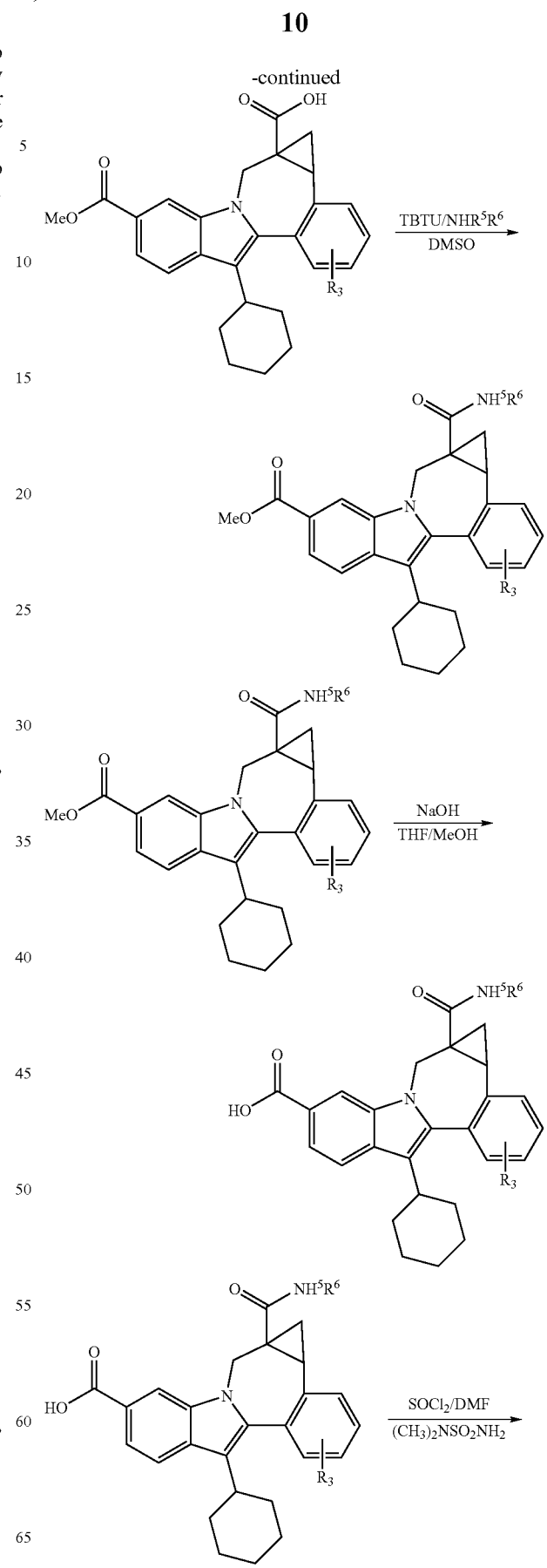

-continued

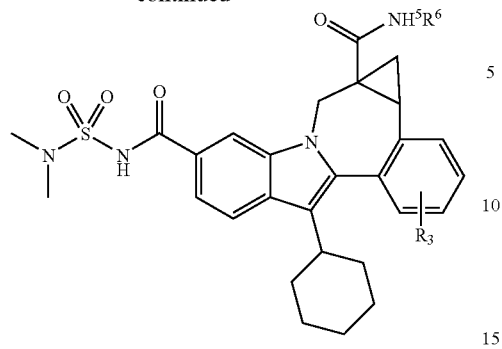

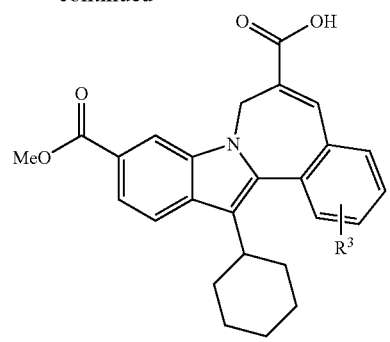

Fused cyclopropyl diester derivatives can be generated by methods known in the art including treatment of the indolobenzazepine diester intermeidates with trimethyl sulfoxonium iodide under strongly basic conditions in DMSO. The aliphatic ester moiety in these compounds can be selectively hydrolyzed using tetra-n-butylammonium hydroxide in methanol, and the resultant mono-acids can subsequently be condensed with a wide selection of primary and secondary amines to provide carboxamides depicted in the above scheme. These intermediates may be subjected to an additional hydrolysis reaction that provides the 8-cyclohexyl-cycloprop[d]indolo[2,1-a][2]benzazepine-5-carboxylic acid. Additionally, these compounds can serve as intermediates in additional coupling reactions with appropriate sulfonyl ureas that can generate acyl sulfonyl urea compounds.

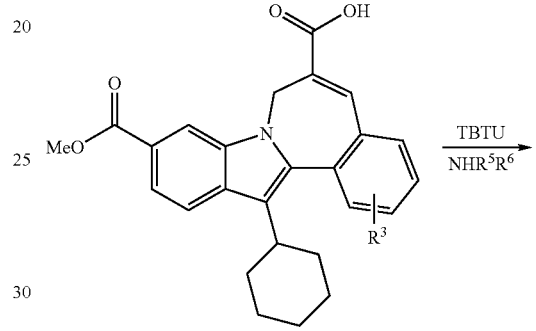

In an alternative procedure, indolo [2,1-a] [2]benzazepine-10-carboxylate intermediates may first be subjected to a base catalysed selective hydrolysis reaction that results in the generation of the mixed acid-ester class of compound (see Scheme 3). Subsequent coupling with amines can generate carboxamides. These intermediates can be cyclopropanated, for example by treatment with trimethylsulfoxonium iodide under basic conditions, to generate the cyclopropyl ring-fused derivatives. Subsequent hydrolysis of the remaining ester moiety can generate carboxylic acid compounds of formula I. These compounds may be converted to their corresponding acyl sulfonyl ureas derivatives.

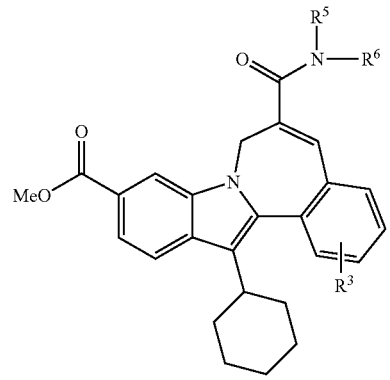

Scheme 3.

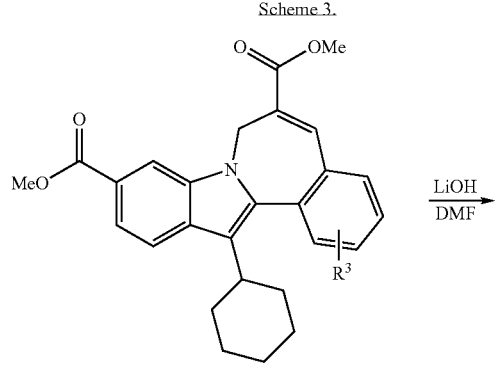

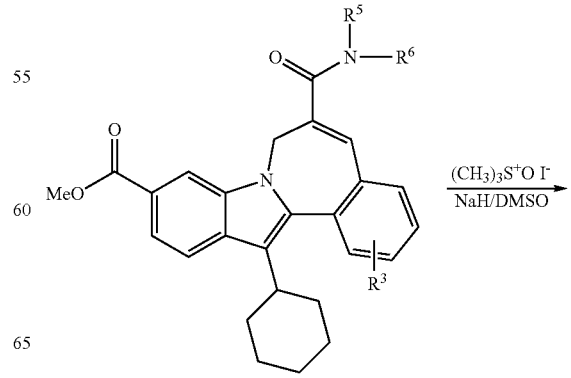

-continued
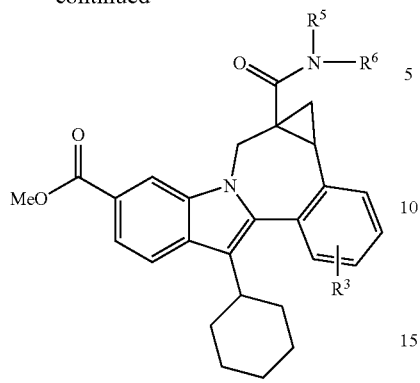
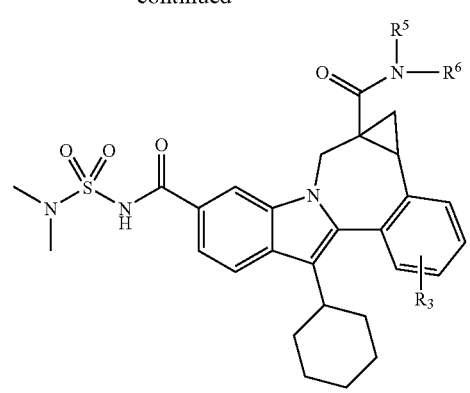
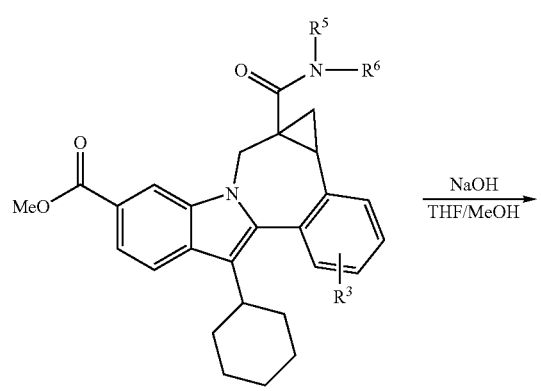
Additional methodology that can be used to make further examples is shown in scheme 4.
Scheme 4.
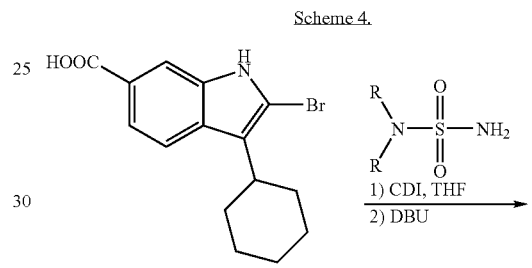
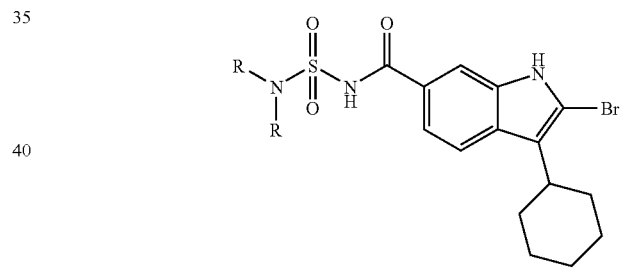
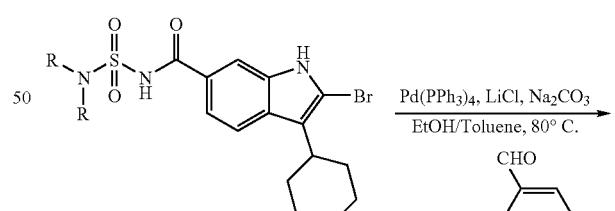
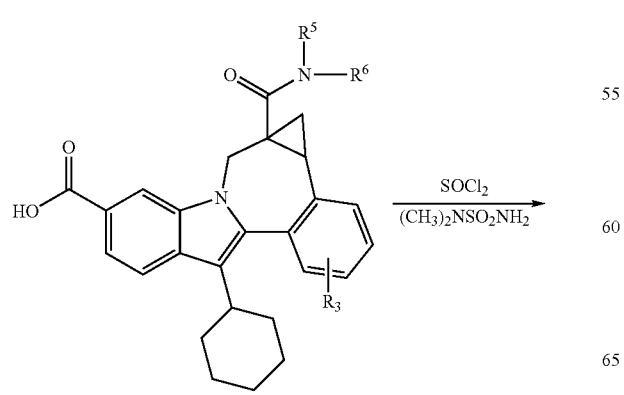
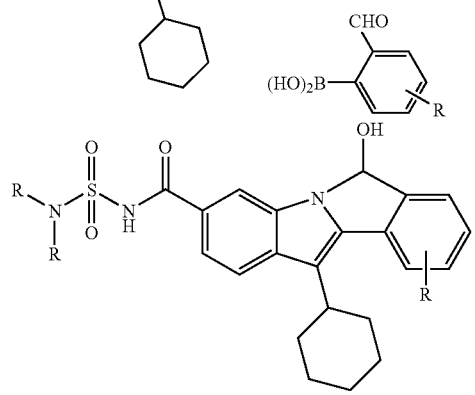

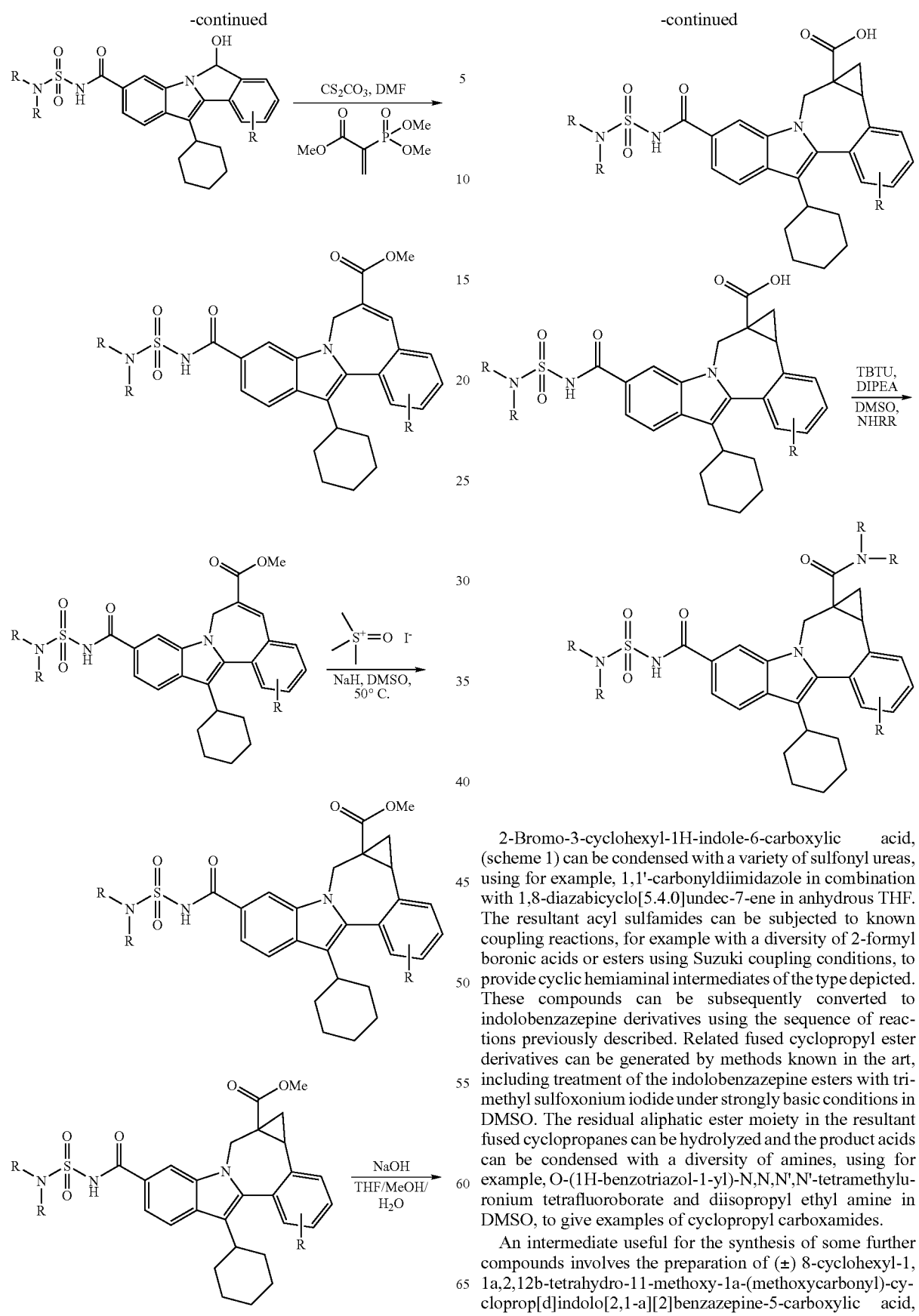

2-Bromo-3-cyclohexyl-1H-indole-6-carboxylic acid, (scheme 1) can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions, for example with a diversity of 2-formyl boronic acids or esters using Suzuki coupling conditions, to provide cyclic hemiaminal intermediates of the type depicted. These compounds can be subsequently converted to indolobenzazepine derivatives using the sequence of reactions previously described. Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed and the product acids can be condensed with a diversity of amines, using for example, O-(1H-benzotriazol-1-yl)-N,N,N',N'-tetramethyluronium tetrafluoroborate and diisopropyl ethyl amine in DMSO, to give examples of cyclopropyl carboxamides.

An intermediate useful for the synthesis of some further compounds involves the preparation of (±) 8-cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester, as shown in Scheme 5.

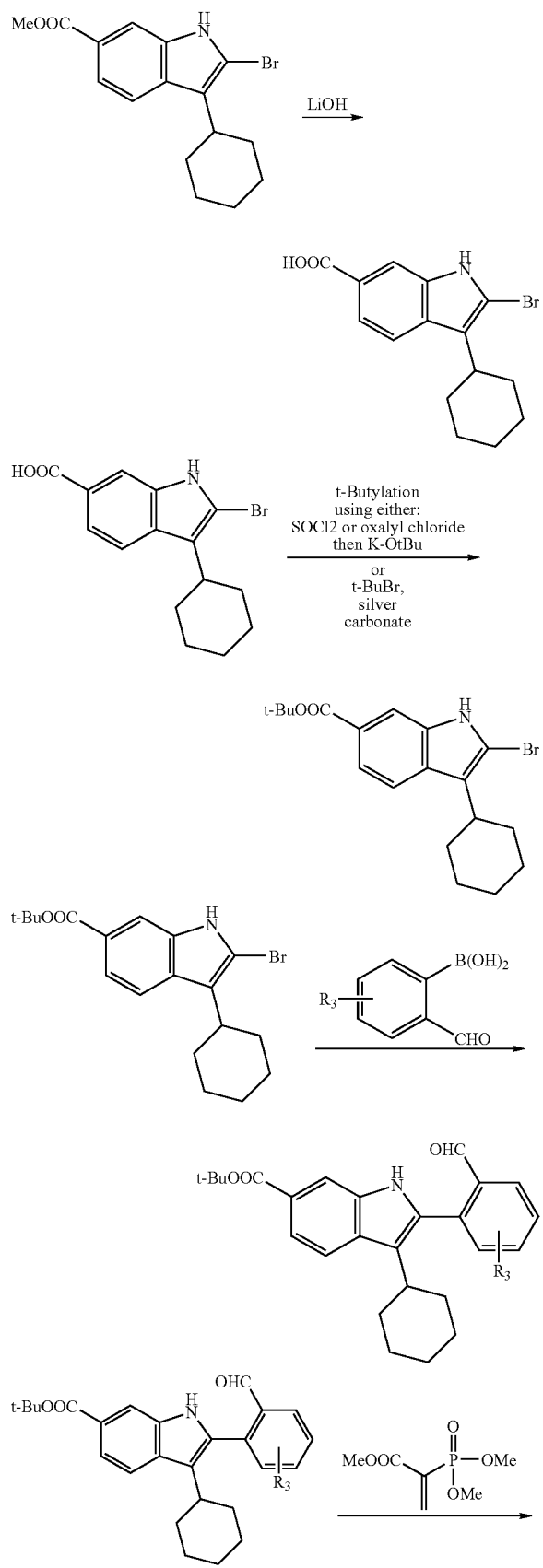
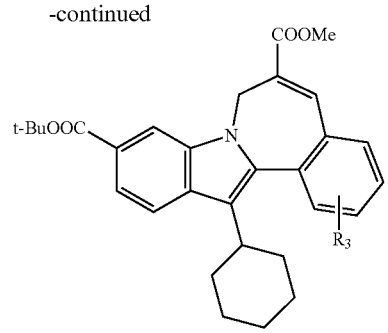

This methodology involves base catalyzed hydrolysis of the indole methyl ester shown, followed by its reaction with either thionyl chloride and potassium tertiary butoxide, or by alkylation with silver carbonate and tertiary butyl bromide. The resultant compound can be transformed using chemistry analogous to that outlined previously to provide the mixed ester indolobenzazepines shown in scheme 5.

The resultant (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester can be useful in an alternative procedure that can be employed for the preparation of acylsulfamide and acylsulfonamide compounds as shown in scheme 6.

Scheme 6.

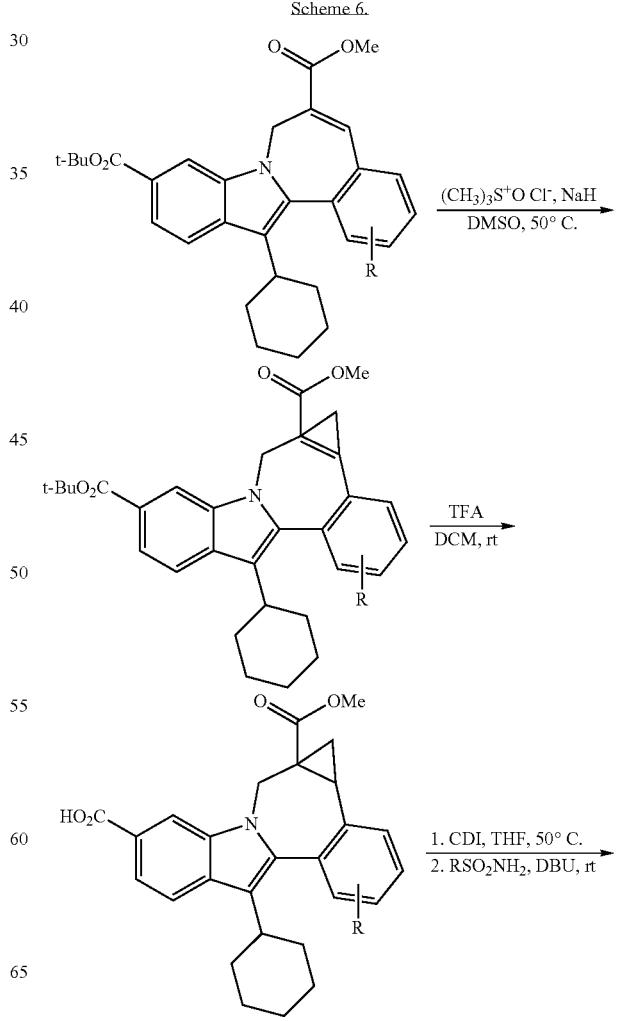

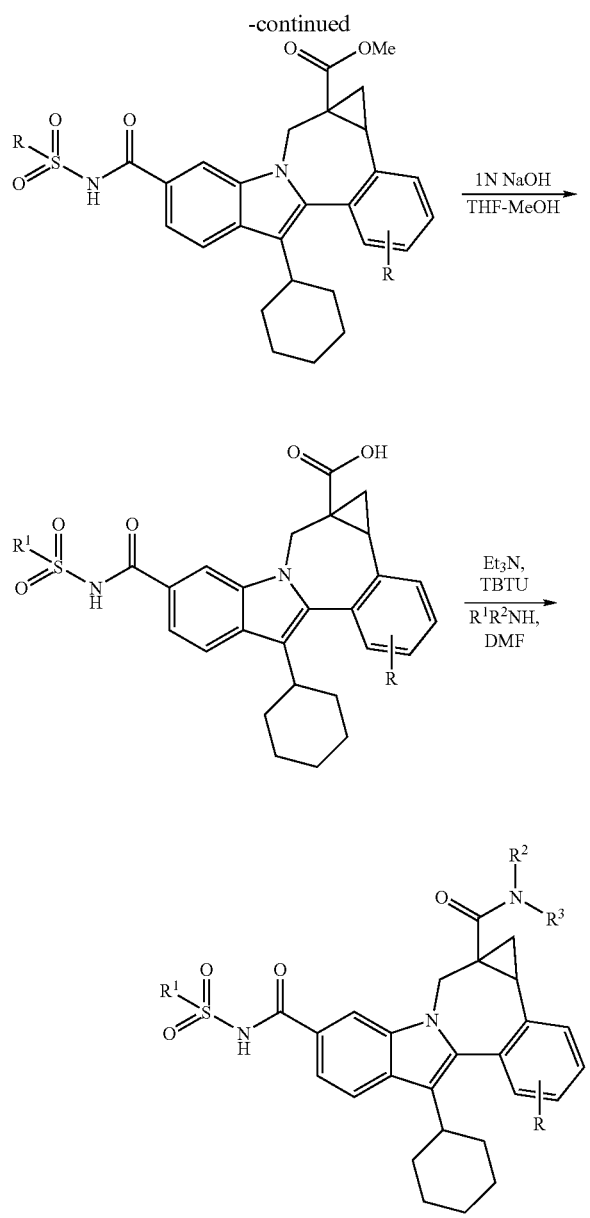

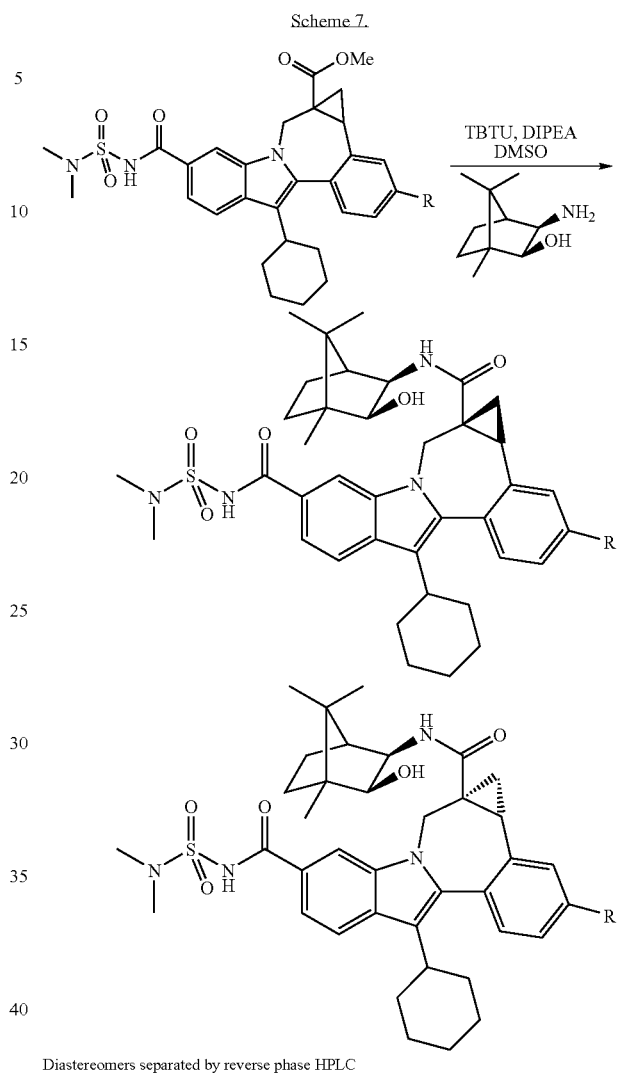

Cyclopropanation of an intermediate t-butyl ester indolobenzazepine and subsequent cleavage of the t-butyl ester group can generate the related indole acid which can be coupled to a diversity of sulfonamides and sulfonylureas. Subsequent hydrolysis of the residual ester moiety affords the related bridged acids, which can be coupled with a diversity of amines, using for example, O-(1H-benzotriazol-1-yl)-N, N,N',N'-tetramethyluronium tetrafluoroborate and diisopropyl ethyl amine in DMSO, to provide further carboxamides examples.

Some of the compounds discussed exist as mixtures of stereoisomers. The invention encompasses all stereoisomers of the compounds. Methods of isolating and separating stereoisomeric mixtures are well known in the art. One method is shown below and involves the syntheses of diastereomeric amides as shown in Scheme 7. Diastereomeric esters can also be prepared.

Diastereomers separated by reverse phase HPLC

Some diastereomeric amides can be separated using reverse phase HPLC to provide optically active carboxamides. Subsequently, these compounds can be hydrolyzed and the resultant optically active acids can be coupled to a diversity of amines, using for example, O-(1H-benzotriazol-1-yl)-N,N,N',N'-tetramethyluronium tetrafluoroborate and diisopropyl ethyl amine in DMSO, to provide further examples of optically active examples, as shown in scheme 8.

Scheme 8.

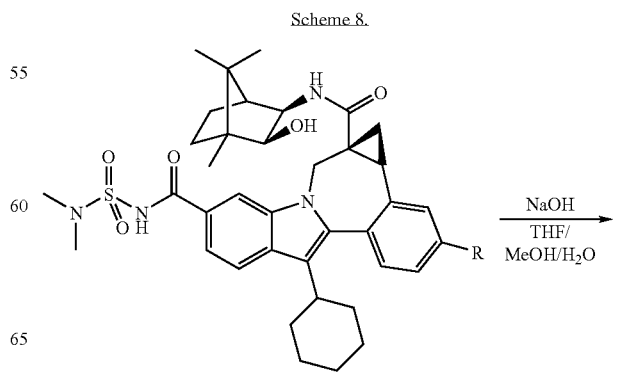

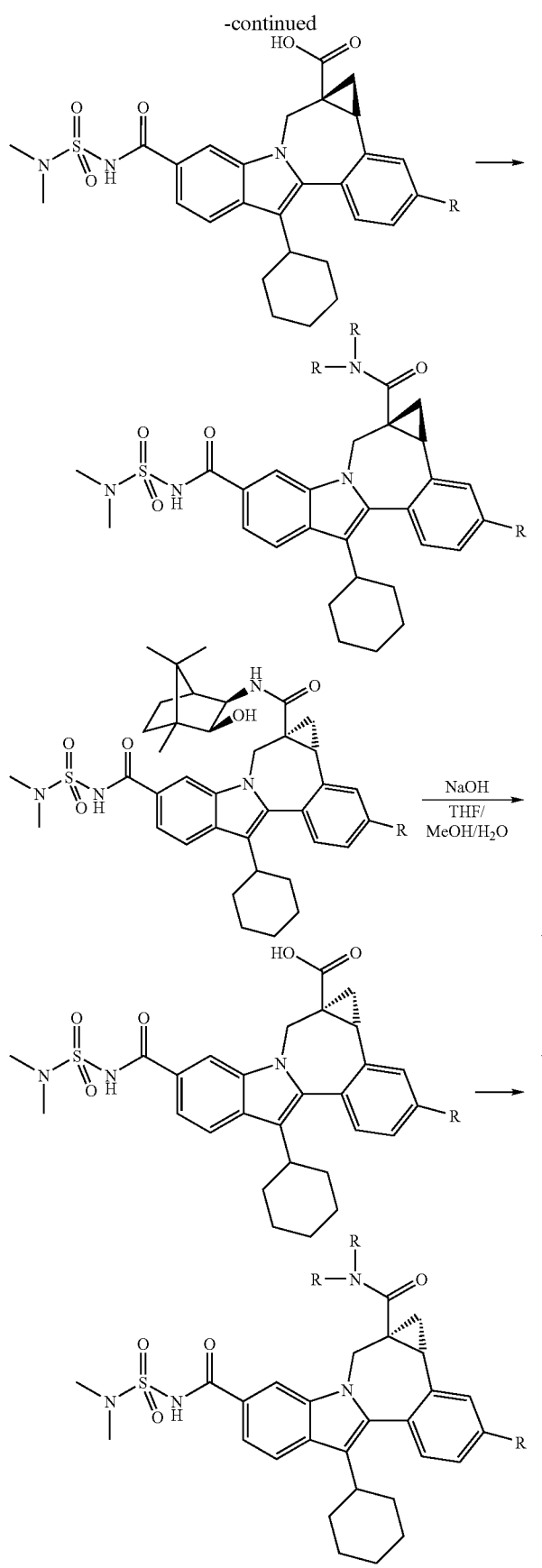

Other standard acid amine coupling methods can also be used to give optically active carboxamides.

Variation in the functionality of the aryl moiety of the fused benzazepine heterocycle compounds can be achieved as shown in scheme 1, for example by using a variety of boronic acids as coupling partners with indole bromide intermediates. Alternatively, a suitably protected reactive functionality in the aryl moiety of these intermediates can be deprotected, and can then be subsequently derivatized using methods known in the art, some examples of which are depicted in scheme 9.

Scheme 9.

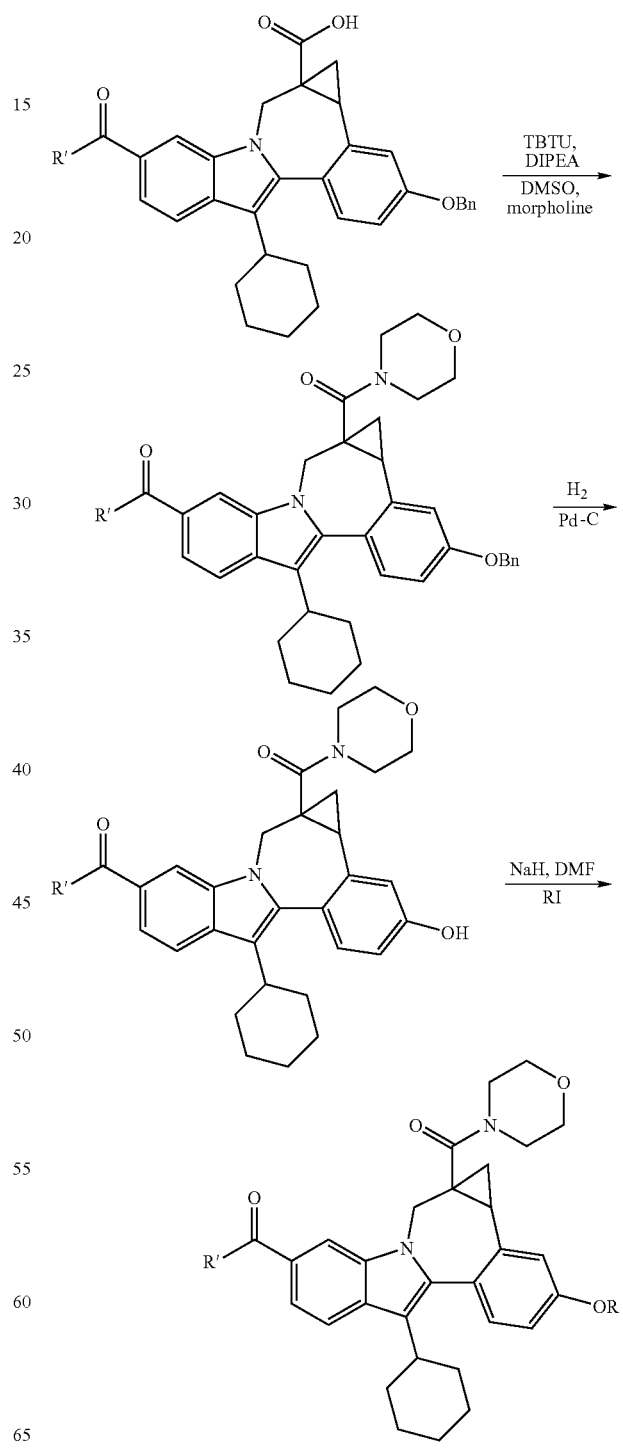

R = ethyl, isopropyl, R' = OMe, NHSO$_2$NMe$_2$

In an additional variation, the intermediate phenols depicted in the above scheme can be converted to triflate derivatives that can be used to prepare further aryl functionalized examples using a diversity of coupling reactions, some of which are outlined in scheme 10.
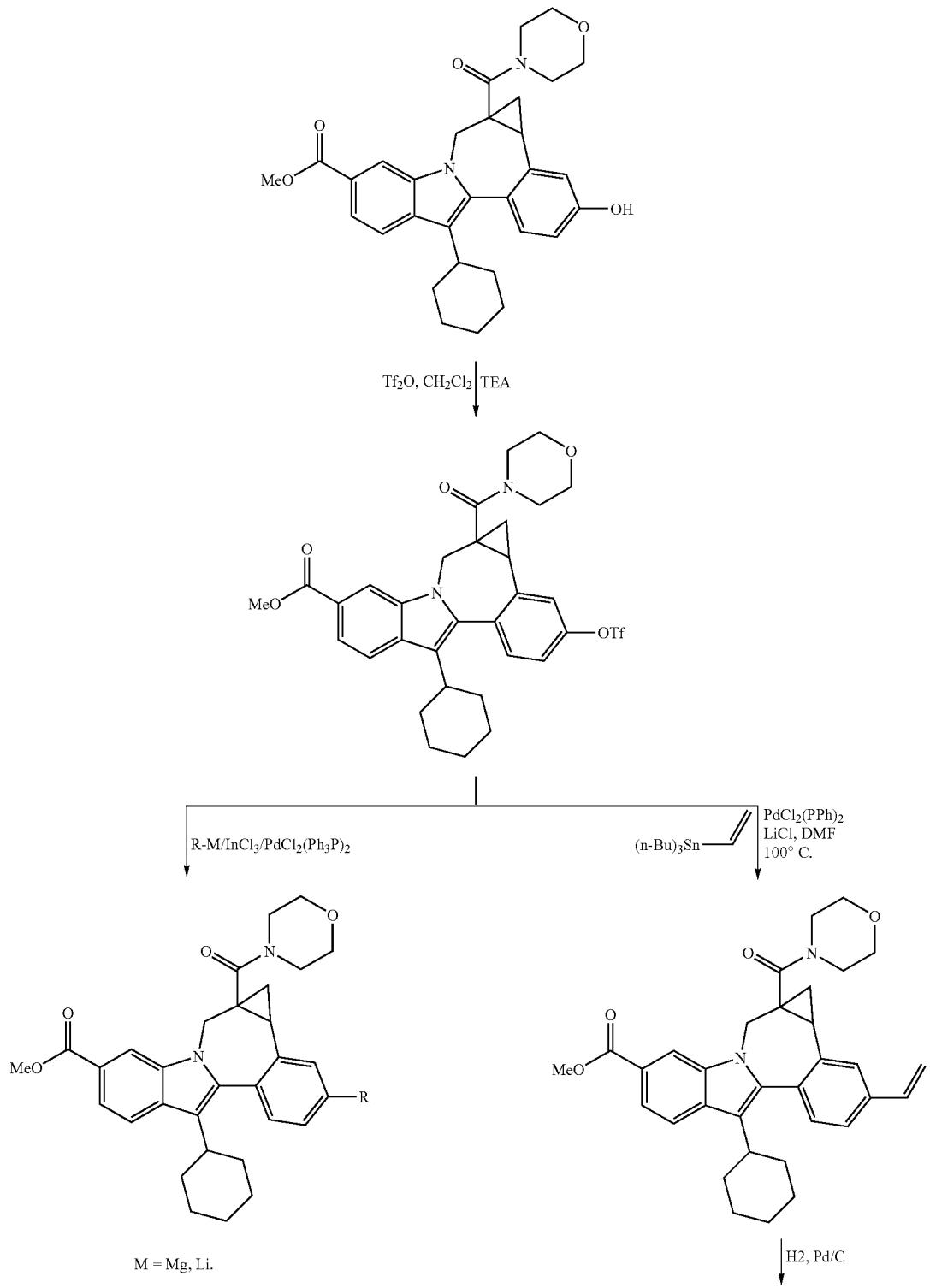

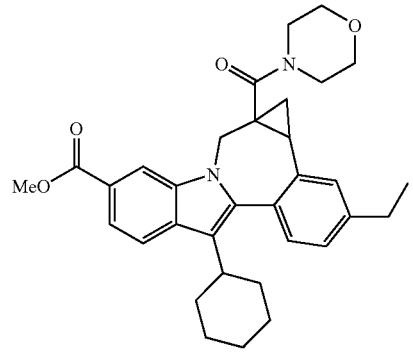

In the case of the examples shown in Scheme 10, the product esters can be hydrolyzed and subsequently coupled with a diversity of sulfonyl ureas to furnish further acyl sulfamide examples, as described previously.

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using two sequential chromatography steps: Heparin sepharose CL-6B and polyU sepharose 4B (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Corning 3600). The assay buffer is composed of 20 mM Hepes, pH 7.5, 2.5 mM KCl, 2.5 mM MgCl2, 1 mM DTT, 1.6 U RNAse inhibitor (Promega N2515), 0.01 mg/ml BSA (Sigma B6917), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/pl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (1.75 nM) was added to diluted compound followed by the addition of a mixture of template (0.36 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^{\wedge}D)))$.

FRET Assay Preparation. The HCV FRET screening assay was performed in 96-well cell culture plates. The FRET peptide (Anaspec, Inc.) (Taliani et al., *Anal. Biochem*. 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 µM final from a 2 mM stock.

To prepare plates, HCV replicon cells, with or without a Renilla luciferase reporter gene, were trypsinized and plated in a 96-well plate with titrated test compounds added in columns 3 through 12; columns 1 and 2 contained a control compound (HCV control inhibitor), and the bottom row contained cells with DMSO only. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added to measure cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for up to 20 cycles and the plate read in a kinetic mode. Typically, the signal to noise using an endpoint analysis after the reads was at least three-fold. Alternatively, after Alamar blue reading, plates were rinsed with PBS, then used for luciferase assay using the Promega Dual-Glo Luciferase Assay System or the Promega EnduRen Live Cell Substrate assay.

Compound analysis was performed by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV control inhibitor at the end of the assay period. These numbers were similar to those obtained from naive Huh-7 cells. The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values were calculated as the concentration which caused a 50% reduction in FRET or luciferase activity. The two numbers generated for the compound plate, percent cytoxicity and percent activity, were used to determine compounds of interest for further analysis.

Representative data for compounds are reported in Table 1.

TABLE 1

| Structure | $IC_{50}$ | $EC_{50}$ |
|---|---|---|
| | B | B |
| | B | B |

TABLE 1-continued
| Structure | IC$_{50}$ | EC$_{50}$ |
|---|---|---|
| 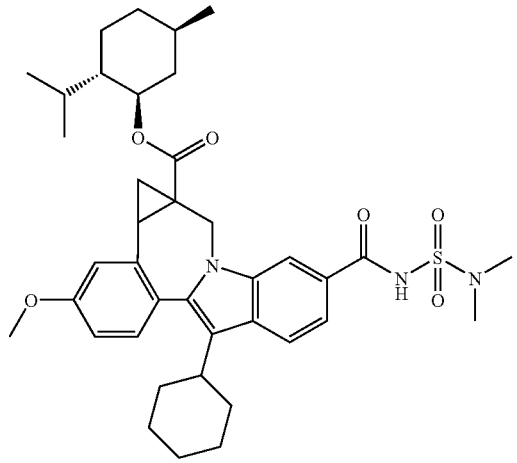 | B | A |
| 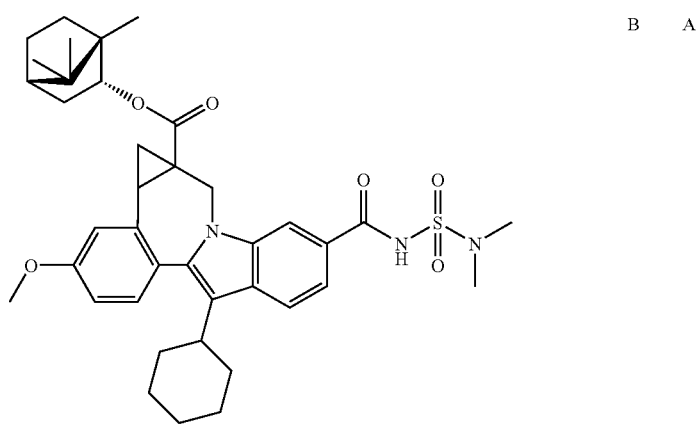 | B | A |
| 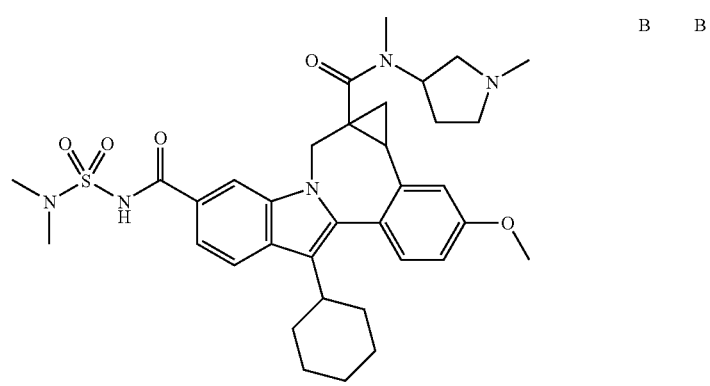 | B | B |

TABLE 1-continued
| Structure | IC$_{50}$ | EC$_{50}$ |
|---|---|---|
| 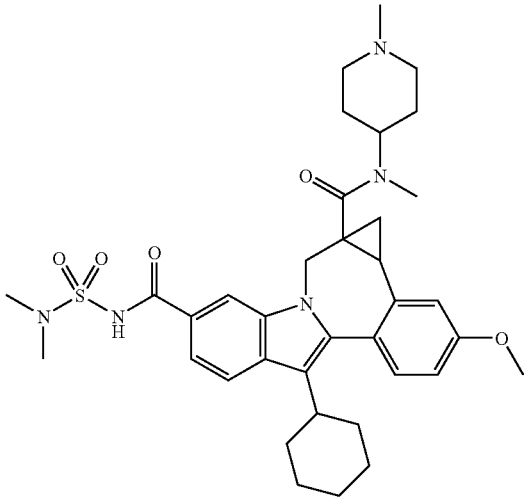 | B | B |
| 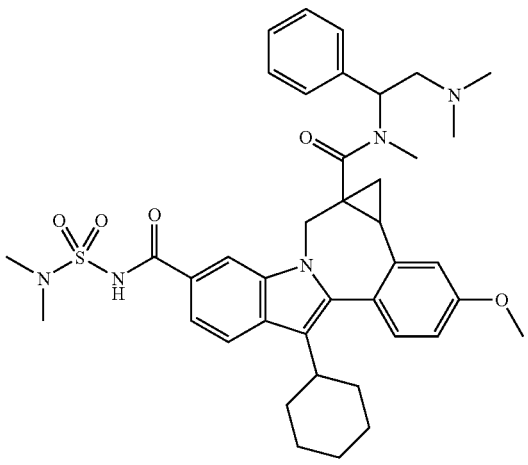 | B | B |
| 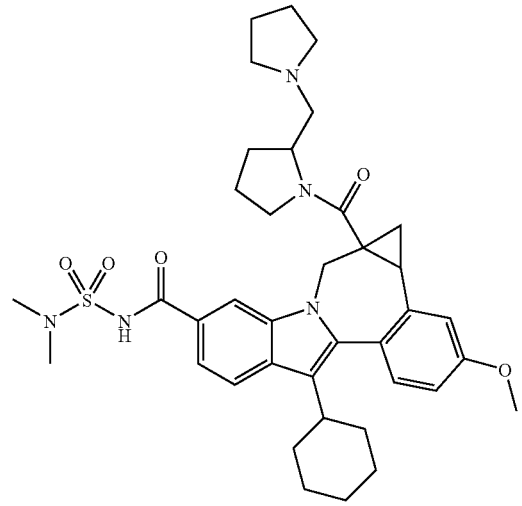 | B | B |

TABLE 1-continued
| Structure | IC$_{50}$ | EC$_{50}$ |
|---|---|---|
| 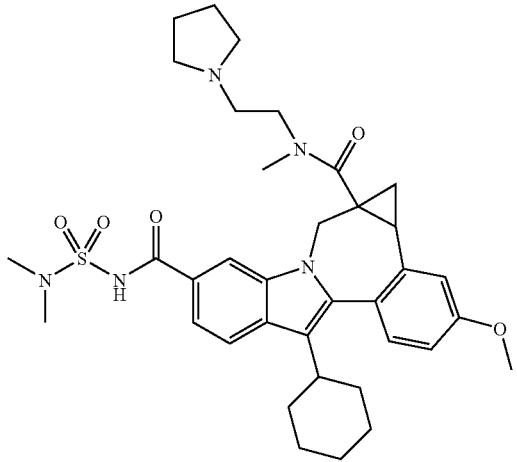 | B | B |
| 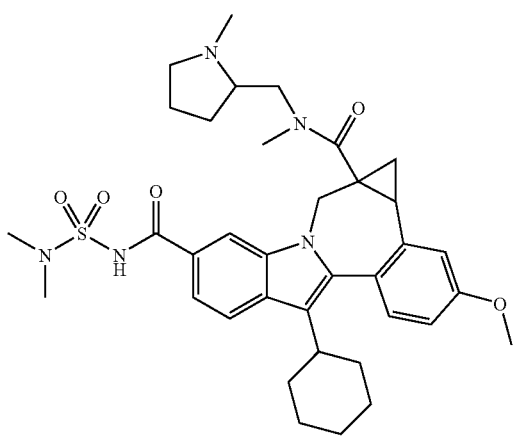 | B | B |
| 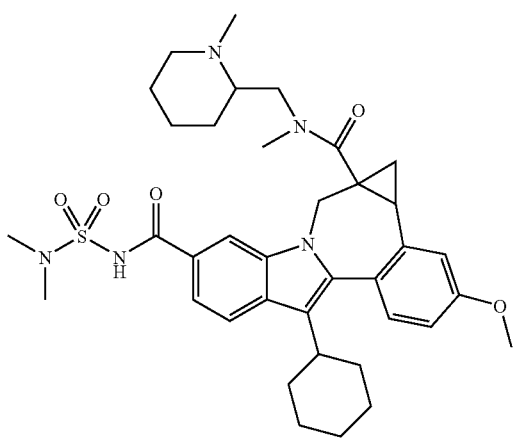 | B | B |

TABLE 1-continued
| Structure | IC$_{50}$ | EC$_{50}$ |
|---|---|---|
| 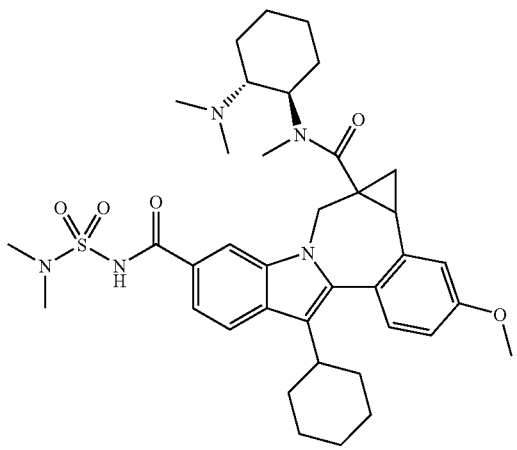 | B | B |
| 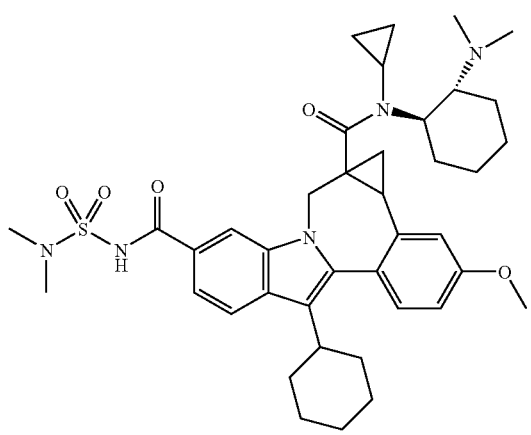 | B | B |
| 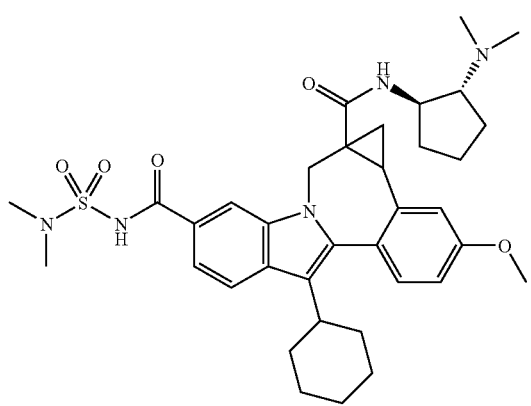 | B | B |

TABLE 1-continued

| Structure | IC$_{50}$ | EC$_{50}$ |
|---|---|---|
| | B | B |
| | B | B |
| | B | B |
| | B | B |

TABLE 1-continued
| Structure | IC$_{50}$ | EC$_{50}$ |
|---|---|---|
| 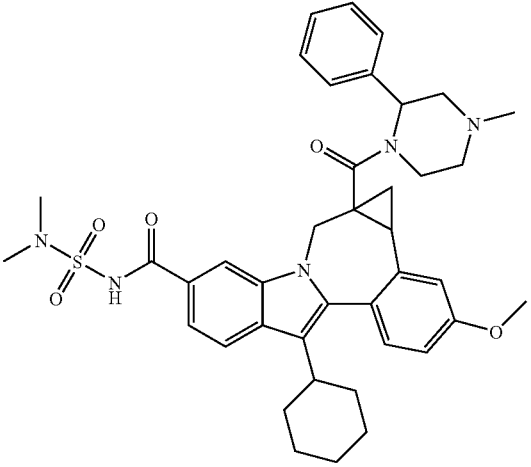 | B | B |
| 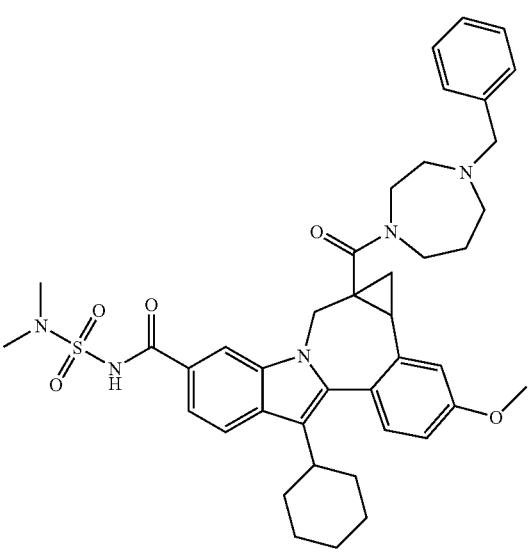 | B | B |
| 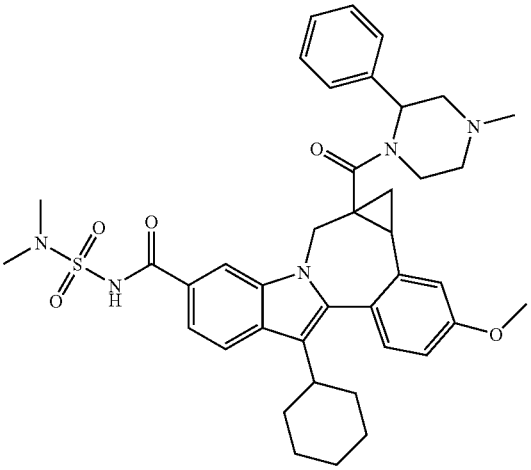 | B | B |

TABLE 1-continued
| Structure | IC$_{50}$ | EC$_{50}$ |
|---|---|---|
| 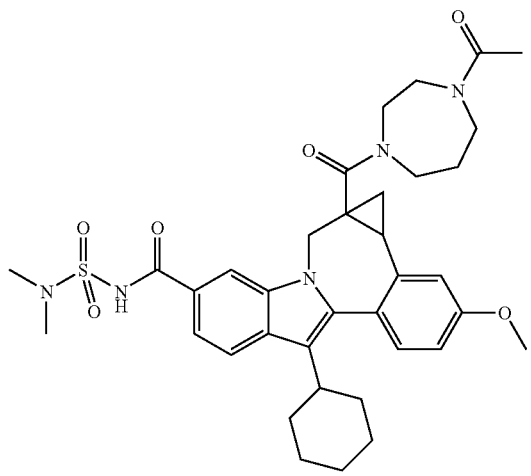 | B | B |
| 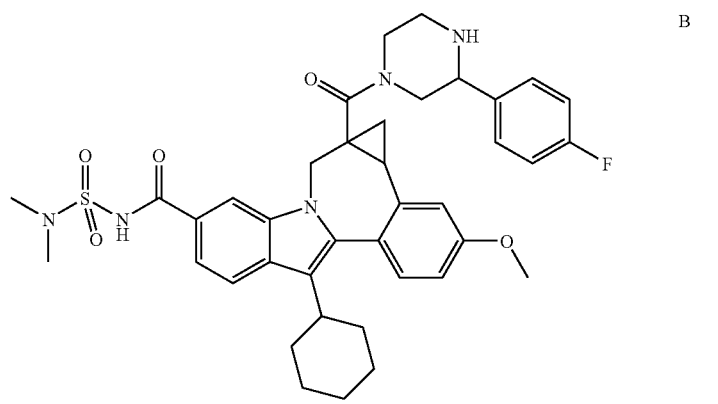 | B | B |
| 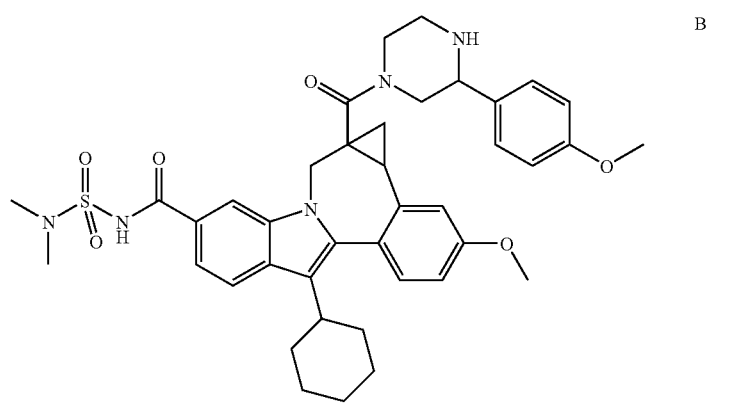 | B | B |

TABLE 1-continued

| Structure | IC$_{50}$ | EC$_{50}$ |
|---|---|---|
| | B | B |
| | B | B |
| | | |

TABLE 1-continued
| Structure | IC$_{50}$ | EC$_{50}$ |
|---|---|---|
| 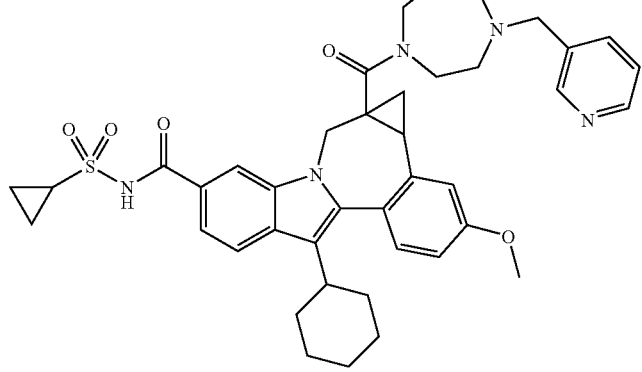 | B | B |
| 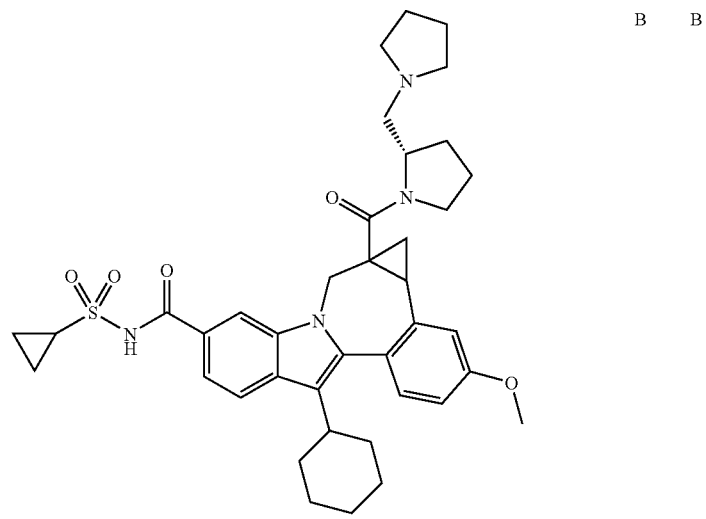 | B | B |
| 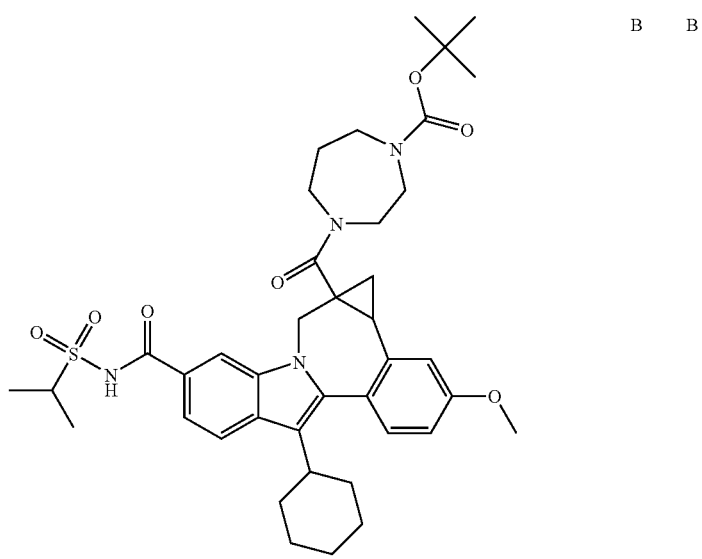 | B | B |

TABLE 1-continued
| Structure | IC$_{50}$ | EC$_{50}$ |
|---|---|---|
| 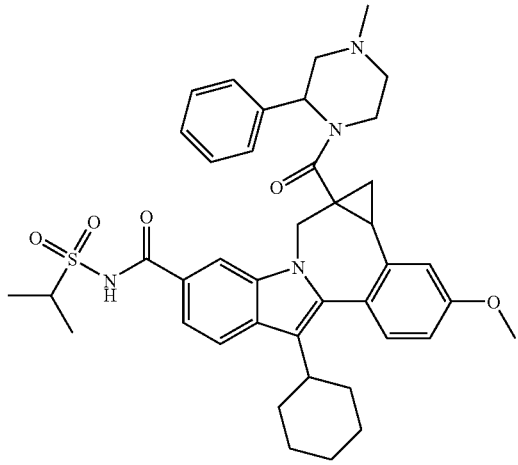 | B | B |
| 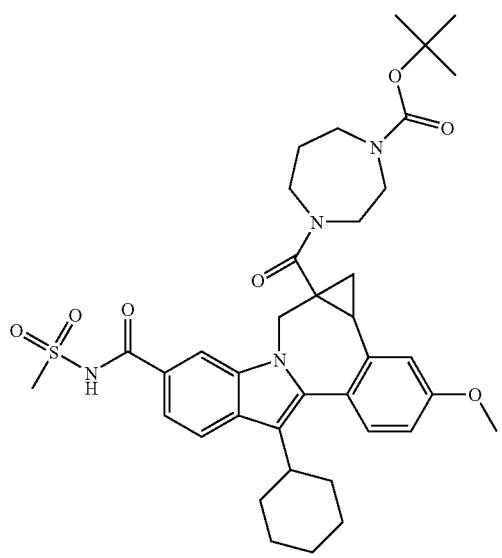 | B | B |
| 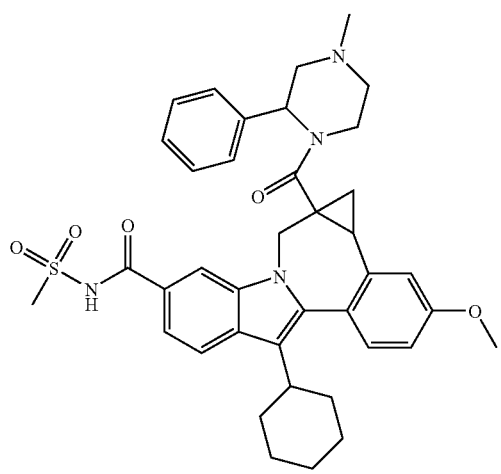 | B | B |

TABLE 1-continued
| Structure | IC$_{50}$ | EC$_{50}$ |
|---|---|---|
| | B | B |
| | B | B |
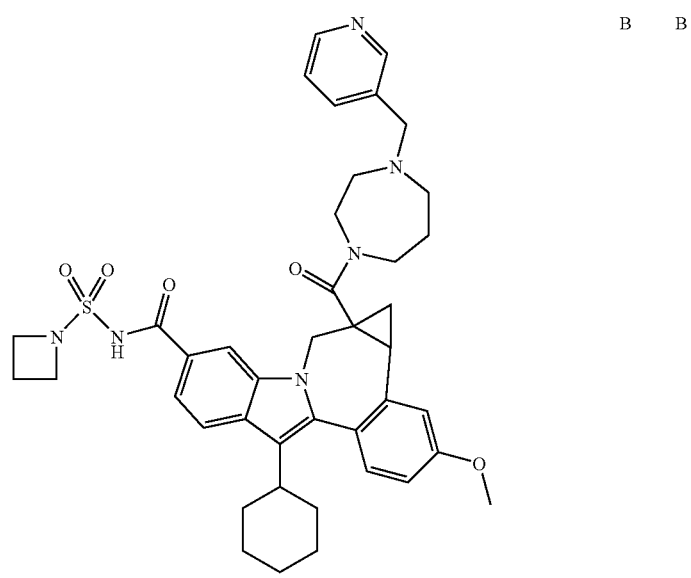

TABLE 1-continued
| Structure | IC$_{50}$ | EC$_{50}$ |
|---|---|---|
| 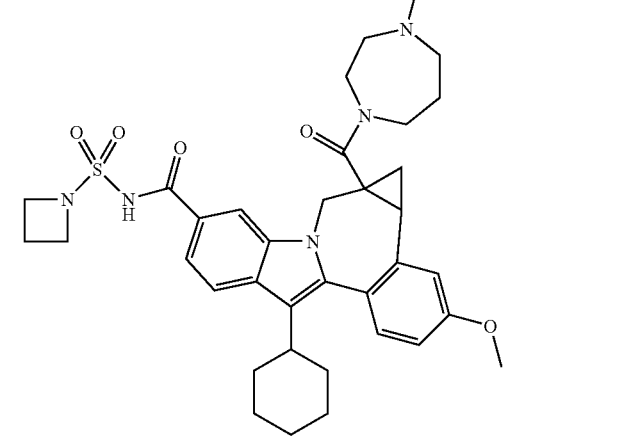 | B | B |
| 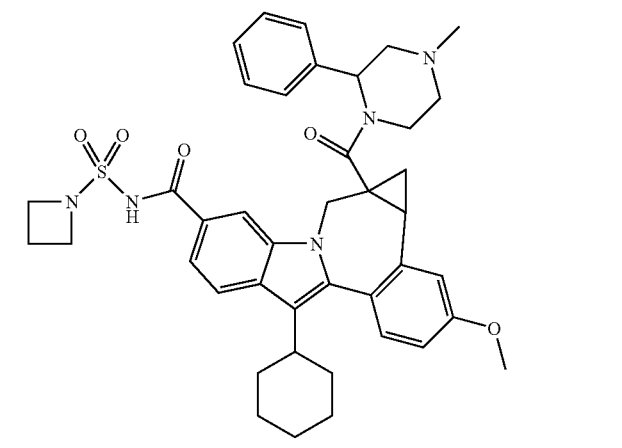 | B | B |
| 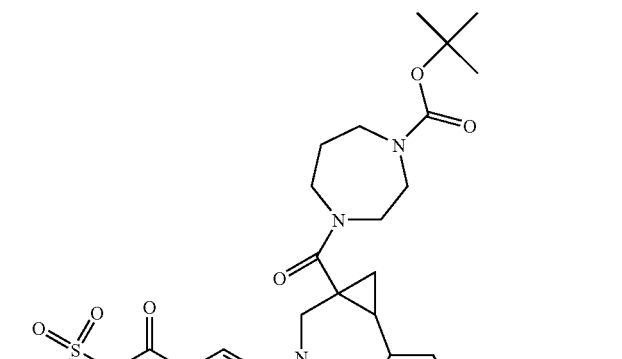 | B | |

TABLE 1-continued

| Structure | IC$_{50}$ | EC$_{50}$ |
|---|---|---|
| | | B |
| | | B |
| | | B |

TABLE 1-continued

| Structure | IC$_{50}$ | EC$_{50}$ |
| --- | --- | --- |
| | B | |
| | B | B |
| | B | B |

TABLE 1-continued
| Structure | IC$_{50}$ | EC$_{50}$ |
|---|---|---|
| 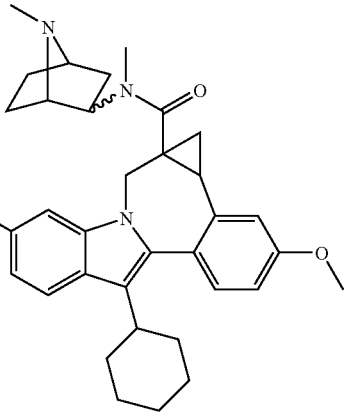 | B | B |
| 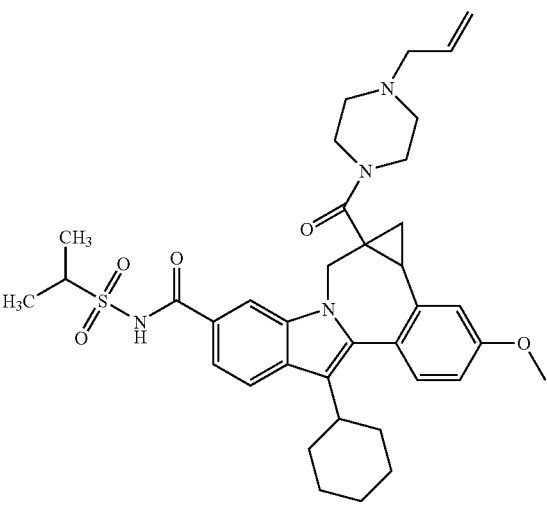 | B | B |
| 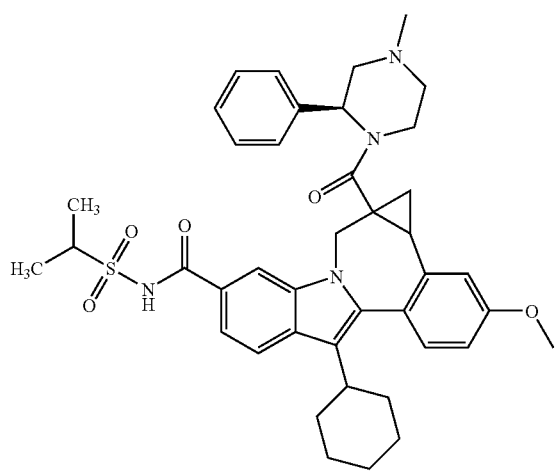 | B | B |

TABLE 1-continued

| Structure | IC$_{50}$ | EC$_{50}$ |
|---|---|---|
| | B | B |
| | B | B |
| | B | B |

TABLE 1-continued

| Structure | IC$_{50}$ | EC$_{50}$ |
|---|---|---|
| | B | B |
| | B | B |
| | B | B |

TABLE 1-continued

| Structure | IC$_{50}$ | EC$_{50}$ |
|---|---|---|
| [chemical structure] | B | B |

IC$_{50}$ A > 1 µM;
B 0.003 µM-1 µM;
EC$_{50}$:
C > 10 µM; D 1 µM-10µM; E 1.0 µM-0.02 µM.

Pharmaceutical Compositions and Methods of Treatment

Formula I compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 3.

TABLE 3

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |

TABLE 3-continued

| Brand Name | Type of Inhibitor or Target | Source Company |
| --- | --- | --- |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

Description of Specific Embodiments

Formula I compounds illustrated in the preceding schemes can generally be purified by reverse phase chromatography using a preparative C-18 column employing gradients of methanol-water containing 0.1% of trifluoroacetic acid (TFA), and using a Shimadzu High Perfomance Liquid Preparative Chromatographic System employing an XTERRA 30×100 mm S5 column at 40 mL/min flow rate with a 12 min gradient. An Emrys Optimizer personal microwave reactor was used for the microwave assisted reactions. Molecular weights and purities were usually determined using a Shimadzu LCMS using a Phenomenex-Luna 3.0×50 mm S 10 reverse phase column employing a flow rate of 4 mL min using a 0.1% TFA in methanol/H$_2$O gradient [0-100% in 2 min, with 3 min run time]. NMR spectra were usually obtained on either a Bruker 500 or 300 MHz instrument. The preparative silicic acid plates were 20×20 cm with a 1000 micron layer of silica gel GF.

Intermediate 1

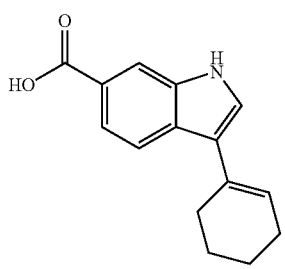

3-Cyclohexenyl-1H-indole-6-carboxylic acid. Cyclohexanone (96 mL, 0.926 mol) was added to a stirred solution of methyl indole-6-carboxylic acid (50.0 g, 0.335 mol) in methanol (920 mL) at 22° C. Methanolic sodium methoxide (416 mL of 25% w/w, 1.82 mol) was added in portions over 10 minutes. The mixture was stirred at reflux for 18 hours, cooled to room temperature, concentrated, diluted with cold water, and acidified with 36% HCl solution. The resulting precipitate was collected by filtration, washed with cold water, and dried over phosphorous pentoxide (0.1 mm) to provide the the title compound as a tan colored solid (80.9 g, 97.5% yield).

Intermediate 2

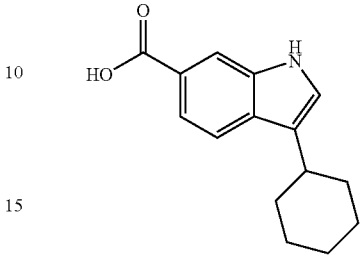

3-Cyclohexyl-1H-indole-6-carboxylic acid. 3-Cyclohexenyl-1H-indole-6-carboxylic acid (38 g) was added to a Parr bottle, followed by methanol (100 mL) and THF (100 mL). The bottle was flushed with argon and 10% palladium on carbon (1.2 g) was added. The flask was then evacuated and subsequently refilled with H$_2$ to a pressure of 55 psi, and the resultant mixture was shaken for 18 hours at RT. The catalyst was then removed by filtration through celite. Concentration of the filtrate provided the desired product as a pale purple solid (30.6 g, 79%). ESI-MS m/z 244 (MH$^+$).

Intermediate 3

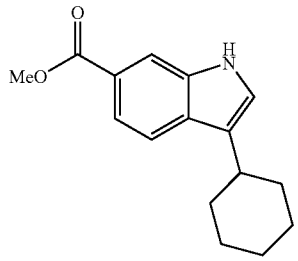

Methyl 3-cyclohexyl-1H-indole-6-carboxylate. Thionyl chloride (1 mL) was added to a stirred mixture of 3-cyclohexyl-1H-indole-6-carboxylic acid (30.4 g, 0.125 mol) in methanol (300 mL). The mixture was stirred at reflux for 18 hours, treated with decolorizing carbon, and filtered. The filtrate was concentrated to about 150 mL at which point crystallization occurred. The filtrate was cooled to room temperature and filtered. The solid was washed with cold methanol followed by diethyl ether to provide the desired product as a pale purple solid (22.2 g, 69% yield). ESI-MS m/z 258 (MH$^+$); $^1$H NMR (300 MHz, CDC$_3$) δ 1.35 (m, 4H), 1.63 (s, 1H), 1.78 (m, 3H), 2.06 (d, J=8.05 Hz, 2H, 3.90 (m, 1H), 7.08 (d, J=1.83 Hz, 1H), 7.62 (s, 1H), 7.65 (s, 1H), 7.74 (d, J=1.46 Hz, 1H), 7.77 (d, J=1.46 Hz, 1H), 8.08 (s, 1H).

Intermediate 4

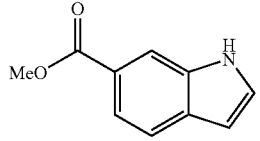

Methyl 1H-indole-6-carboxylate. An ethereal solution of diazomethane (620 mL) was added slowly to a cooled, (−15° C.) stirred suspension of 6-indole carboxylic acid (45 g, 0.27 mol.) in diethyl ether (250 mL). Upon addition, the reaction mixture was stirred for a further 1 h at −15° C., after which the reaction was quenched by the slow addition of acetic acid (50 mL). The resultant mixture was then concentrated under reduced pressure, and the residue purified using flash chromatography on silica (60-120), using DCM as eluant.

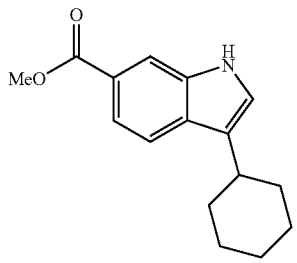

Intermediate 5

Methyl 3-cyclohexyl-1H-indole-6-carboxylate. Cyclohexanone (42.46 mL, 0.40 mol) was added in a single portion to a stirred solution of methyl indole-6-carboxylate (47.8 g, 0.27 m) in dry dichloromethane (500 mL). The reaction mixture was then cooled to 10° C. and trifluoroacetic acid (63.13 mL, 0.8 m) was added dropwise followed by triethyl silane (174.5 mL, 1.09 m). Upon addition, the temperature was allowed to rise to rt, after which it was stirred for a further 12 h. Dichloromethane (200 mL) was then added and the reaction mixture was washed successively with with 10% sodium bicarbonate solution and brine. The organic layer dried over sodium sulfate, filtered and concentrated under vacuum. The resultant residuce was purified by flash chromatography on silica (60-120) using hexane-ethyl acetate (9.5:0.5) mixture as eluant. Homogeneous fractions were combined and evaporated to give 60 g of the desired product (85%). Analytical data on this material was consistant with that observed with a sample prepared by the alternative route described above.

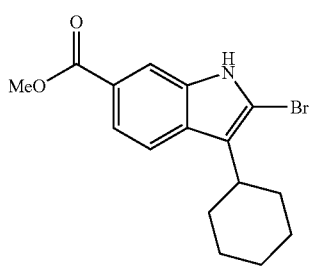

Intermediate 6

Methyl 2-bromo-3-cyclohexyl-2-1H-indole-6-carboxylate. Dry pyridinium tribromide (12.0 g, 38 mmol) was added in one portion to a stirred and cooled (ice/water bath) solution of methyl 3-cyclohexyl-1H-indole-6-carboxylate (7.71 g, 30 mmol) in a mixture of THF (80 mL) and chloroform (80 mL). The flask was removed from the cooling bath and stirring was continued for 2 hours at room temperature. The mixture was sequentially washed with 1M NaHSO$_3$ (2×50 mL) and 1N HCl (50 mL). It was then dried over anhydrous sodium sulfate, filtered, and concentrated. The concentrate was treated with hexanes and the resulting precipitate was collected by filtration to provide the desired product as an off-white solid (5.8 g, 58%). $^1$H NMR (300 MHz, CDC$_3$) δ 1.38 (m, 3H), 1.85 (m, 7H), 2.81 (m, 1H), 7.71 (m, 2H), 8.03 (s, 1H), 8.47 (s, 1H).

The hexane mother liquor was concentrated and the residue was dissolved in hexane/ethyl acetate (5:1). The solution was passed through a pad of silica gel with the same solvents. Concentration of the eluate followed by the addition of hexane (10 mL) resulted in the precipitation of additional product which was collected by filtration to provide 2.8 g (28%) of the desired product.

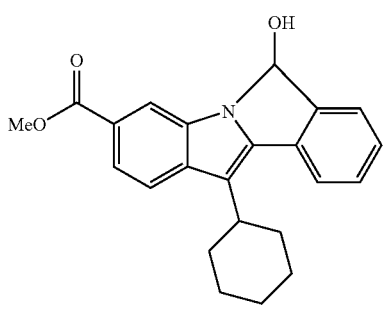

Intermediate 7

Methyl 11-cyclohexyl-6-hydroxy-6H-isoindolo[2,1-a]indole-3-carboxylate. A stirred mixture of methyl 2-bromo-3-cyclohexyl-1H-indole-6-carboxylate (10.1 g, 30 mmol), 2-formylphenylboronic acid (5.4 g, 36 mmol), LiCl (3.8 g (90 mmol) and Pd (PPh$_3$)$_4$ (1.6 g, 1.38 mmol) in 1M Na$_2$CO$_3$ (40 mL) and 1:1 EtOH-toluene (180 mL) was heated under nitrogen at 85° C. for 3 hours. The reaction mixture was then cooled to RT, and extracted with EtOAc (2×100 mL). The extracts were washed sequentially with water and brine, then dried (MgSO$_4$), filtered and conventrated in-vacuo to afforded 13.3 g of crude product. This material was triturated with DCM and hexanes to provide pure desired product (7.52 g, 70%). LC-MS: m/e 360 (M-H); 344 (M-17)$^+$. $^1$H NMR (400 MHz, CHLOROFORM-D) δ ppm 1.33-1.60 (m, 4 H) 1.77-2.01 (m, 6 H) 2.80 (d, J=11.83 Hz, 1 H) 3.02-3.18 (m, 1 H) 3.89 (s, 3 H) 6.49 (d, J=11.33 Hz, 1 H) 7.34 (t, J=7.55 Hz, 1 H) 7.46 (t, J=7.55 Hz, 1 H) 7.62 (d, J=7.30 Hz, 1 H) 7.66-7.74 (m, 2 H) 7.77 (d, J=7.81 Hz, 1 H) 8.21 (s, 1 H).

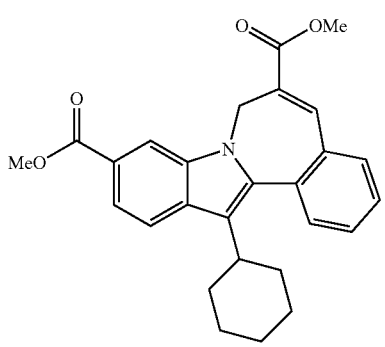

Intermediate 8

Methyl 13-cyclohexyl-6-(methoxycarbonyl)-7H-indolo[2,1-a][2]benzazepine-10-carboxylate. A stirred suspension of methyl 11-cyclohexyl-6-hydroxy-6H-isoindolo[2,1-a]indole-3-carboxylate (3.61 g, 10 mmol), Cs$_2$CO$_3$ (3.91 g, 12 mmol) and trimethyl 2-phosphonoacetate (2.86 g, 14 mmol) in an. DMF (40 mL) was heated at 60° C. under nitrogen for 3 h. The resultant yellow suspension was cooled to rt and water was added with vigorous stirring. A yellow precipitate formed which was collected by filtration. The filtrand was washed with water, and then air dried overnight to afford the title compound as a yellow powder (4.124 g, 96%). LC/MS: m/e 430 (MH+); 1H NMR (400 MHz, CHLOROFORM-D) δ ppm 1.30-1.46 (m, J=14.86 Hz, 2 H) 1.55 (s, 2 H) 1.77 (s, 2 H) 1.85-2.18 (m, 4 H) 2.76-2.89 (m, 1 H) 3.84 (s, 3 H) 3.95 (s, 3 H) 4.19 (s, 1 H) 5.68 (s, 1 H) 7.38-7.63 (m, 4 H) 7.74 (dd, J=8.44, 1.39 Hz, 1 H) 7.81-7.98 (m, 2 H) 8.29 (d, J=1.01 Hz, 1 H).

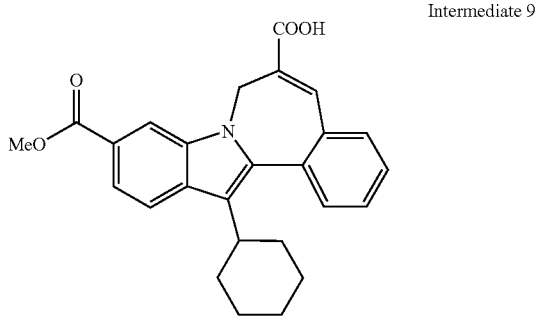

Intermediate 9

Methyl 13-cyclohexyl-6-(carboxy)-5H-indolo[2,1-a][2]benzazepine-10-carboxylate. Methyl 13-cyclohexyl-6-(methoxycarbonyl)-7H-indolo[2,1-a][2]benzazepine-10-carboxylate (308 mg, 0.72 mmol) was dissolved in N,N-dimethylformamide (5 mL) and treated with LiOH (173 mg, 7.2 mmol). The mixture was heated at 50° C. for 4 hr, afterwhich the solvent was removed in vacuo. The residue was dissolved in H$_2$O (5 mL) and the resultant mixture was acidified by the addition of a 10% aqueous HCL solution. A precipitate formed which was collected by filtration and air dried to afford the title compound as a bright yellow solid (290 mg, 97%). ESI-MS m/z [M+1]=415.

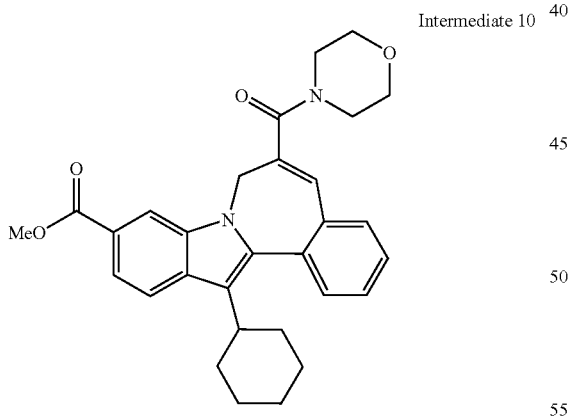

Intermediate 10

Methyl 13-cyclohexyl-6-(morpholinylcarbonyl)-5H-indolo[2,1-a][2]benzazepine-10-carboxylate. TBTU (145 mg, 0.45 mmol) was added to a stirred solution of Methyl 13-cyclohexyl-6-(carboxy)-5H-indolo[2,1-a][2]benzazepine-10-carboxylate (125 mg, 0.30 mmol), morpholine (26 μL, 0.30 mmol), and N,N-diisopropylethylamine 200 μL, 1.15 mmol) in DMF (2 mL). The mixture was stirred at 22° C. for 20 min. The resulting solution was then injected onto a Shimadzu reverse phase preparative HPLC. The product containing fraction was concentrated on a Speed Vac® to leave methyl 13-cyclohexyl-6-(morpholinylcarbonyl)-5H-indolo[2,1-a][2]benzazepine-10-carboxylic acid as a yellow solid (64 mg, 44%). ESI-MS m/z 487 (MH+); 1H NMR (500 MHz, CDCl$_3$) δ 1.21 (m, 1 H), 1.34-1.55 (m, 3 H), 1.77 (m, 2 H), 1.91 (m, 1 H), 2.06 (m, 3 H), 2.83 (m, 1 H), 2.97-3.85 (m, 8 H), 3.97 (s, 3 H), 4.45 (m, 1 H), 5.07 (m, 1 H), 6.89 (s, 1 H), 7.41 (d, 1 H), 7.49 (m, 2 H), 7.57 (m, 1 H), 7.75 (m, 1 H), 7.89 (d, J=8.55 Hz, 1 H), 8.15 (s, 1 H).

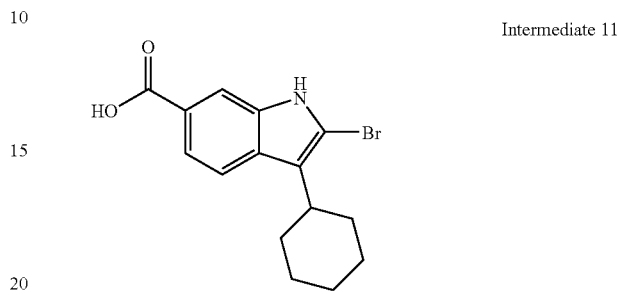

Intermediate 11

2-bromo-3-cyclohexyl-2-1H-indole-6-carboxylic acid. To a solution of methyl 2-bromo-3-cyclohexyl-2-1H-indole-6-carboxylate (8.0 g, 23.79 mmol) in THF/MeOH (30 mL/30 mL), 10 N solution of NaOH (23.8 mL, 238 mmoL) was added. The reaction mixture was stirred at 40° C. for 6 hrs, then at rt. for overnight. It was then concentrated and acidified with concentrated HCl solution to pH ~4. A brownish solid was collected as crude product. (7.6 g, 99% yield). MS m/322 (MH+), Retention time: 3.696 min.

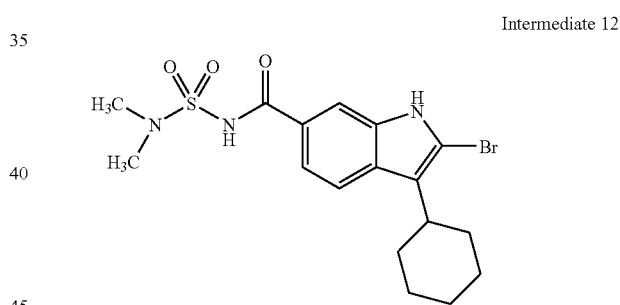

Intermediate 12

2-Bromo-3-cyclohexyl-N-[(dimethylamino)sulfonyl]-1H-indole-6-carboxamide. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of CO$_2$ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g, 8.8 mmol) in THF (4 mL). Stirring was continued for 24 hr. The mixture was partitioned between ethyl acetate and dilute HCl. The ethyl acetate layer was washed with water followed by brine and dried over Na$_2$SO$_4$. The extract was concentrated to dryness to leave the title product as a pale yellow friable foam, (2.0 g, 74%, >90% purity, estimated from NMR). 1H NMR (300 MHz, DMSO-D6) δ ppm 1.28-1.49 (m, 3 H) 1.59-2.04 (m, 7 H) 2.74-2.82 (m, 1 H) 2.88 (s, 6 H) 7.57 (dd, J=8.42, 1.46 Hz, 1 H) 7.74 (d, J=8.78 Hz, 1 H) 7.91 (s, 1 H) 11.71 (s, 1 H) 12.08 (s, 1 H).

Intermediate 13

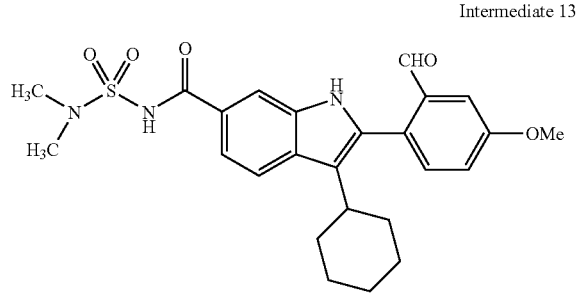

3-cyclohexyl-N-(N,N-dimethylsulfamoyl)-2-(2-formyl-4-methoxyphenyl)-1H-indole-6-carboxamide. A mixture of the 2-Bromo-3-cyclohexyl-N-[(dimethylamino)sulfonyl]-1H-indole-6-carboxamide (4.28 g, 0.01 mol), boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

Intermediate 15

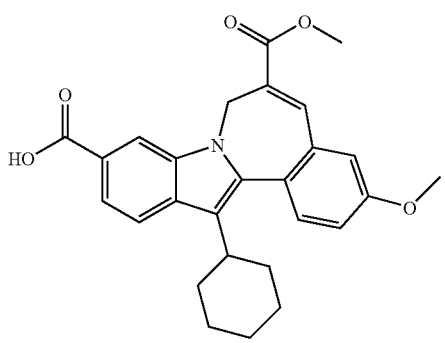

13-Cyclohexyl-3-methoxy-6-(methoxycarbonyl)-7H-indolo[2,1-a][2]benzazepine-10-carboxylic acid. Trifluoroacetic acid (30 mL) was added dropwise to a stirring slurry of 10-tert-butyl 6-methyl 13-cyclohexyl-3-methoxy-7H-indolo[2,1-a][2]benzazepine-6,10-dicarboxylate (10 g, 20 mmol) in dichloroethane (30 mL) under $N_2$. The clear dark green solution was stirred at rt for 2.5 h, concentrated to dryness and stirred with EtOAc (100 mL) overnight. The solids were collected by filtration, washed with EtOAc and $Et_2O$ to yield 13-cyclohexyl-3-methoxy-6-(methoxycarbonyl)-7H-indolo[2,1-a][2]benzazepine-10-carboxylic acid (8.35 g, 18.8 mmol, 94%) was as a yellow solid which was used without further purification. $^1$HNMR (300 MHz, $CDCl_3$) δ 1.13-2.16 (m, 10H), 2.74-2.88 (m, 1H), 3.84 (s, 3H), 3.89 (s, 3H), 4.06-4.29 (m, 1H), 5.54-5.76 (m, 1H), 6.98 (d, J=2.6 Hz, 1H), 7.08 (dd, J=8.4, 2.6 Hz, 1H), 7.52 (d, J=8.4 Hz, 1H), 7.78 (dd, J=8.8, 1.1 Hz, 1H), 7.80 (s, 1H), 7.86 (d, J=8.8 Hz, 1H), 8.34 (d, J=1.1 Hz, 1H). LCMS: m/e 446 (M+H)$^+$, ret time 3.21 min, column B, 4 minute gradient.

Intermediate 14

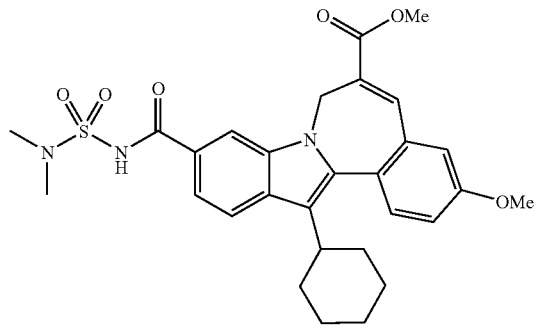

6-Carbomethoxy-13-cyclohexyl-N-[(dimethylamino)sulfonyl]-5H-indolo[2,1-a][2]b enzazepine-10-carboxamide. A mixture of the 3-cyclohexyl-N-(N,N-dimethylsulfamoyl)-2-(2-formyl-4-methoxyphenyl)-1H-indole-6-carboxamide (4.8 g, 0.01 mol), and cesium carbonate (7.1 g, 0.02 mol) and the trimethyl 2-phosphonoacetate (2.86 g, 0.014 mol) in DMF (28 mL) was stirred for 20 hr at an oil bath temperature of 55° C. The mixture was poured into ice-water and acidified with dilute HCl to precipitate the crude product. The solid was collected, dried and flash chromatographed on $SiO_2$ (110 g) using an ethyl acetate and methylene chloride (1:10) solution containing 2% acetic acid. Homogeneous fractions were combined and evaporated to afford the title compound as a pale yellow solid (3.9 g, 71% yield). MS:552 (M=H+).

Intermediate 16

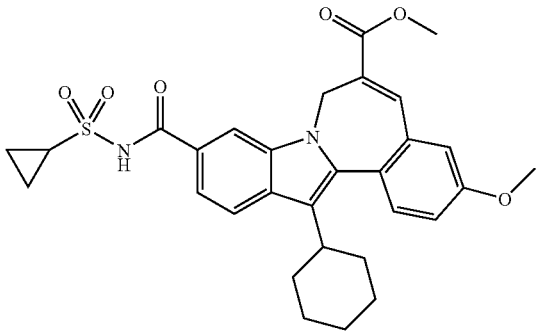

Methyl 13-cyclohexyl-10-((cyclopropylsulfonyl)carbamoyl)-3-methoxy-7H-indolo[2,1-a][2]benzazepine-6-carboxylate. 1,1'-Carbonyldiimidazole (1.82 g, 11.2 mmol) was added to a slurry of 13-cyclohexyl-3-methoxy-6-(methoxycarbonyl)-7H-indolo[2,1-a][2]benzazepine-10-carboxylic acid (3.85 g, 8.65 mmol) in THF (15 mL). The reaction mixture was heated at 60° C. for 1.5 h, cooled to rt, treated with cyclopropanesulfonamide (1.36 g, 11.2 mmol), stirred 10 min and then treated with the dropwise addition of a solution of DBU (2.0 mL, 13 mmol) in THF (3 mL). The reaction mixture was stirred at rt overnight, diluted with EtOAc (100 mL) and washed with $H_2O$ (~30 mL), 1N HCl (aq.) (2×50 mL) and brine (~30 mL). The combined aqueous layers were extracted with EtOAc (100 mL) and the organic layer was washed with 1N HCl (aq.) (~50 mL). The combined organic layers were washed with brine (~30 mL), dried (MgSO$_4$), filtered and concentrated. The residue was stirred with Et$_2$O (~100 mL) for 2 h and the solids were collected by filtration, rinsed with Et$_2$O and dried to yield methyl 13-cyclohexyl-10-((cyclopropylsulfonyl)carbamoyl)-3-methoxy-7H-indolo[2,1-a][2]benzazepine-6-carboxylate (4.24 g, 7.73 mmol, 89%) as a pale yellow solid which was used without further purification. $^1$HNMR (300 MHz, CDCl$_3$) δ 1.08-2.13 (m, 14H), 2.73-2.87 (m, 1H), 3.13-3.24 (m, 1H), 3.82 (s, 3H), 3.89 (s, 3H), 4.04-4.27 (m, 1H), 5.50-5.71 (m, 1H), 6.98 (d, J=2.6 Hz, 1H), 7.08 (dd, J=8.8, 2.6 Hz, 1H), 7.44 (dd, J=8.4, 1.1 Hz, 1H), 7.50 (d, J=8.8 Hz, 1H), 7.80 (s, 1H), 7.86 (d, J=8.4 Hz, 1H), 8.11 (br s, 1H), 8.78 (br s, 1H). LCMS: m/e 549 (M+H)$^+$, ret time 3.79 min, column B, 4 minute gradient.

Intermediate 17

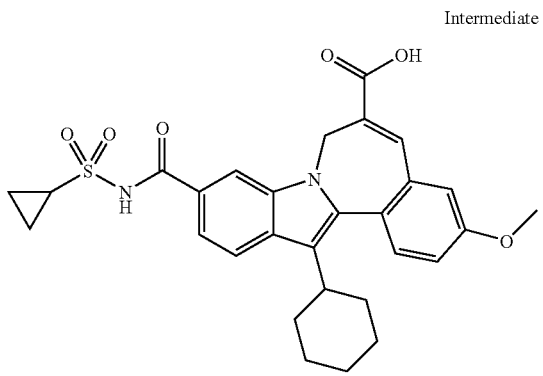

13-Cyclohexyl-10-((cyclopropylsulfonyl)carbamoyl)-3-methoxy-7H-indolo[2,1-a][2]benzazepine-6-carboxylic acid. Methyl 13-cyclohexyl-10-((cyclopropylsulfonyl)carbamoyl)-3-methoxy-7H-indolo [2,1-a][2]benzazepine-6-carboxylate (1.0 g, 1.8 mmol) was dissolved into MeOH//THF (1:1, 24 mL) and treated with 1M aqueous NaOH (5 mL). The reaction mixture was stirred and heated at 60° C. for 1.5 h and cooled to rt. The clear solution was neutralized with 1M aqueous HCl (5 mL) and concentrated to remove organic solvents. The resultant solids were collected by filtration, washed with H$_2$O and dried under vacuum to yield 13-cyclohexyl-10-((cyclopropylsulfonyl)carbamoyl)-3-methoxy-7H-indolo[2,1-a][2]benzazepine-6-carboxylic acid (1.0 g, 1.7 mmol, 94%) as a bright yellow solid (with 0.75 equiv. of THF) which was used without further purification. $^1$HNMR (300 MHz, CD$_3$OD) δ 1.11-2.24 (m, 17H, 3H from THF), 2.81-2.96 (m, 1H), 3.17-3.28 (m, 1H), 3.69-3.79 (m, 3H, from THF), 3.94 (s, 3H), 4.07-4.33 (m, 1H), 5.55-5.81 (m, 1H), 7.14-7.24 (m, 2H), 7.55-7.64 (m, 2H), 7.88-7.94 (m, 2H), 8.20 (br s, 1H). LCMS: m/e 535 (M+H)$^+$, ret time 3.73 min, column B, 4 minute gradient.

Intermediate 18

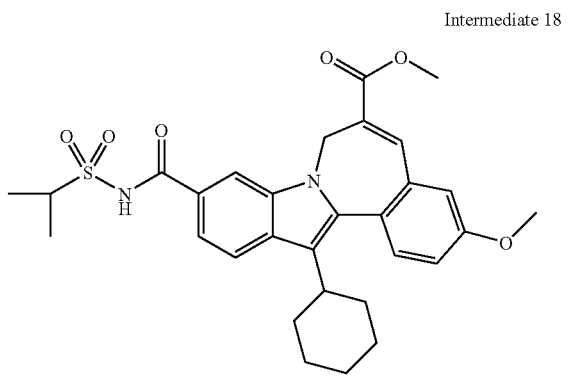

Methyl 13-cyclohexyl-10-((isopropylsulfonyl)carbamoyl)-3-methoxy-7H-indolo[2,1-a][2]benzazepine-6-carboxylate. 1,1'-Carbonyldiimidazole (262 mg, 1.62 mmol) was added to a slurry of 13-cyclohexyl-3-methoxy-6-(methoxycarbonyl)-7H-indolo[2,1-a][2]benzazepine-10-carboxylic acid (603 mg, 1.36 mmol) in THF (3 mL). The reaction mixture was heated at 60° C. for 1.5 h, cooled to rt, treated with propane-2-sulfonamide (200 mg, 1.62 mmol), stirred 10 min and then treated with the dropwise addition of a solution of DBU (0.27 mL, 1.8 mmol) in THF (0.75 mL). The reaction mixture was stirred at rt overnight, diluted with EtOAc (15 mL) and washed with H$_2$O (~5 mL), 1N HCl (aq.) (2×10 mL) and brine (~5 mL). The combined aqueous layers were extracted with EtOAc (15 mL) and the organic layer was washed with 1N HCl (aq.) (~10 mL). The combined organic layers were washed with brine (~5 mL), dried (MgSO$_4$), filtered and concentrated. The residue was stirred with Et$_2$O (~15 mL) for 2 h and the solids were collected by filtration, rinsed with Et$_2$O and dried to yield methyl 13-cyclohexyl-10-((isopropylsulfonyl)carbamoyl)-3-methoxy-7H-indolo[2,1-a][2]benzazepine-6-carboxylate (640 mg, 1.2 mmol, 85%) as a bright yellow solid which was used without further purification. $^1$HNMR (300 MHz, CDCl$_3$) δ 1.12-2.13 (m, 10H), 1.47 (d, J=7.0 Hz, 6H), 2.73-2.86 (m, 1H), 3.82 (s, 3H), 3.89 (s, 3H), 4.06-4.26 (m, 1H), 4.09 (septet, J=7.0 Hz, 1H), 5.51-5.71 (m, 1H), 6.98 (d, J=2.6 Hz, 1H), 7.08 (dd, J=8.4, 2.6 Hz, 1H), 7.44 (dd, J=8.4, 1.5 Hz, 1H), 7.50 (d, J=8.4 Hz, 1H), 7.80 (s, 1H), 7.87 (d, J=8.4 Hz, 1H), 8.10 (d, J=1.5 Hz, 1H), 8.57 (s, 1H). LCMS: m/e 551 (M+H)$^+$, ret time 3.87 min, column B, 4 minute gradient.

Intermediate 19

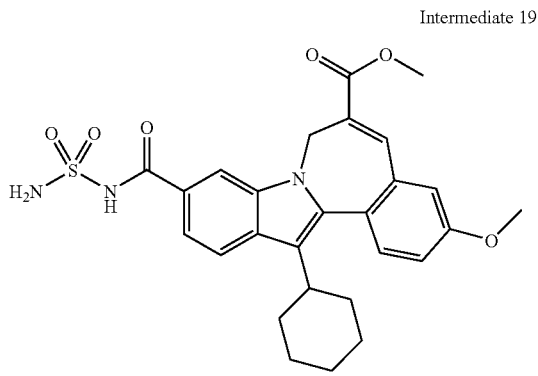

Methyl 10-((aminosulfonyl)carbamoyl)-13-cyclohexyl-3-methoxy-7H-indolo[2,1-a][2]benzazepine-6-carboxylate. 1,1'-Carbonyldiimidazole (1.23 g, 7.60 mmol) was added to a slurry of 13-cyclohexyl-3-methoxy-6-(methoxycarbonyl)-7H-indolo[2,1-a][2]benzazepine-10-carboxylic acid (2.6 g, 5.8 mmol) in THF (11 mL). The reaction mixture was heated at 60° C. for 1.5 h, cooled to rt, treated with sulfamide (1.12 g, 11.7 mmol), stirred 10 min and then treated with the dropwise addition of a solution of DBU (1.8 mL, 11.7 mmol) in THF (3 mL). The reaction mixture was stirred at rt for 3 h, diluted with EtOAc (80 mL) and CH$_2$Cl$_2$ (100 mL) and concentrated to dryness. The residue was diluted with CH$_2$Cl$_2$ (100 mL) and washed with 1N HCl (aq.) (2×100 mL). The combined aqueous layers were extracted with CH$_2$Cl$_2$ (100 mL) and the combined organic layers were washed with ½ saturated brine (~50 mL), dried (MgSO$_4$), filtered and concentrated. The residue was stirred with Et$_2$O (~75 mL) for 1h and the solids were collected by filtration, rinsed with Et₂O and dried to yield methyl 10-((aminosulfonyl)carbamoyl)-13-cyclohexyl-3-methoxy-7H-indolo[2,1-a][2]benzazepine-6-carboxylate (2.8 g, 5.3 mmol, 91%) as a bright yellow solid which was used without further purification. ¹HNMR (300 MHz, CDCl₃) δ 1.08-2.10 (m, 10H), 2.71-2.84 (m, 1H), 3.79 (s, 3H), 3.89 (s, 3H), 4.00-4.18 (m, 1H), 5.50-5.64 (m, 1H), 5.68 (s, 2H), 6.97 (d, J=2.6 Hz, 1H), 7.07 (dd, J=8.8, 2.6 Hz, 1H), 7.46 (dd, J=8.4, 1.5 Hz, 1H), 7.49 (d, J=8.8 Hz, 1H), 7.78 (s, 1H), 7.82 (d, J=8.4 Hz, 1H), 8.10 (br s, 1H), 9.49 (s, 1H). LCMS: m/e 524 (M+H)⁺, ret time 3.60 min, column B, 4 minute gradient.

Intermediate 20

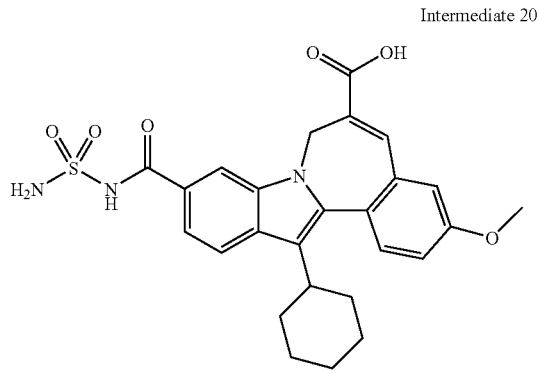

10-((Aminosulfonyl)carbamoyl)-13-cyclohexyl-3-methoxy-7H-indolo[2,1-a][2]benzazepine-6-carboxylic acid. Methyl 10-((aminosulfonyl)carbamoyl)-13-cyclohexyl-3-methoxy-7H-indolo[2,1-a][2]benzazepine-6-carboxylate (725 mg, 1.39 mmol) was dissolved into MeOH//THF (1:1, 16 mL) and treated with 1M aqueous NaOH (3 mL). The reaction mixture was stirred and heated at 60° C. for 0.5 h and cooled to rt. The reaction solution was diluted with MeOH/H₂O (2:1, 15 mL), neutralized with 1M aqueous HCl (3 mL) and concentrated to remove organic solvents. The resultant solids were collected by filtration, washed with H₂O and dried under vacuum to yield 10-((aminosulfonyl)carbamoyl)-13-cyclohexyl-3-methoxy-7H-indolo[2,1-a][2]benzazepine-6-carboxylic acid (650 g, 1.3 mmol, 92%) as a bright yellow solid which was used without further purification. ¹HNMR (300 MHz, CDCl₃) δ 1.16-2.22 (m, 10H), 2.82-2.96 (m, 1H), 3.94 (s, 3H), 4.07-4.29 (m, 1H), 5.57-5.80 (m, 1H), 7.14-7.23 (m, 2H), 7.55-7.63 (m, 2H), 7.88-7.94 (m 2H), 8.18 (s, 1H). LCMS: m/e 510 (M+H)⁺, ret time 2.85 min, column B, 4 minute gradient.

Intermediate 21

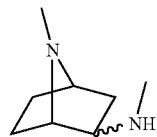

N,7-dimethyl-7-azabicyclo[2.2.1]heptan-2-amine. To a solution of benzyl-(7-methyl-7-aza-bicyclo[2.2.1]hept-2-yl)-amine (500 mg, 2.31 mmol) in MeOH (10 mL), Pd(OH)₂ with 20% Pd on carbon (125 mg) and 12N HCl solution (0.58 mL, 6.93 mmol) were added. The reaction mixture was shaken under a hydrogenator at 50 psi for overnight. The catalyst was filtered through celite and washed with methanol. The filtrate was concentrated and dried under vacuum to give a brownish solid as dihydrochloride salt. (430 mg, 87% yield). HPLC method: Method A: Start % B=0; Final % B=100; Gradient time=3 min; Flow Rate=4 ml/min; Wavelength=220; Solvent A=10% MeOH-90% H2O-0.1% TFA; Solvent B=90% MeOH-10% H2O-0.1% TFA; Column=Phenomenex-Luna 3.0×50 mm S10. MS m/z 141 (MH⁺); 1H NMR (500 MHz, MeOD) δ ppm exists as diasteromer mixture.

EXAMPLE 1

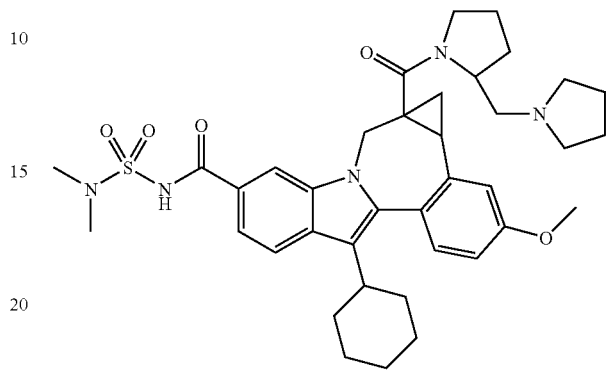

8-Cyclohexyl-N-((dimethylamino)sulfonyl)-11-methoxy-1a-((2-(1-pyrrolidinylmethyl)-1-pyrrolidinyl)carbonyl)-1, 1a,2,12b-tetrahydrocyclopropa[d]indolo[2,1-a][2]benzazepine-5-carboxamide. To a stirred solution of 8-cyclohexyl-5-(((dimethylamino)sulfonyl)carbamoyl)-11-methoxy-1, 12b-dihydrocyclopropa[d]indolo[2,1-a][2]benzazepine-1a (2H)-carboxylic acid (80 mg, 0.15 mmol), 1,3'-methylenedipyrrolidine (45 mg, 0.29 mmol) and triethylamine (0.15 mL) in DMF (1.5 mL) was added HATU (83 mg, 0.22 mmol). The reaction mixture was stirred at rt for 2 h, diluted with MeOH (4.5 mL) and purified by preparative HPLC (H₂O/CH₃CN with 10 mM NH₄OAc buffer) to yield 8-cyclohexyl-N-((dimethylamino)sulfonyl)-11-methoxy-1a-((2-(1-pyrrolidinylmethyl)-1-pyrrolidinyl)carbonyl)-1,1a,2, 12b-tetrahydrocyclopropa[d]indolo [2,1-a][2]benzazepine-5-carboxamide (75 mg, 0.11 mmol, 75%) as a white solid. Mixture of diastereomers. ¹HNMR (300 MHz, CD₃OD) δ 0.68-2.49 (m, 21H), 2.59-2.84 (m, 2H), 2.88-3.22 (m, 10H), 3.36-3.80 (m, 4H), 3.86-3.91 (m, 3H), 3.93-4.08 (m, 1H), 5.06-5.16 (m, 1H), 6.94-7.04 (m, 1H), 7.12-7.21 (m, 1H), 7.24-7.33 (m, 1H), 7.68-7.89 (m, 2H), 8.05-8.14 (m, 1H). LCMS: m/e 688 (M+H)⁺, ret time 2.58 min, column A, 4 minute gradient.

EXAMPLE 2

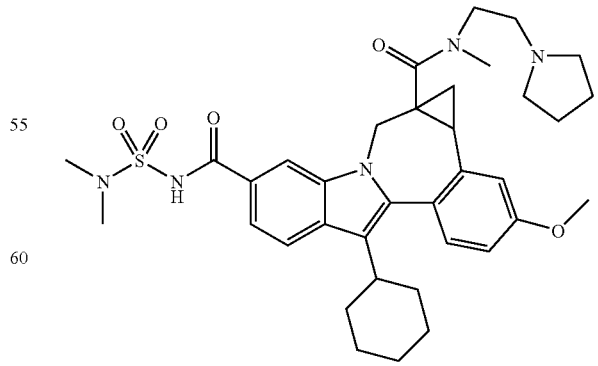

8-Cyclohexyl-N⁵-((dimethylamino)sulfonyl)-11-methoxy-N¹ᵃ-methyl-N¹ᵃ-(2-(1-pyrrolidinyl)ethyl)-1,12b-dihydrocyclopropa[d]indolo[2,1-a][2]benzazepine-1a,5(2H)-dicarboxamide. To a stirred solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (80 mg, 0.15 mmol), N-methyl-2-(pyrrolidin-1-yl)ethanamine (37 mg, 0.29 mmol) and triethylamine (0.15 mL) in DMF (1.5 mL) was added HATU (83 mg, 0.22 mmol). The reaction mixture was stirred at rt for 2 h, diluted with MeOH (4.5 mL) and purified by preparative HPLC ($H_2O$/$CH_3CN$ with 10 mM $NH_4OAc$ buffer) to yield 8-cyclohexyl-$N^5$-((dimethylamino)sulfonyl)-11-methoxy-$N^{1a}$-methyl-$N^{1a}$-(2-(1-pyrrolidinyl)ethyl)-1,12b-dihydrocyclopropa[d]indolo[2,1-a][2]benzazepine-1a,5(2H)-dicarboxamide (60 mg, 0.091 mmol, 63%) as a white solid. Presents as a 2:3 mixture of rotamers or atrope isomers. $^1$HNMR (300 MHz, DMSO-$d_6$) δ 0.98-2.11 (m, 16H), 2.76 (s, 3.6H), 2.79 (s, 2.4H), 2.66-3.59 (m, 13H), 3.51-3.59 (m, 0.4H), 3.85 (s, 1.8H), 3.85 (s, 1.2H), 4.02-4.11 (m, 0.6H), 4.78-4.88 (m, 0.4H), 5.00-5.09 (m, 0.6H), 6.98-7.07 (m, 1H), 7.12 (d, J=2.6 Hz, 0.6H), 7.21 (d, J=2.6 Hz, 0.4H), 7.27 (d, J=8.4 Hz, 1H), 7.64-7.83 (m, 2H), 8.04 (s, 0.6H), 8.23 (s, 0.4H). LCMS: m/e 660 (M–H)$^-$, ret time 2.49 min, column A, 4 minute gradient.

EXAMPLE 3

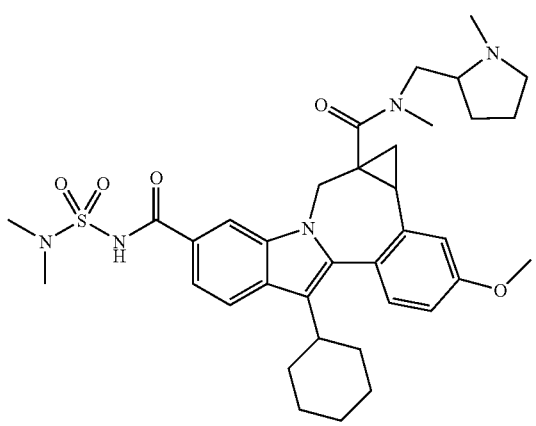

8-Cyclohexyl-$N^5$-((dimethylamino)sulfonyl)-11-methoxy-$N^{1a}$-methyl-$N^{1a}$-((1-methyl-2-pyrrolidinyl)methyl)-1,12b-dihydrocyclopropa[d]indolo[2,1-a][2]benzazepine-1a,5(2H)-dicarboxamide. To a stirred slurry of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (80 mg, 0.15 mmol), N-methyl-1-(1-methylpyrrolidin-2-yl)methanamine 1.45 oxalate salt (75 mg, 0.29 mmol) and triethylamine (0.15 mL) in DMF (1.5 mL) was added HATU (83 mg, 0.22 mmol). The reaction mixture was stirred at rt for 2 h, and additional HATU (300 mg, 0.79 mmol) and N-methyl-1-(1-methylpyrrolidin-2-yl)methanamine 1.45 oxalate salt (80 mg, 0.31 mmol) were added. After stirring at rt for 4 h, the reaction mixture was diluted with $H_2O$ (10 mL) and the precipitates were collected by filtration. The solids were dissolved into MeOH/DMF (4:1, 5 mL), filtered and purified by preparative HPLC ($H_2O$/$CH_3CN$ with 10 mM $NH_4OAc$ buffer) to yield 8-cyclohexyl-$N^5$-((dimethylamino)sulfonyl)-11-methoxy-$N^{1a}$-methyl-$N^{1a}$-((1-methyl-2-pyrrolidinyl)methyl)-1,12b-dihydrocyclopropa[d]indolo[2,1-a][2]benzazepine-1a,5(2H)-dicarboxamide (66 mg, 0.10 mmol, 69%) as awhite solid. Mixture of diastereomers. $^1$HNMR (300 MHz, $CD_3OD$) δ 1.15-2.42 (m, 18H), 2.61-3.75 (m, 18H), 3.89 (s, 3H), 5.07-5.18 (m, 1H), 6.95-7.03 (m, 1H), 7.14-7.19 (m, 1H), 7.24-7.33 (m, 1H), 7.66-7.77 (m, 1H), 7.78-7.86 (m, 1H), 8.05-8.15 (m, 1H). LCMS: m/e 660 (M–H)$^-$, ret time 2.42 min, column A, 4 minute gradient.

EXAMPLE 4

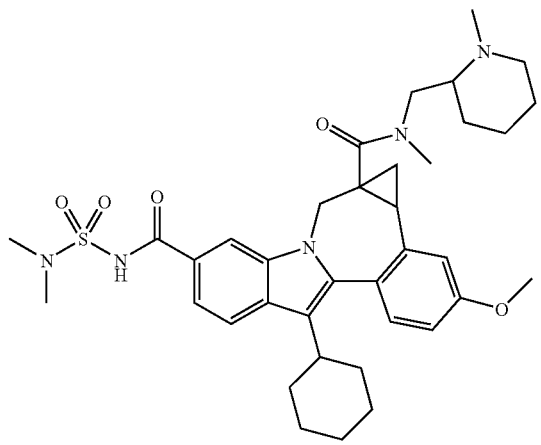

8-Cyclohexyl-$N^5$-((dimethylamino)sulfonyl)-11-methoxy-$N^{1a}$-methyl-$N^{1a}$-((1-methyl-2-piperidinyl)methyl)-1,12b-dihydrocyclopropa[d]indolo[2,1-a][2]benzazepine-1a,5(2H)-dicarboxamide. To a stirred slurry of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (80 mg, 0.15 mmol), N-methyl-1-(1-methylpiperidin-2-yl)methanamine 1.5 oxalate salt (80 mg, 0.29 mmol) and triethylamine (0.15 mL) in DMF (1.5 mL) was added HATU (83 mg, 0.22 mmol). The reaction mixture was stirred at rt for 2 h, and additional HATU (300 mg, 0.79 mmol) and N-methyl-1-(1-methylpyrrolidin-2-yl)methanamine 1.45 oxalate salt (80 mg, 0.29 mmol) were added. After stirring at rt for 4 h, the reaction mixture was diluted with $H_2O$ (10 mL) and the precipitates were collected by filtration. The solids were dissolved into MeOH/DMF (1:1, 4 mL), filtered and purified by preparative HPLC ($H_2O$/$CH_3CN$ with 10 mM $NH_4OAc$ buffer) to yield 8-cyclohexyl-$N^5$-((dimethylamino)sulfonyl)-11-methoxy-$N^{1a}$-methyl-$N^{1a}$-((1-methyl-2-piperidinyl)methyl)-1,12b-dihydrocyclopropa[d]indolo[2,1-a][2]benzazepine-1a,5(2H)-dicarboxamide (74 mg, 0.11 mmol, 76%) as a white solid. Complex mixture of diastereomers. $^1$HNMR (300 MHz, $CD_3OD$) δ 0.99-2.20 (m, 18H), 2.52-3.07 (m, 16H), 3.18-3.70 (m, 4H), 3.89 (s, 3H), 4.07-4.15 (m, 0.2H), 5.09-5.27 (m, 0.8H), 6.94-7.04 (m, 1H), 7.14-7.20 (m, 1H), 7.24-7.32 (m, 1H), 7.66-7.75 (m, 1H), 7.78-7.87 (m, 1H), 8.04-8.17 (m, 1H). LCMS: m/e 676 (M–H)$^-$, ret time 2.48 min, column A, 4 minute gradient.

EXAMPLE 5

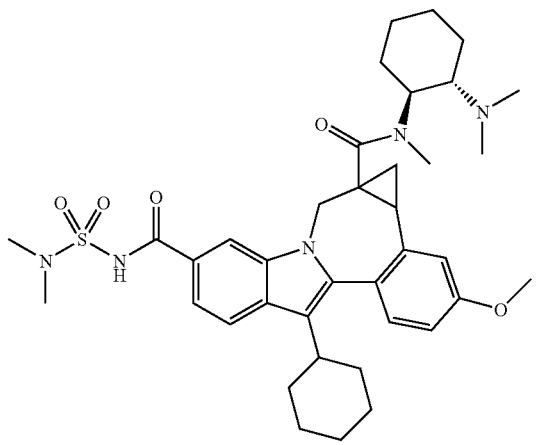

8-Cyclohexyl-N$^{1a}$-((1R,2R)-2-(dimethylamino)cyclohexyl)-N$^5$-((dimethylamino)sulfonyl)-11-methoxy-N$^{1a}$-methyl-1,12b-dihydrocyclopropa[d]indolo[2,1-a][2]benzazepine-1a,5(2H)-dicarboxamide. To a stirred solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (80 mg, 0.15 mmol), (1R,2R)-N$^1$,N$^1$,N$^2$-trimethylcyclohexane-1,2-diamine (56 mg, 0.29 mmol) and triethylamine (0.15 mL) in DMF (1.5 mL) was added HATU (83 mg, 0.22 mmol). The reaction mixture was stirred at rt for overnight, diluted with MeOH (1.5 mL) and purified by preparative HPLC (H$_2$O/CH$_3$CN with 10 mM NH$_4$OAc buffer) to yield 8-cyclohexyl-N$^{1a}$-((1R,2R)-2-(dimethylamino)cyclohexyl)-N$^5$-((dimethylamino)sulfonyl)-11-methoxy-N$^{1a}$-methyl-1,12b-dihydrocyclopropa[d]indolo[2,1-a][2]benzazepine-1a,5(2H)-dicarboxamide (39 mg, 0.057 mmol, 39%) as a white solid. Presents as a ~4:6 mixture of diastereomers.

$^1$HNMR (300 MHz, DMSO-d$_6$) δ 0.04-0.11 (m, 0.4H), 0.91-2.32 (m, 19.6H), 2.41-3.05 (m, 13H), 3.57 (d, J=15.0 Hz, 0.6H), 3.84 (s, 1.8H), 3.85 (s, 1.2H), 3.95-4.05 (m, 1.6H), 4.08 (d, J=15.0 Hz, 0.4H), 4.23-4.37 (m, 0.4H), 4.66 (d, J=15.0 Hz, 0.4H), 5.06 (d, J=15.4 Hz, 0.6H), 7.02 (dd, J=8.4, 2.6 Hz, 0.4H), 7.04 (dd, J=8.8, 2.6 Hz, 0.6H), 7.14 (d, J=2.6 Hz, 0.6H), 7.21-7.29 (m, 1.4H), 7.59 (d, J=8.4 Hz, 0.6H), 7.68 (d, J=8.4 Hz, 0.4H), 7.77 (d, J=8.4 Hz, 0.4H), 7.78 (d, J=8.4 Hz, 0.6H), 8.08 (s, 0.4H), 8.11 (s, 0.6H). LCMS: m/e 688 (M−H)$^−$, ret time 2.37 min, column A, 4 minute gradient.

EXAMPLE 6

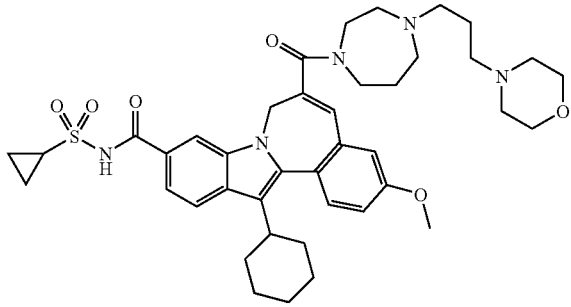

13-Cyclohexyl-N-(cyclopropylsulfonyl)-3-methoxy-6-((4-(3-(4-morpholinyl)propyl)-1,4-diazepan-1-yl)carbonyl)-7H-indolo[2,1-a][2]benzazepine-10-carboxamide. To a stirring solution of 13-cyclohexyl-10-((cyclopropylsulfonyl)carbamoyl)-3-methoxy-7H-indolo[2,1-a][2]benzazepine-6-carboxylic acid (33 mg, 0.062 mmol) and 4-(3-(1,4-diazepan-1-yl)propyl)morpholine (36 mg, 0.158 mmol) in DMF (0.5 ml) and TEA (50 μl, 0.359 mmol) was added HATU (35 mg, 0.092 mmol). The reaction mixture was stirred at room temperature under nitrogen for 4 h. The crude reaction mixture was diluted with MeOH (~1 mL), filtered and purified by preparative HPLC (H$_2$O/CH$_3$CN with 10 mM NH$_4$OAc) to yield 13-cyclohexyl-N-(cyclopropylsulfonyl)-3-methoxy-6-((4-(3-(4-morpholinyl)propyl)-1,4-diazepan-1-yl)carbonyl)-7H-indolo[2,1-a][2]benzazepine-10-carboxamide (35.1 mg, 0.045 mmol, 72.6% yield) as a yellow solid. $^1$HNMR (300 MHz, CD$_3$OD) δ 0.91-2.34 (m, 20H), 2.49-3.49 (m, 15H), 3.81-3.96 (m, 7H), 4.03-4.23 (m, 1H), 4.30-4.48 (m, 1H), 5.05-5.23 (m, 1H), 6.90 (s, 1H) 7.04 (d, J=2.6 Hz, 1H), 7.13 (dd, J=8.4, 2.6 Hz, 1H), 7.53 (d, J=8.4 Hz, 1H), 7.42-7.88 (m, 2H), 8.24 (s, 1H). LCMS: m/e 744 (M+H)$^+$, ret time 2.88 min, column B, 4 minute gradient.

EXAMPLE 7

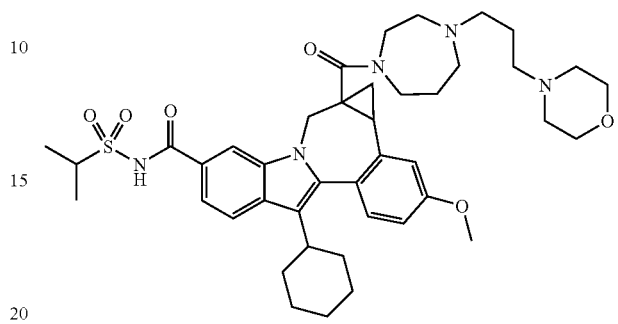

8-Cyclohexyl-N-(isopropylsulfonyl)-11-methoxy-1a-((4-(3-(4-morpholinyl)propyl)-1,4-diazepan-1-yl)carbonyl)-1,1a,2,12b-tetrahydrocyclopropa[d]indolo[2,1-a][2]benzazepine-5-carboxamide. To a stirring solution of 8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (39.0 mg, 0.071 mmol) and 4-(3-(1,4-diazepan-1-yl)propyl)morpholine (34.0 mg, 0.150 mmol) in DMF (0.5 ml) and TEA (50 μl, 0.359 mmol) was added HATU (35 mg, 0.092 mmol). The reaction mixture was stirred at room temperature under nitrogen for 4 h. The reaction was complete by LCMS. The crude reaction mixture was diluted with MeOH (~1 mL), filtered and purified by preparative HPLC (H$_2$O/CH$_3$CN with 10 mM NH$_4$OAc) to yield 8-cyclohexyl-N-(isopropylsulfonyl)-11-methoxy-1a-((4-(3-(4-morpholinyl)propyl)-1,4-diazepan-1-yl)carbonyl)-1,1a,2,12b-tetrahydrocyclopropa[d]indolo[2,1-a][2]benzazepine-5-carboxamide (42.8 mg, 0.056 mmol, 80% yield) as a white solid. Presents as a complex mixture of rotamers and/or atrope isomers. $^1$HNMR (300 MHz, CD$_3$OD) δ 0.15-0.25 (m, 0.3H), 1.17-2.23 (m, 23.7), 2.37-3.20 (m, 15H), 3.49-4.15 (m, 10.3H), 5.20 (d, J=15.0 Hz, 0.7 H), 6.94-7.04 (m, 1H), 7.13-7.20 (m, 1H), 7.24-7.34 (m, 1H), 7.70-7.87 (m, 1H), 8.14-8.24 (m, 1H). LCMS: m/e 760 (M+H)$^+$, ret time 2.88 min, column B, 4 minute gradient.

EXAMPLE 8

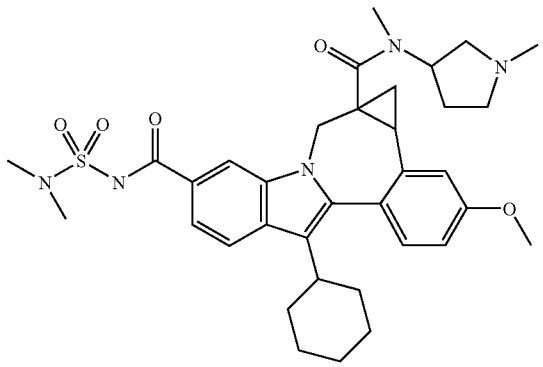

8-Cyclohexyl-$N^5$-((dimethylamino)sulfonyl)-11-methoxy-$N^{1a}$-methyl-$N^{1a}$-(1-methyl-3-pyrrolidinyl)-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (120 mg, 0.22 mmol) and N,1-dimethylpyrrolidin-3-amine (33 mg, 0.29 mmol) in DMF (2 mL) and TEA (0.1 mL) was added HATU (108 mg, 0.28 mmol). The reaction was stirred at rt for 16h, diluted with MeOH and purified by prep HPLC ($H_2O$/MeOH with 0.1% TFA buffer) to yield 8-cyclohexyl-$N^5$-((dimethylamino)sulfonyl)-11-methoxy-$N^{1a}$-methyl-$N^{1a}$-(1-methyl-3-pyrrolidinyl)-1,12b-dihydrocyclopropa[d]indolo[2,1-a][2]benzazepine-1a,5(2H)-dicarboxamide (99 mg, 0.15 mmol, 70%) as a yellow solid. Presents as a 1:6 mixture of diastereomers. $^1$H NMR (300 MHz, MeOD) δ ppm 8.09-8.13 (m, 0.15H), 7.85-8.00 (m, 1.85H), 7.54-7.64 (m, 1H), 7.29-7.37 (m, 1H), 7.15-7.22 (m, 1H), 6.96-7.07 (m, 1H), 5.11 (dd, J=15.4, 3.3 Hz, 0.85H), 4.79-4.90 (m, 0.15H), 3.92 (s, 0.45H), 3.91 (s, 2.55H), 3.04 (s, 6H), 2.48-4.25 (m, 14H), 1.06-2.46 (m, 13.85H), 0.15-0.25 (m, 0.15H). LCMS: m/e 648 (M+H)$^+$, Column A, Gradient time: 2 min, ret time 1.21 min.

EXAMPLE 9

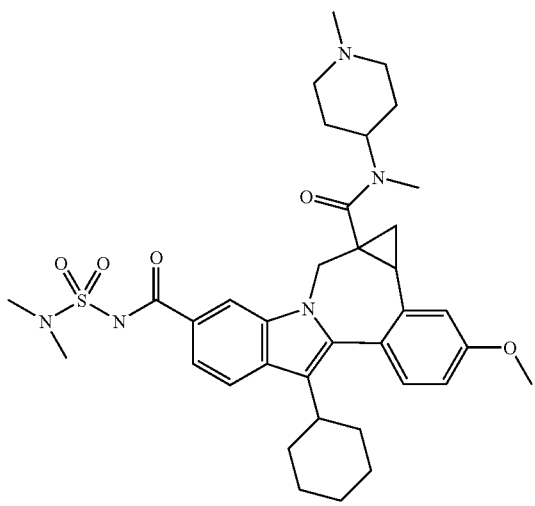

8-Cyclohexyl-$N^5$-((dimethylamino)sulfonyl)-11-methoxy-$N^{1a}$-methyl-$N^{1a}$-(1-methyl-4-piperidinyl)-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (50 mg, 0.091 mmol) and N,1-dimethylpiperidin-4-amine (15 mg, 0.12 mmol) in DMF (1 mL) and TEA (0.05 mL) was added HATU (45 mg, 0.12 mmol). The reaction was stirred at rt for 2 h, diluted with MeOH and purified by prep HPLC ($H_2O$/MeOH with 0.1% TFA buffer) to yield 8-cyclohexyl-$N^5$-((dimethylamino)sulfonyl)-11-methoxy-$N^{1a}$-methyl-$N^{1a}$-(1-methyl-4-piperidinyl)-1,12b-dihydrocyclopropa[d]indolo[2,1-a][2]benzazepine-1a,5(2H)-dicarboxamide (51 mg, 0.077 mmol, 85%) as a yellow solid. Presents as a 1:6 mixture of rotamers or atrope isomers. $^1$H NMR (300 MHz, MeOD) δ ppm 8.05-8.09 (m, 0.15H), 7.84-7.95 (m, 1.85H), 7.62 (dd, J=8.4, 1.5 Hz, 0.15H), 7.56 (dd, J=8.4, 1.5 Hz, 0.85H), 7.34 (d, J=8.4 Hz, 1H), 7.20 (d, J=2.6 Hz, 1H) 7.04 (dd, J=8.4, 2.6 Hz, 1H), 5.08 (d, J=15.4 Hz, 0.85H), 4.76-4.87 (m, 0.15H), 4.01-4.22 (m, 1H), 3.92 (s, 0.45H), 3.90 (s, 2.55H), 3.64 (d, J=15.4 Hz, 0.85H), 3.37-3.82 (m, 2.15H), 3.03 (s, 6H), 2.83 (s, 3H), 2.47-3.28 (m, 7H), 1.03-2.30 (m, 15.85H), 0.16-0.27 (m, 0.15H). LCMS: m/e 662 (M+H)$^+$, Column A, Gradient time: 2 min, ret time 1.19 min.

EXAMPLE 10

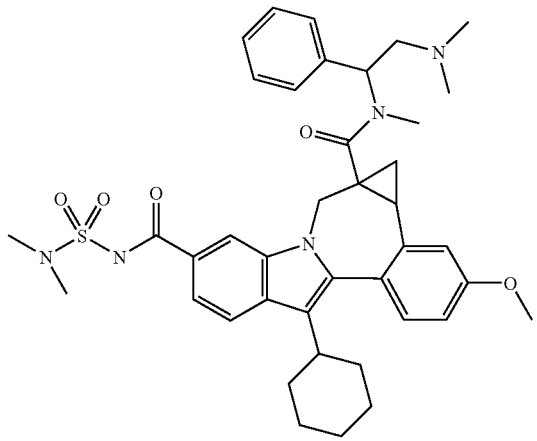

8-Cyclohexyl-$N^{1a}$-(2-(dimethylamino)-1-phenylethyl)-$N^5$-((dimethylamino)sulfonyl)-11-methoxy-$N^{1a}$-methyl-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and $N^1$,$N^1$,$N^2$-trimethyl-$N^2$-phenylethane-1,2-diamine (25 mg, 0.14 mmol) in DMF (1 mL) and TEA (0.06 mL) was added HATU (54 mg, 0.14 mmol). The reaction was stirred at rt for 2 h, diluted with MeOH and purified by prep HPLC ($H_2O$/MeOH with 0.1% TFA buffer) to yield 8-cyclohexyl-$N^{1a}$-(2-(dimethylamino)-1-phenylethyl)-$N^5$-((dimethylamino)sulfonyl)-11-methoxy-$N^{1a}$-methyl-1,12b-dihydrocyclopropa[d]indolo[2,1-a][2]benzazepine-1a,5(2H)-dicarboxamide (69 mg, 0.097 mmol, 88%) as a yellow solid. Presents as a complex mixture of diastereomers. $^1$H NMR (300 MHz, MeOD) δ ppm 8.13 (br s, 0.06H), 8.04 (br s, 0.2H), 7.87-7.97 (m, 1.54H), 7.82 (d, J=8.8 Hz, 0.2H), 7.39-7.65 (m, 4H), 7.19-7.38 (m, 3H), 7.18 (d, J=2.2, 0.8H), 7.10 (d, J=2.2 Hz, 0.2H), 4.72-6.29 (m, 2H), 3.86-3.91 (m, 3H), 3.74-4.23 (m, 1H), 3.51-3.69 (m, 1.5H), 3.21-3.32 (m, 0.5H), 2.92-3.13 (m, 9H), 2.37-2.90 (m, 8H), 1.06-2.23 (m, 11.8H), 0.15-0.26 (m, 0.2H). LCMS: m/e 712 (M+H)$^+$, Column A, Gradient time: 4 min, ret time 2.38 min.

EXAMPLE 11

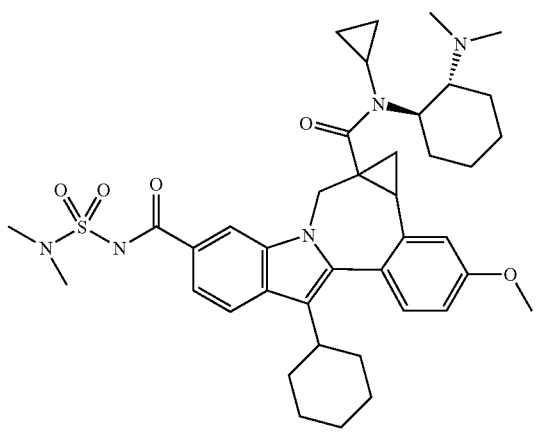

8-Cyclohexyl-$N^{1a}$-cyclopropyl-$N^{1a}$-((1R,2R)-2-(dimethylamino)cyclohexyl)-$N^5$-((dimethylamino)sulfonyl-11-methoxy-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and (1R,2R)-N$^1$-cyclopropyl-N$^2$,N$^2$-dimethylcyclohexane-1,2-diamine (26 mg, 0.14 mmol) in DMF (1 mL) and TEA (0.06 mL) was added HATU (54 mg, 0.14 mmol). The reaction was stirred at rt for 1 h, diluted with MeOH and purified by prep HPLC (H$_2$O/MeOH with 0.1% TFA buffer) to yield 8-cyclohexyl-N$^{1a}$-cyclopropyl-N$^{1a}$-((1R,2R)-2-(dimethylamino)cyclohexyl)-N$^5$-((dimethylamino)sulfonyl)-11-methoxy-1,12b-dihydrocyclopropa[d]indolo[2,1-a][2]benzazepine-1a,5(2H)-dicarboxamide (40 mg, 0.056 mmol, 51%) as a yellow solid. Presents as a 1:3 mixture of diastereomers. $^1$H NMR (300 MHz, MeOD) δ ppm 8.09 (s, 0.75H), 8.01 (s, 0.25H), 7.89 (d, J=8.8 Hz, 0.75H), 7.87-7.94 (m, 0.25H), 7.60 (dd, J=8.4, 1.5 Hz, 1H), 7.34 (d, J=8.8 Hz, 0.25H), 7.26 (d, J=8.4 Hz, 0.75H), 7.19 (d, J=2.6 Hz, 0.75H), 7.17 (d, J=2.6 Hz, 0.25H), 7.01 (dd, J=8.8, 2.6 Hz, 0.75H), 6.97-7.06 (m, 0.25H), 5.54 (d, J=15.7 Hz, 0.75H), 4.92-5.00 (m, 0.25H), 4.29-4.40 (m, 0.25H), 3.92 (s, 0.75H), 3.91 (s, 2.25H), 3.81-4.10 (m, 1H), 3.61 (d, J=15.7 Hz, 0.75H), 3.04-3.52 (m, 2H), 3.03 (s, 6H), 2.62-3.01 (m, 8H), 0.68-2.30 (m, 23.75H), 0.13-0.21 (m, 0.25H). LCMS: m/e 716 (M+H)$^+$, Column A, Gradient time: 4 min, ret time 2.56 min.

EXAMPLE 12

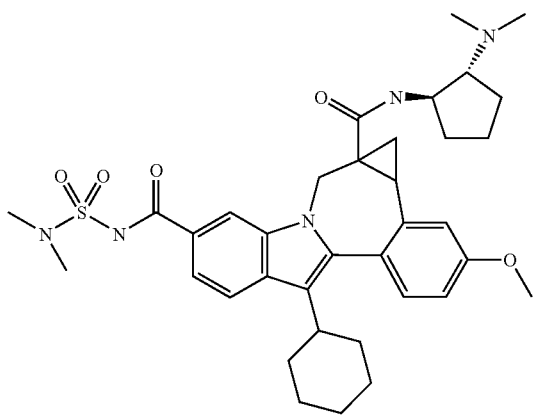

8-Cyclohexyl-N$^{1a}$-((1R,2R)-2-(dimethylamino)cyclopentyl)-N$^5$-((dimethylamino)sulfonyl)-11-methoxy-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and (1R,2R)-N$^1$,N$^1$-dimethylcyclopentane-1,2-diamine (18 mg, 0.14 mmol) in DMF (1 mL) and TEA (0.06 mL) was added HATU (54 mg, 0.14 mmol). The reaction was stirred at rt for 1 h, diluted with MeOH and purified by prep HPLC (H$_2$O/MeOH with 0.1% TFA buffer) to yield 8-cyclohexyl-N$^{1a}$-((1R,2R)-2-(dimethylamino)cyclopentyl)-N$^5$-((dimethylamino)sulfonyl)-11-methoxy-1,12b-dihydrocyclopropa[d]indolo[2,1-a][2]benzazepine-1a,5(2H)-dicarboxamide (33 mg, 0.050 mmol, 45%) as a yellow solid. Complex mixture of diastereomers. $^1$H NMR (300 MHz, MeOD) δ ppm 8.26 (br s, 0.15H), 8.22 (br s, 0.6H), 8.08 (br s, 0.15H), 7.75-8.01 (m, 1.1H), 7.52-7.66 (m, 1H), 6.98-7.37 (m, 3H), 4.87-5.85 (m, 1H), 4.07-4.53 (m, 1H), 3.91 (s, 3H), 3.46-3.77 (m, 1H), 3.03 3.05 (m, 6H), 2.77-3.29 (m, 4H), 1.18-2.68 (m, 22.85H), 0.16-0.24 (m, 0.15H). LCMS: m/e 662 (M+H)$^+$, Column A, Gradient time: 4 min, ret time 2.17 min.

EXAMPLE 13

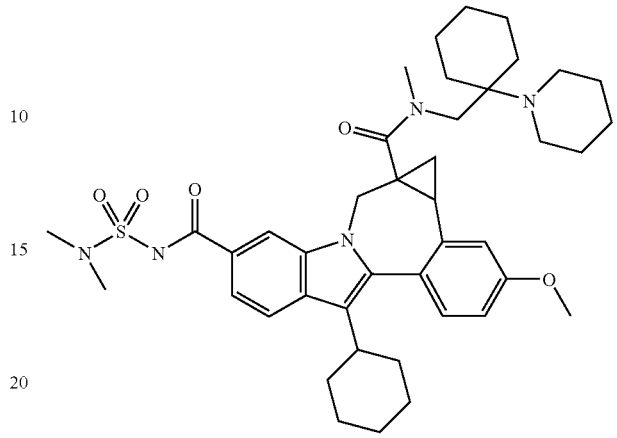

8-Cyclohexyl-N$^5$-((dimethylamino)sulfonyl)-11-methoxy-N$^{1a}$-methyl-N$^{1a}$-((1-(1-piperidinyl)cyclohexyl)methyl)-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and N-methyl-1-(1-(piperidin-1-yl)cyclohexyl)methanamine (30 mg, 0.14 mmol) in DMF (1 mL) and TEA (0.06 mL) was added HATU (54 mg, 0.14 mmol). The reaction was stirred at rt for 1 h, diluted with MeOH and purified by prep HPLC (H$_2$O/MeOH with 0.1% TFA buffer) to yield 8-cyclohexyl-N$^{52}$-((dimethylamino)sulfonyl)-11-methoxy-N$^{1a}$-methyl-N$^{1a}$-((1-(1-piperidinyl)cyclohexyl)methyl)-1,12b-dihydrocyclopropa[d]indolo[2,1-a][2]benzazepine-1a,5(2H)-dicarboxamide (72 mg, 0.097 mmol, 88%) as a yellow solid. Presents as a 1:9 mixture of rotamers or atrope isomers. $^1$H NMR (300 MHz, MeOD) δ ppm 8.08 (s, 1H), 7.91-7.99 (m, 1H), 7.62 (d, J=8.8 Hz, 1H), 7.33 (d, J=8.8 Hz, 1H), 7.21 (s, 1H), 7.06 (d, J=8.8 Hz, 1H), 5.20 (d, J=15.4 Hz, 1H), 3.89-3.94 (m, 3H), 3.29-3.96 (m, 5H), 3.04 (s, 6H), 2.50-3.02 (m, 5H), 1.13-2.23 (m, 29.1H), 0.23-0.89 (m, 0.9H). LCMS: m/e 744 (M+H)$^-$, Column A, Gradient time: 4 min, ret time 2.63 min.

EXAMPLE 14

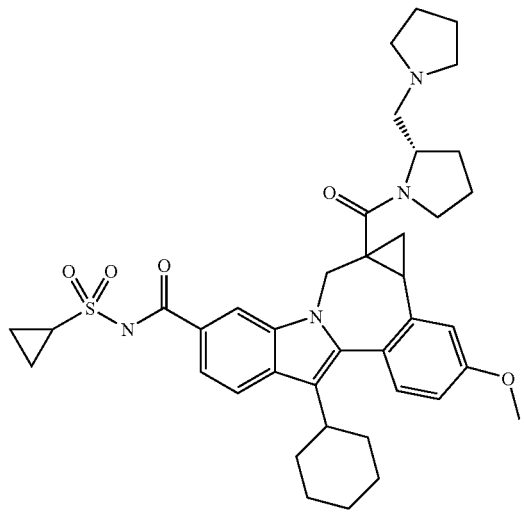

(+/−)-8-cyclohexyl-N-(cyclopropylsulfonyl)-1,1a,2,12b-tetrahydro-11-methoxy-1a-((S)-1-(2-(pyrrolidin-1-ylmethyl)pyrrolidin-1-yl))-8-carbonyl)-cycloprop[d]indolo[2,1-a][2]benzazepine-5-carboxamide. A TFA salt was prepared (0.0556 g, 64%). LC-MS retention time: 3.38; MS m/z 710 (M+H).

EXAMPLE 15

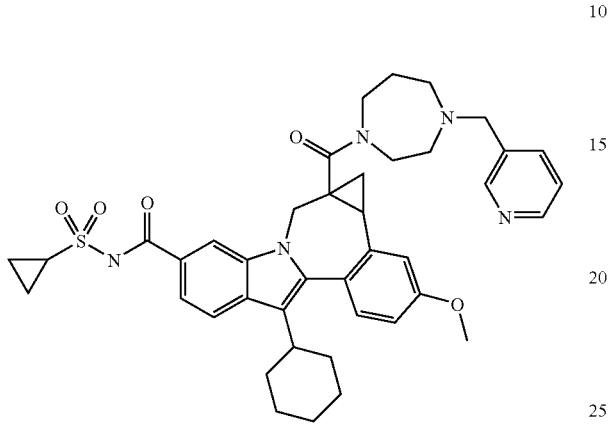

(+/−) 8-cyclohexyl-N-(cyclopropylsulfonyl)-1,1a,2,12b-tetrahydro-11-methoxy-1a-(11-(4-(pyridin-3-ylmethyl)-1,4-diazepan-1-yl))-8-carbonyl)-cycloprop[d]indolo[2,1-a][2]benzazepine-5-carboxamide. A TFA salt was prepared (0.0612 g, 71%). LC-MS retention time: 2.97; MS m/z 722 (M+H). $^1$H NMR (400 MHz, ppm 0.13-0.42 (m, 1 H), 1.04-1.54 (m, 9 H), 1.68-2.22 (m, 9 H), 2.63 (s, 2 H), 2.81-3.39 (m, 5 H), 3.63 (d, J=15.11 Hz, 1 H), 3.90 (s, 3 H), 3.91-4.16 (m, 3 H), 5.12-5.36 (m, 1 H), 6.98 (dd, J=8.56, 2.27 Hz, 1 H), 7.09-7.15 (m, 1 H), 7.29 (d, J=8.56 Hz, 1 H), 7.74-7.99 (m, 3 H), 8.21 (s, 1 H), 8.53 (s, 1 H), 8.81 (d, J=5.04 Hz, 1 H), 9.09 (s, 1 H).

EXAMPLE 16

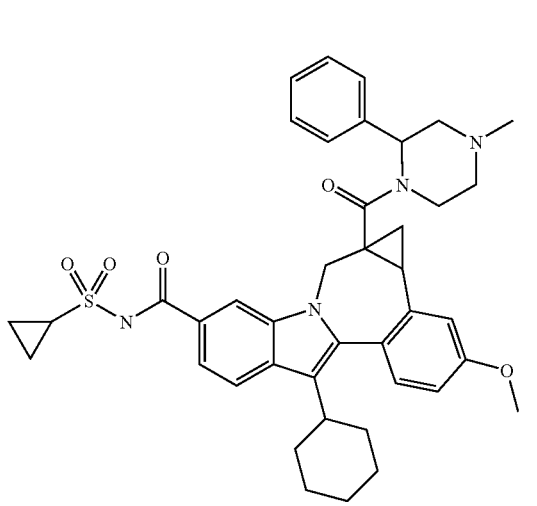

(+/−)-8-cyclohexyl-N-(cyclopropylsulfonyl)-1,1a,2,12b-tetrahydro-11-methoxy-1a-(1-(4-methyl-2-phenylpiperazin-1-yl)-8-carbonyl)-cycloprop[d]indolo[2,1-a][2]benzazepine-5-carboxamide. A TFA salt was prepared (0.0374 g, 43%). LC-MS retention time: 3.15; MS m/z 707 (M+H).

EXAMPLE 17

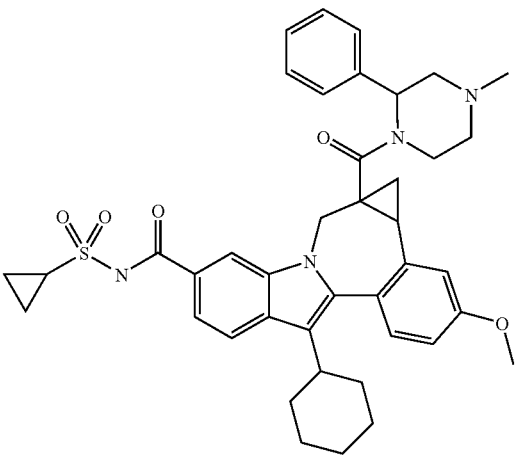

(+/−) 8-cyclohexyl-N-(cyclopropylsulfonyl)-1,1a,2,12b-tetrahydro-11-methoxy-1a-((2S,6R)-2,6-dimethylmorpholino)-8-carbonyl)-cycloprop[d]indolo[2,1-a][2]benzazepine-5-carboxamide. A TFA salt was prepared (0.0532 g, 75%). LC-MS retention time: 3.44; MS m/z 646 (M+H).

EXAMPLE 18

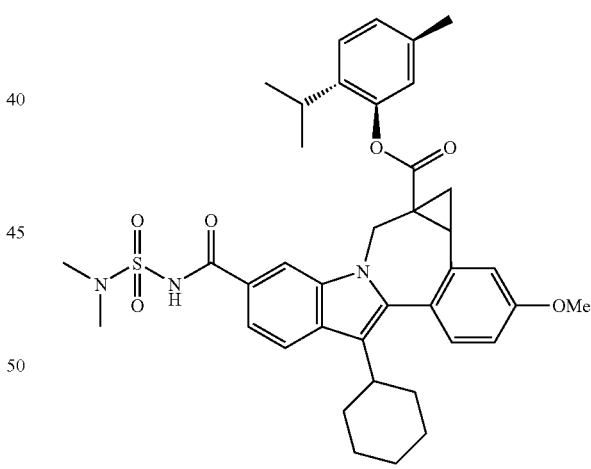

(1R,2S,5R)-2-Isopropyl-5-methylcyclohexyl 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylate. Analytical HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=690.52, HPLC R$_t$=2.243 min. Analytical HPLC method: Solvent A=5% MeCN—95% H$_2$O—10 mM NH$_4$OAc, Solvent B=95% MeCN—5% H$_2$O—10 mM NH$_4$OAc, Start % B=0, Final % B=100, Gradient time=2 min, Flow Rate=5 ml/min, Column: Phenomenex Lina C18 5 um 3.0×50 mm; LCAMS: (ES+) m/z (M+H)$^+$=690.42, HPLC R$_t$=2.108 min.

EXAMPLE 19

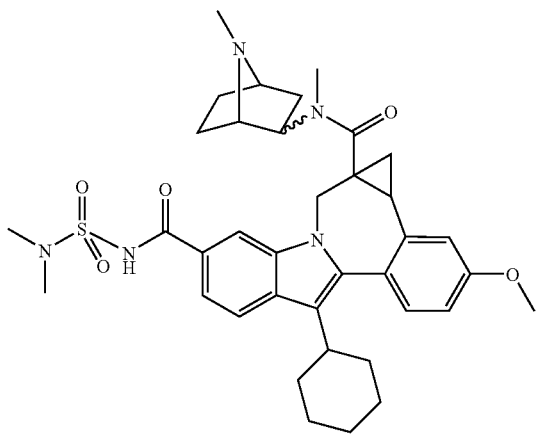

Cycloprop[d]indolo[2,1-a][2]benzazepine-1a,5(2H)-dicarboxamide, 8-cyclohexyl-N$^5$-[(dimethylamino)sulfonyl]-1,12b-dihydro-11-methoxy-N$^{1a}$-methyl-N$^{1a}$-(7-methyl-7-azabicyclo[2.2.1]hept-2-yl)-. To a solution of cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (55 mg, 0.1 mmol) in DMSO (2.0 mL), TBTU (48 mg, 0.15 mmol) and DIPEA (0.105 mL, 0.6 mmol) were added. The reaction mixture was stirred at RT for 15 min. Then N,7-dimethyl-7-azabicyclo[2.2.1]heptan-2-amine dihydrochloride (32 mg, 0.15 mmol) was added and the reaction mixture was stirred at RT for overnight. It was then concentrated and the residue was purified by Prep. HPLC column to give a light yellow solid as final TFA salt. (55 mg, 70% yield). HPLC method: Method A: Start % B=0; Final % B=100; Gradient time=3 min; Flow Rate=4 ml/min; Wavelength=220; Solvent A=10% MeOH—90% H2O—0.1% TFA; Solvent B=90% MeOH—10% H2O—0.1% TFA; Column=Phenomenex-Luna 3.0×50 mm S10. MS m/z 674(MH$^+$), Retention time: 2.558 min. (Method A). 1H NMR (500 MHz, MeOD) δ ppm exists as diasteromer mixture.

The general methods that follow pertain to the experimental procedures used to prepare Examples 2 and 3. Analytical HPLC and LC/MS were performed by using Shimadzu-VP instrument with UV detection at 220 nm and Waters Micromass.

EXAMPLE 20

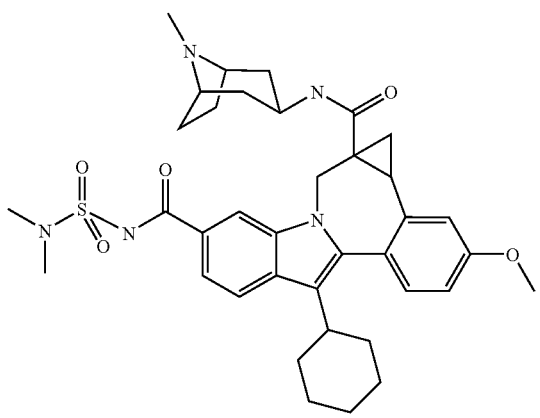

8-Cyclohexyl-N$^5$-(dimethylsulfamoyl)-11-methoxy-N$^{1a}$-(8-methyl-8-azabicyclo[3.2.1]oct-3-yl)-1,12b-dihydrocyclopropa[d]indolo[2,1-a][2]benzazepine-1a,5(2H)-dicarboxamide. 8-Cyclohexyl-N$^5$-(dimethylsulfamoyl)-11-methoxy-N$^{1a}$-(8-methyl-8-azabicyclo[3.2.1]oct-3-yl)-1,12b-dihydrocyclopropa[d]indolo[2,1-a][2]benzazepine-1a,5(2H)-dicarboxamide was prepared as a trifluoroacetic acid salt from coupling the acid, 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid, to 8-methyl-8-azabicyclo[3.2.1]octan-3-amine dihydrochloride using N,N,N',N'-tetramethyluronium tetrafluoroborate (TBTU) and N,N-diisopropylethylamine in DMF at r.t. under N$_2$. Analytical HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=674.66, HPLC R$_t$=1.712 min. Analytical HPLC method: Solvent A=5% MeCN—95% H$_2$O—10 mM NH$_4$OAc, Solvent B=95% MeCN—5% H$_2$O—10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=674.42, HPLC R$_t$=1.277 min.

EXAMPLE 21

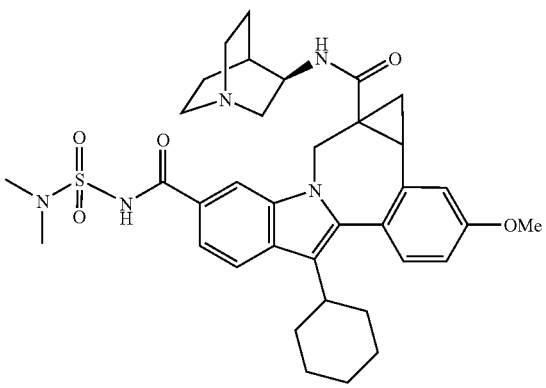

N$^{1a}$-((3R)-1-azabicyclo[2.2.2]oct-3-yl)-8-cyclohexyl-N$^5$-((dimethylamino)sulfonyl)-11-methoxy-1,12b-dihydrocyclopropa[d]indolo[2,1-a][2]benzazepine-1a,5(2H)-dicarboxamide. The product was prepared as a trifluoroacetic acid salt. Analytical HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=660.62, HPLC R$_t$=1.663 min. Analytical HPLC method: Solvent A=5% MeCN—95% H$_2$O—10 mM NH$_4$OAc, Solvent B=95% MeCN—5% H$_2$O—10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=660.35, HPLC R$_t$=1.253 min.

The general procedures below pertain to the experimental procedures that follow until noted. The acid (0.055 mmol, 1 eq.) was dissolved in dried DMF and followed by adding HATU (0.083 mmol, 1.5 eq.) and DIPEA(0.083. 1.5 eq.). The solution was stirred for 2 minutes and added into pre-weighted amine (0.083 mmol, 1.5 eq.) at room temperature. The mixture was stirred 14 h and purified by prep-HPLC. HPLC gradient methods: Method A: Column: Agilent SB CN4.6×100 mm 3.5 um; mobile phase: water, 10 mM NH$_4$OH, ACN; Method B: Column: Phenomenex Gemini 4.6×100 mm 5 um C18; mobile phase: water, 10 mM NH$_4$OH, ACN; Method C: Column: Waters x-Bidge C18 150×4.6 mm 5 micron; mobile phase: water, 10 mM NH$_4$OH, ACN; Method D: Column: Waters Xbridge 2.1×50 mm 5 um C18; mobile phase: water, 10 mM NH$_4$OH, ACN.

| Structure | HPLC retention time | HPLC purity | Mass | HPLC Method |
|---|---|---|---|---|
| 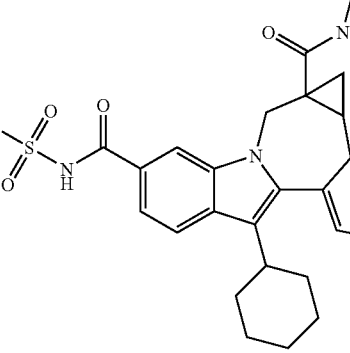 | 4.97 | 95.4 | 696.4 | Method A |
| 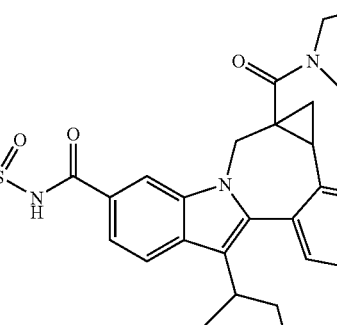 | 5.1 | 99 | 730.3 | Method A |
| 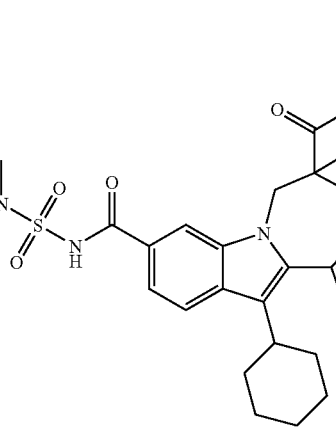 | 4.16 | 96.5 | 648.28 | Method A |

-continued

| Structure | HPLC retention time | HPLC purity | Mass | HPLC Method |
|---|---|---|---|---|
| 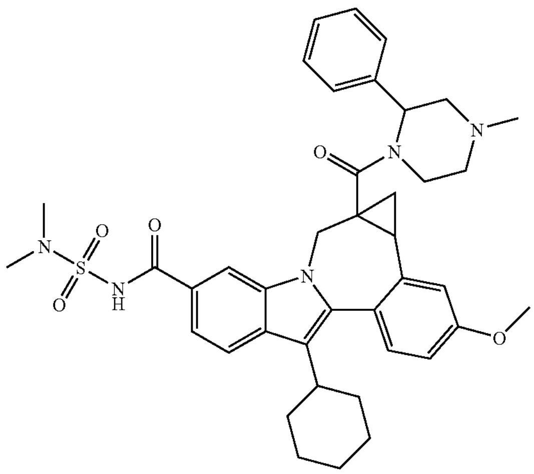 | 5.09 | 100 | 710.43 | Method A |
| 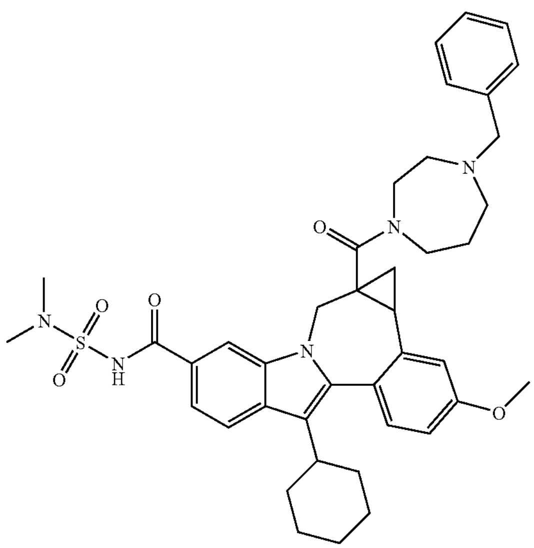 | 5.41 | 96.1 | 724.41 | Method A |
| 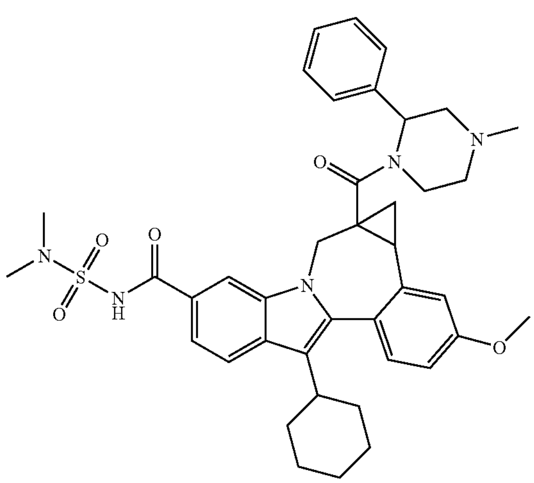 | 5.25 | 96.8 | 710.4 | Method A |

-continued

| Structure | HPLC retention time | HPLC purity | Mass | HPLC Method |
|---|---|---|---|---|
| 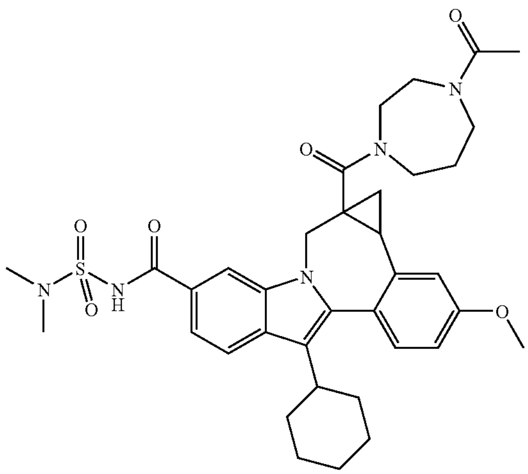 | 6.24 | 94.7 | 676.33 | Method B |
| 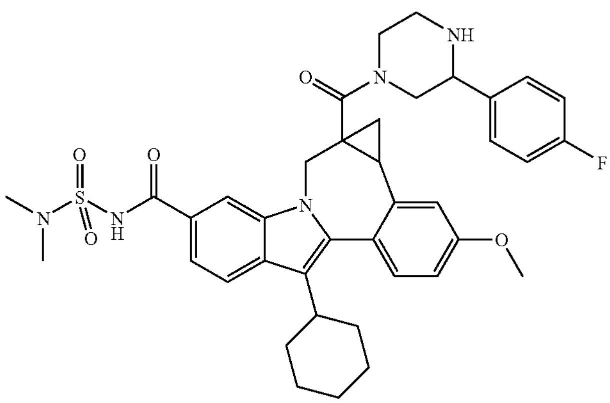 | 6.93 | 100 | 714.33 | Method B |
| 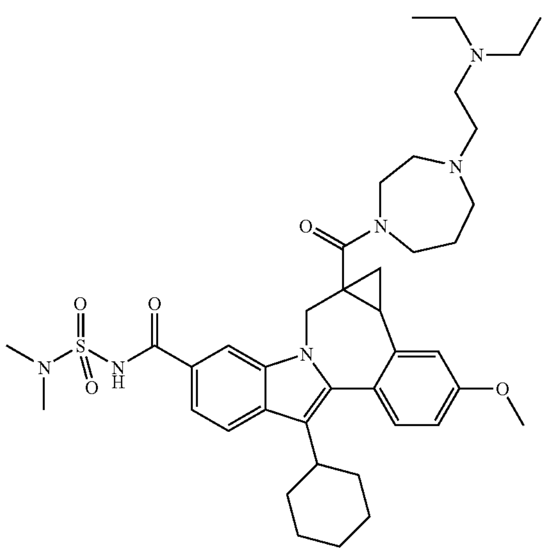 | 5.33 | 98.5 | 733.42 | Method B |

-continued

| Structure | HPLC retention time | HPLC purity | Mass | HPLC Method |
|---|---|---|---|---|
| 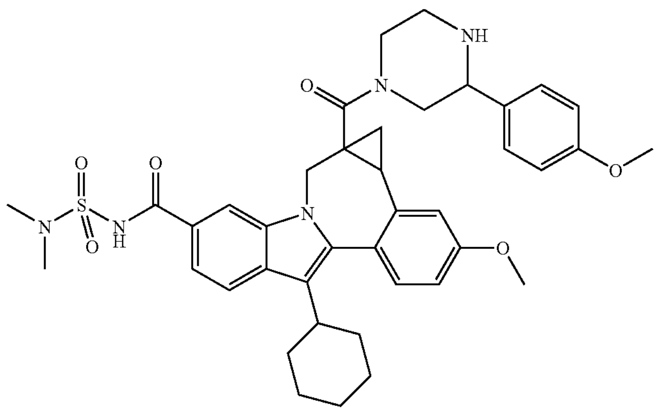 | 6.59 | 100 | 726.33 | Method B |
| 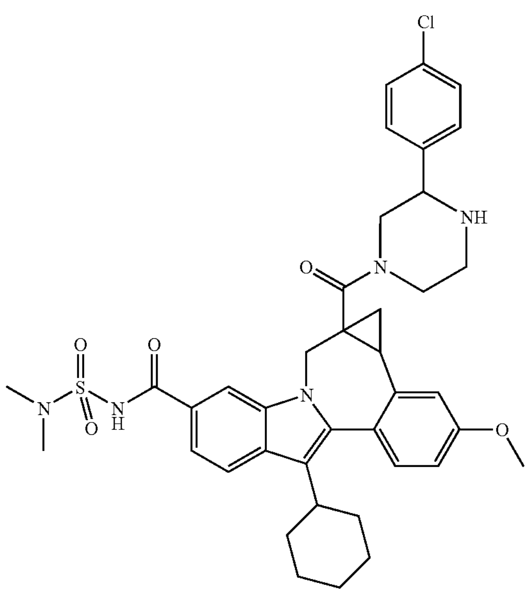 | 7.39 | 100 | 730.28 | Method B |
| 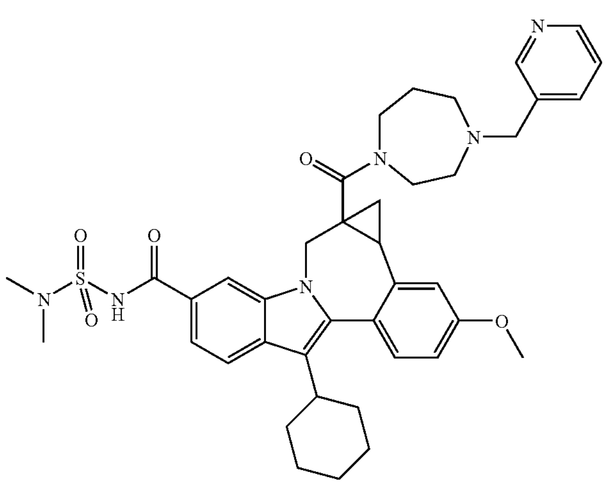 | 6.06 | 95.1 | 725.38 | Method B |

| Structure | HPLC retention time | HPLC purity | Mass | HPLC Method |
|---|---|---|---|---|
| 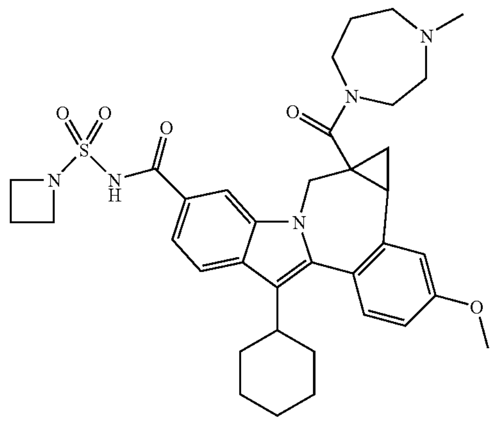 | 7.93 | 93.9 | 659.97 | Method C |
| 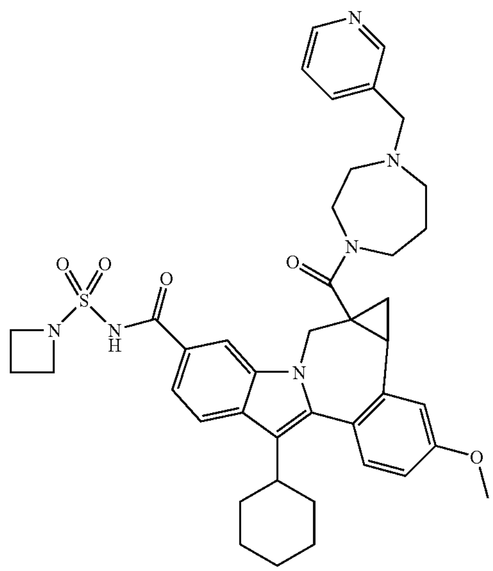 | 8.17 | 100 | 737.28 | Method C |
| 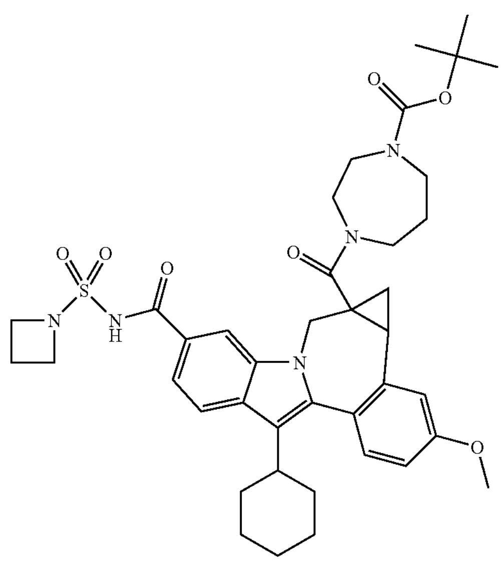 | 10.13 | 97.9 | 746.29 | Method C |

-continued

| Structure | HPLC retention time | HPLC purity | Mass | HPLC Method |
|---|---|---|---|---|
| 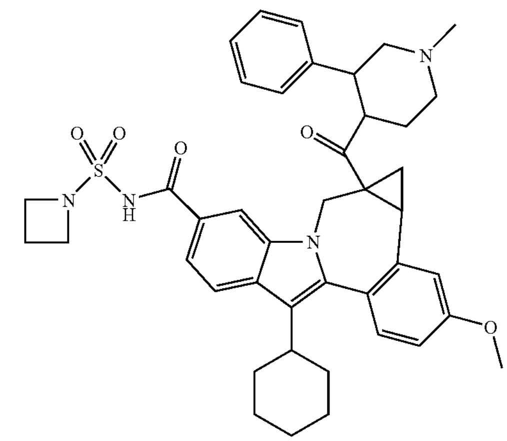 | 9.83 | 97.1 | 722.3 | Method C |
| 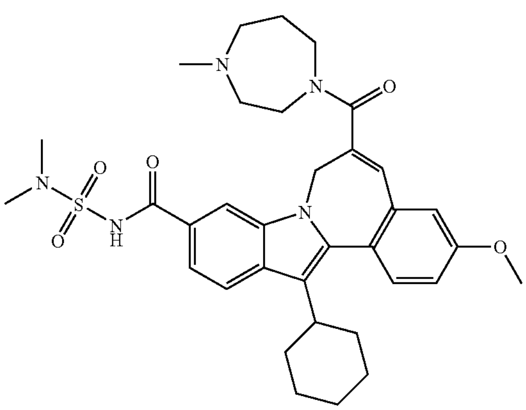 | 2.45 | 96.2 | 634.77 | Method D |
| 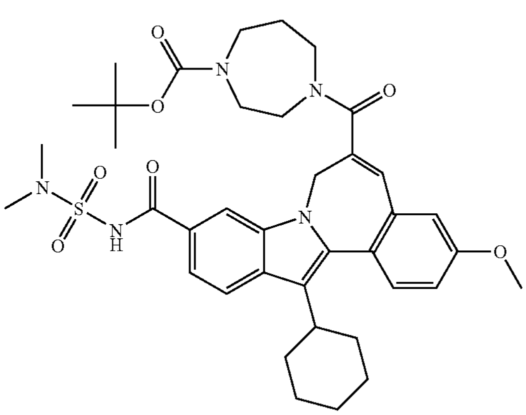 | 3.38 | 96.2 | 720.61 | Method D |

-continued
| Structure | HPLC retention time | HPLC purity | Mass | HPLC Method |
|---|---|---|---|---|
| 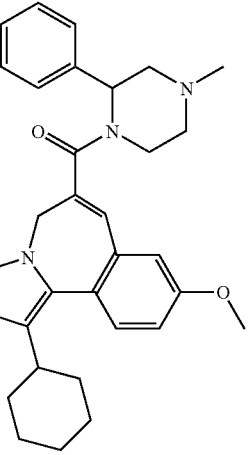 | 3.3 | 100 | 696.61 | Method D |
| 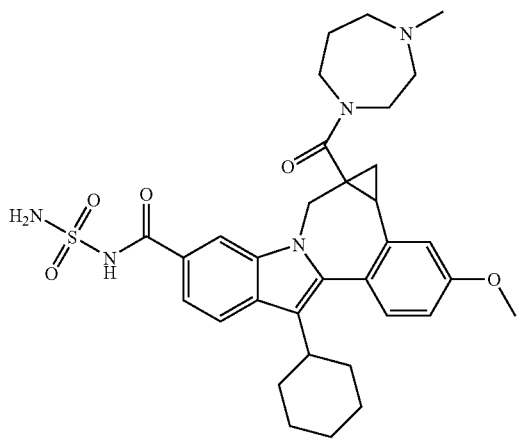 | 2.04 | 96.3 | 619.84 | Method D |
| 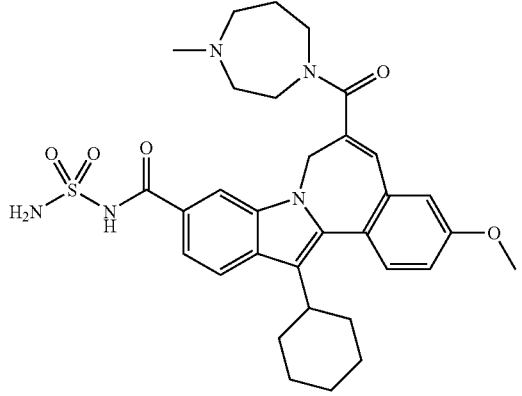 | 7.11 | 100 | 606.14 | Method D |

-continued

| Structure | HPLC retention time | HPLC purity | Mass | HPLC Method |
|---|---|---|---|---|
| 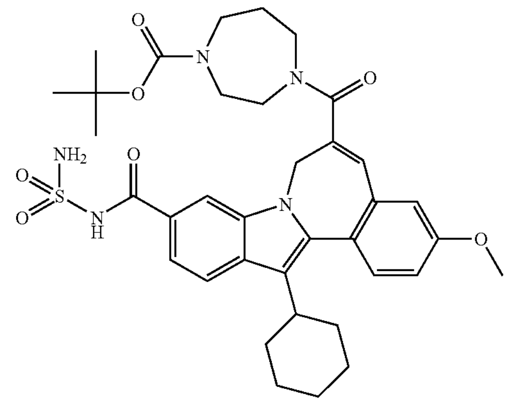 | 9.33 | 96.4 | 692.11 | Method D |
| 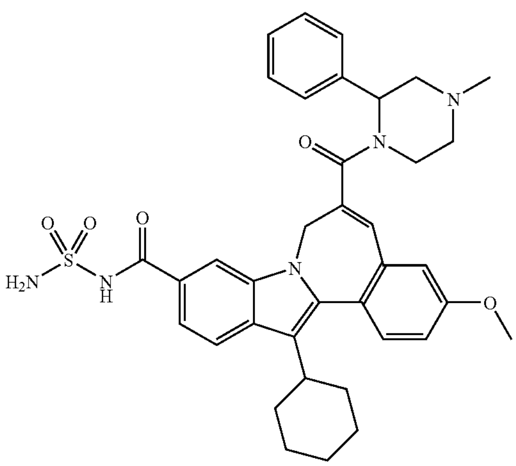 | 9.07 | 93.8 | 668.15 | Method D |
| 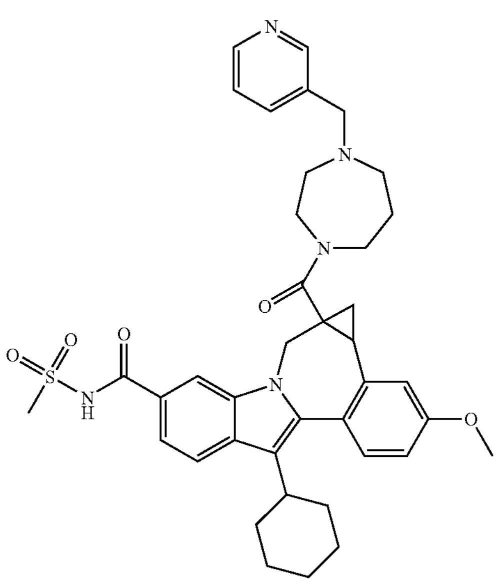 | 2.12 | 93.1 | 696.42 | Method D |

-continued
| Structure | HPLC retention time | HPLC purity | Mass | HPLC Method |
|---|---|---|---|---|
| 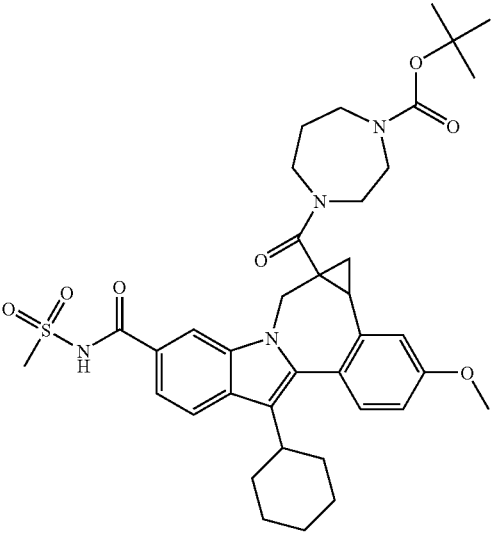 | 2.54 | 100 | 705.44 | Method D |
| 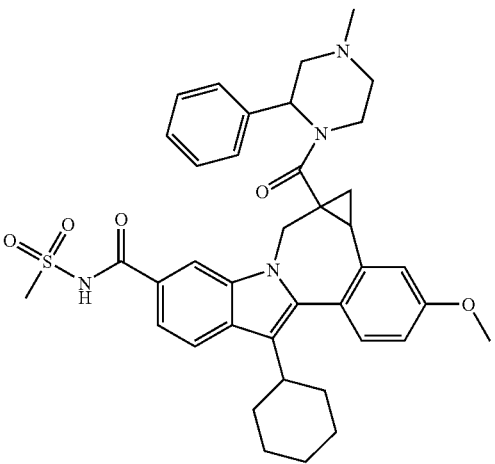 | 2.54 | 100 | 681.41 | Method D |
| 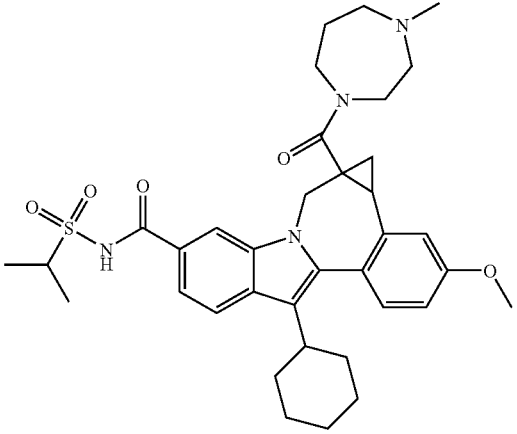 | 7.48 | 100 | 647.21 | Method D |

-continued

| Structure | HPLC retention time | HPLC purity | Mass | HPLC Method |
|---|---|---|---|---|
| 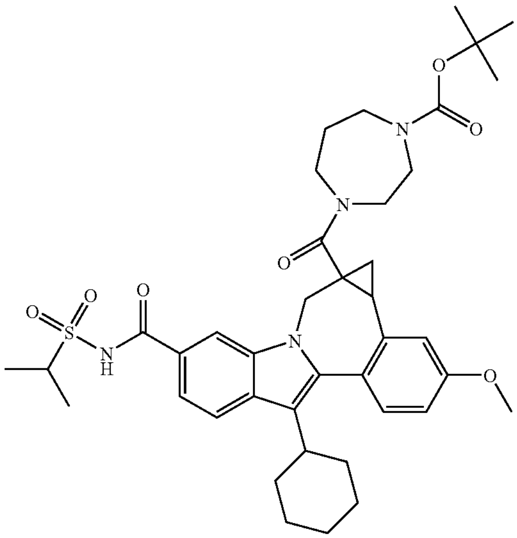 | 7.18 | 100 | 733.23 | Method D |
| 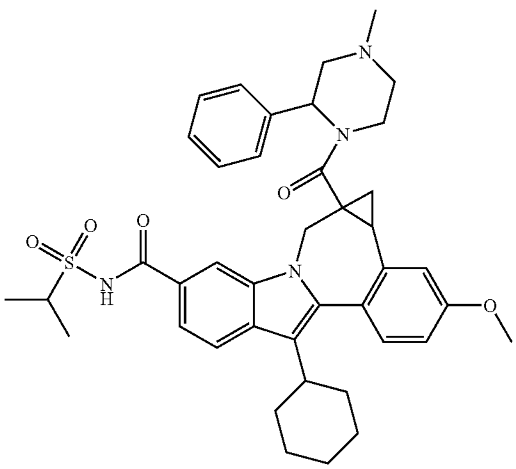 | 6.99 | 100 | 709.22 | Method D |
| 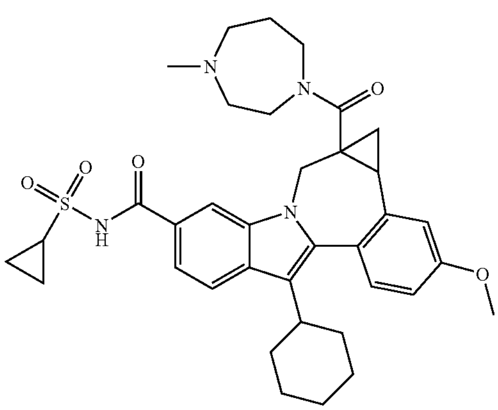 | 2.13 | 100 | 645.37 | Method D |

-continued

| Structure | HPLC retention time | HPLC purity | Mass | HPLC Method |
|---|---|---|---|---|
| 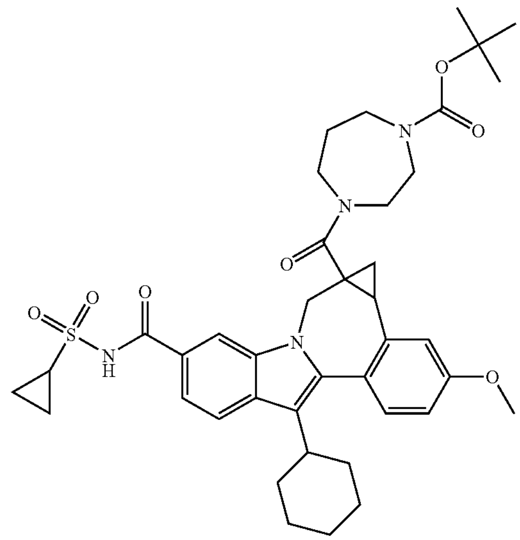 | 3.02 | 100 | 731.41 | Method D |
| 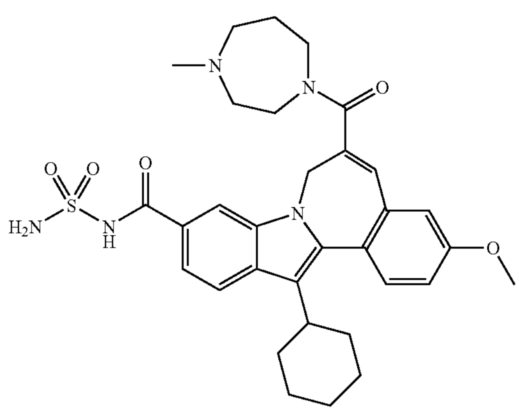 | 2.17 | 100 | 630.79 | Method D |
| 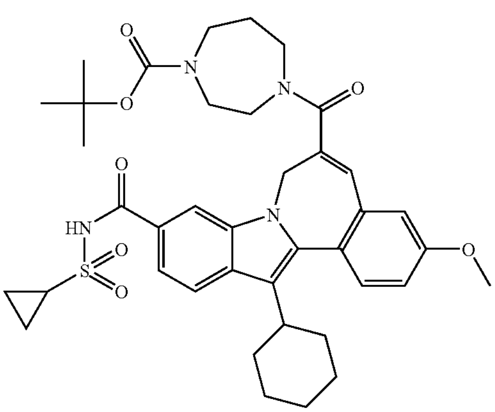 | 3.03 | 100 | 716.66 | Method D |

| Structure | HPLC retention time | HPLC purity | Mass | HPLC Method |
|---|---|---|---|---|
| 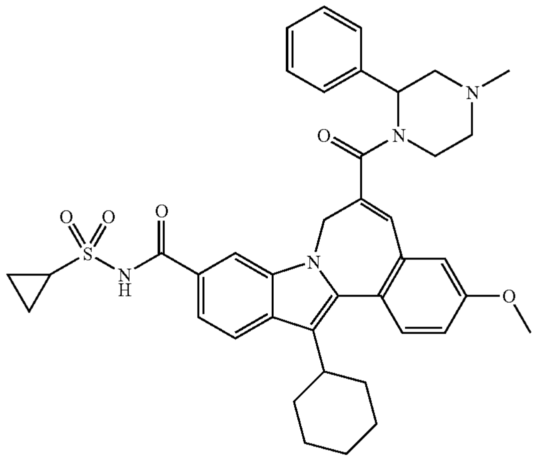 | 3.28 | 90.4 | 692.67 | Method D |
| 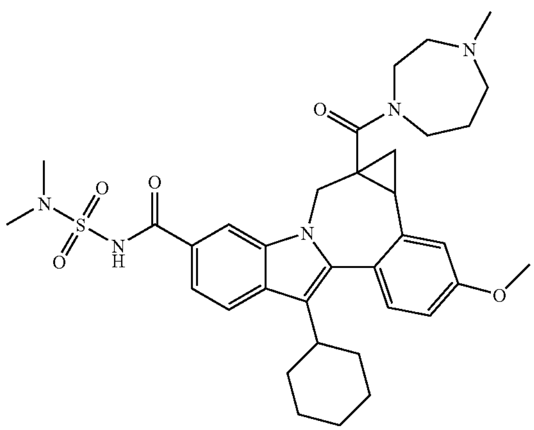 | 2.19 | 100.0 | 648.39 | Method D |
| 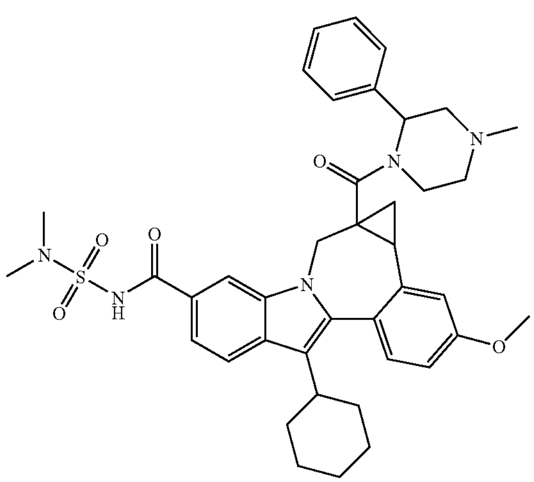 | 2.97 | 95.3 | 710.43 | Method D |

| Structure | HPLC retention time | HPLC purity | Mass | HPLC Method |
|---|---|---|---|---|
| 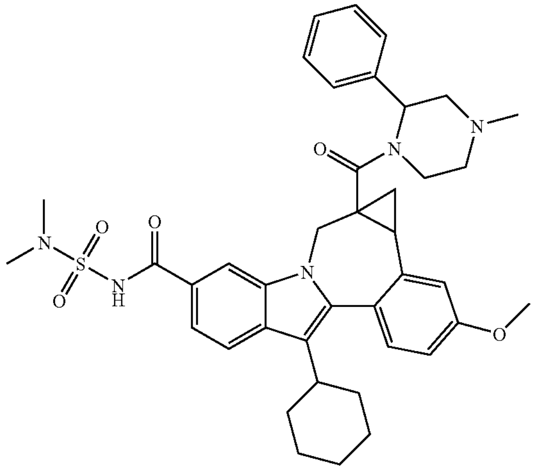 | 3.19 | 96.2 | 710.42 | Method D |

To a 250 mL RBF equipped with a stir bar was added bromocyclobutane (3.49 mL, 37.0 mmol) and 70 mL of diethyl ether. The flask was cooled to −78° C. (acetone/dry ice bath). To this solution was then added, via syringe, 2.0 eq. of a 1.7M solution of tert-butyllithium (43.6 mL, 74.1 mmol). The mixture was stirred for 60 minutes, then cannulated into a 500 mL flask containing sulfuryl chloride (6.00 mL, 74.1 mmol) in 30 mL of diethylether at −78° C. The suspension was warmed to room temperature overnight. The white mixture was diluted with 40 mL of diethylether, filtered and set aside. A 3 necked 500 mL RBF equipped with a stir bar and dry THF (10 mL) was cooled to −65° C. with the aid of a dry ice/isopropanol bath and gaseous ammonia was slowly sparged into the flask. Previously synthesized cyclobutanesulfonyl chloride (5.2 g, 33.6 mmol) was then dripped in via syringe (crude mixture in ~200 mL of ether/THF). Sparging of ammonia gas was continued for an additional 5 minutes. The mixture was kept at −65° C. for 4 hours then allowed to slowly warm to room temperature. The reaction mixture was filtered and washed with 100 mL of THF. The solvent was evaporated to give 2.1 g of the desired sulfonamide (46% yield) as a pale yellow oily solid. $^1$H NMR (500 MHz, DMSO-D6): δ ppm 1.81-1.89 (m, 2 H), 2.16-2.22 (m, 2 H), 2.23-2.31 (m, 2 H), 3.66-3.74 (m, 1 H), 6.68 (s, 2 H).

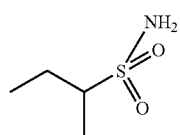

$^1$H NMR (500 MHz, DMSO-D6): δ ppm 0.94 (m, 3 H), 1.20 (m, 3 H), 1.30-1.45 (m, 1 H), 1.90 (m, 1 H), 2.76 (m, 1H), 6.59 (s, 2 H).

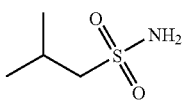

$^1$H NMR (500 MHz, DMSO-D6): δ ppm 1.02 (d, J=6.95 Hz, 6 H), 2.11 (m, 1 H), 2.86 (d, J=6.22 Hz, 2 H), 6.71 (s, 2 H).

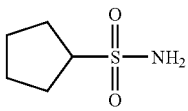

$^1$H NMR (500 MHz, DMSO-D6): δ ppm 1.51-1.66 (m, 4 H), 1.86 (m, 4 H), 3.37 (m, 1 H), 6.65 (s, 2 H).

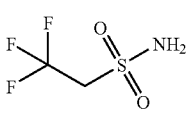

$^1$H NMR (500 MHz, DMSO-D6): δ ppm 4.24 (m, 2 H), 7.46 (s, 2 H).

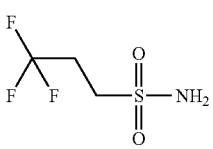

¹H NMR (500 MHz, DMSO-D6): δ ppm 2.70 (m, 2H), 3.20 (m, 2 H), 7.01 (s, 2 H).

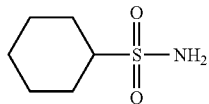

¹H NMR (500 MHz, DMSO-D6): δ ppm 1.07-1.17 (m, 1H), 1.22-1.38 (m, 4H), 1.62 (m, 1H), 1.78 (m, 2H), 2.05 (m, 2H), 2.68-2.77 (m, 1 H), 6.57 (s, 2 H).

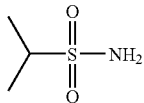

¹H NMR (300 MHz, DMSO-D6): δ ppm 1.22 (d, J=6.59 Hz, 6 H), 3.00 (m, 1 H), 6.59 (s, 2 H).

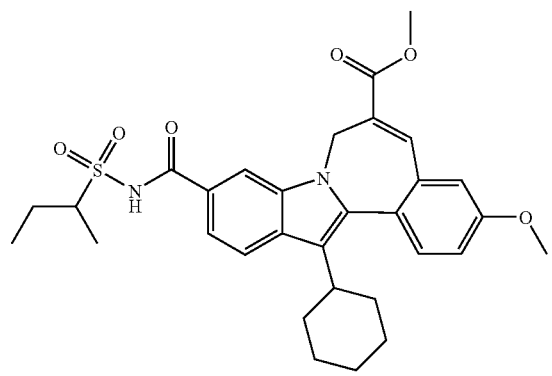

Methyl 10-((sec-butylsulfonyl)carbamoyl)-13-cyclohexyl-3-methoxy-7H-indolo[2,1-a][2]benzazepine-6-carboxylate. In a 100 mL round-bottomed flask (RBF) was added carboxylic acid 1 (575 mg, 1.291 mmol) and 1,1'-carbonyldiimidazole (460 mg, 2.84 mmol) in THF (15 mL) to give a yellow solution. The mixture was stirred at room temperature under nitrogen for 1 hour then heated to 70° C., in an oil bath, for 90 minutes. The mixture was cooled and sec-butyl sulfonamide (921 mg, 6.71 mmol) in 4 mL of THF was added along with neat DBU (0.389 mL, 2.58 mmol). The RBF was returned to the oil bath and heated overnight at 70° C. The reaction mixture was transferred to a separatory funnel, diluted with 100 mL of DCM, washed ×3 with 100 mL of 0.5 M HCl, then with 100 mL of H₂O, and finally saturated NaCl. The organic mixture was dried over MgSO4, filtered and concentrated to give 713 mgs of the desired acylsulfonamide 2 as a yellow solid (96% yield) which was placed under vacuum overnight. LC data was recorded on a Shimadzu LC-10AS liquid chromatograph equipped with a Phenomenex-Luna 10μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. 1H NMR (500 MHz, CD3OD): δ ppm 0.84-0.92 (m, 3 H), 1.03 (t, J=7.32 Hz, 3 H), 1.23 (m, 1 H), 1.28-1.44 (m, 7 H), 1.58 (m, 1 H), 1.72 (m, 2 H), 1.85 (m, 1 H), 1.95-2.07 (m, 3 H), 2.17 (m, 1 H), 2.78 (m, 1 H), 3.69 (m, 2 H), 3.83-3.91 (m, 3 H), 7.02 (s, 1 H), 7.11 (m, 1 H), 7.47 (d, J=7.63 Hz, 1 H), 7.74 (m, 3 H), 8.25 (s, 1 H.). LC/MS: m/z 565.22, Rf 2.192 min., 97.5% purity.

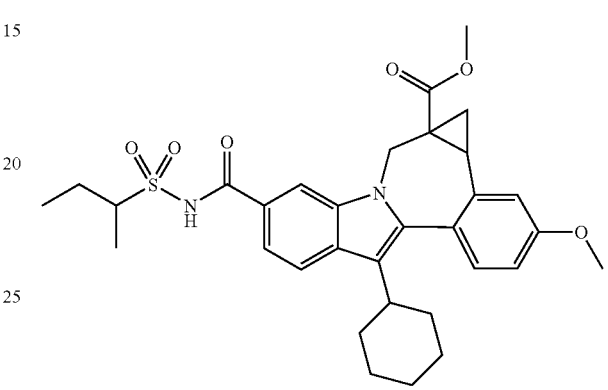

Methyl 5-((sec-butylsulfonyl)carbamoyl)-8-cyclohexyl-11-methoxy-1,12b-dihydro cyclopropa[d]indolo[2,1-a]d[2]benzazepine-1a(2H)-carboxylate. To 63.1 mgs of 95% NaH in 5 mL of dry DMF in a 100 mL RBF was added 629 mgs of trimethylsulfoxonium iodide at room temperature. The mixture was stirred at room temperature under nitrogen for 30 minutes. A solution of Intermediate 9 (in 7 mL of DMF) was added via syringe and the reaction was stirred for 15-20 minutes. The reaction mixture was quickly cooled to 0° C. with an ice bath, 1 mL of 1 M HCl was added followed by 60 mL of ice water. The heterogeneous mixture was stirred for 30 minutes. The mixture was filtered and the yellow solid was washed with ice water. The solid was taken up in 2% methanol/DCM and was purified using a Biotage Horizon MPLC employing a 40+M column with a solvent gradient of 2% methanol/DCM to 10% methanol/DCM. 450 mgs (62% yield) of the compound was obtained as a yellow solid after solvent evaporation. LC data was recorded on a Shimadzu LC-10AS liquid chromatograph equipped with a Phenomenex-Luna 10μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. 1H NMR (300 MHz, CD3OD): δ ppm 0.19 (m, 0.35 H), 1.03-1.14 (m, 3 H), 1.19-1.34 (m, 2.65 H), 1.43 (m, 5 H), 1.55-1.66 (m, 2 H), 1.74 (m, 2 H), 1.89-1.94 (m, 2 H), 1.99-2.14 (m, 3 H), 2.64-2.95 (m, 2 H), 3.35 (d, J=15.00 Hz, 0.65 H), 3.48 (m, 2 H), 3.67-3.81 (m, 2 H), 3.85 (s, 3 H), 3.90-3.98 (m, 0.35 H), 5.17 (m, 0.35 H), 5.36 (m, 0.65 H), 6.91-6.98 (m, 1 H), 7.09 (m, 0.35 H), 7.16 (m, 0.65 H), 7.19-7.27 (m, 1 H), 7.52-7.65 (m, 1 H), 7.83 (m, 1 H), 8.09 (s, 0.35 H), 8.29 (s, 0.65 H.). LC/MS: m/z 579.31, Rf 2.167 min., 95.2% purity.

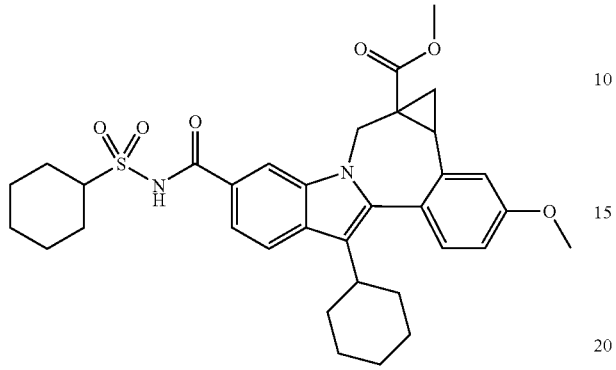

Methyl 8-cyclohexyl-5-((cyclohexylsulfonyl)carbamoyl)-11-methoxy-1,12b-dihydrocyclo propa[d]indolo[2,1-a][2]benzazepine-1a(2H)-carboxylate. 1H NMR (300 MHz, CD3OD): δ ppm 0.23 (m, 0.35 H), 1.14-1.53 (m, 10 H), 1.60-1.79 (m, 3 H), 1.91 (m, 3 H), 2.09 (m, 1.65 H), 2.18 (m, 3 H), 2.81-2.98 (m, 3 H), 3.41-3.46 (m, 0.65 H), 3.50 (m, 2 H), 3.71-3.79 (m, 2 H), 3.88 (s, 3 H), 3.99-4.04 (m, 0.35 H), 5.25 (m, 0.35 H), 5.45 (m, 0.65 H), 6.97-7.02 (m, 1 H), 7.13 (m, 0.35 H) 7.21 (m, 0.65 H), 7.26-7.32 (m, 1 H), 7.55-7.65 (m, 1 H), 7.85-7.92 (m, 1 H), 8.11 (s, 0.35 H), 8.32 (s, 0.65 H). LC/MS: m/z 605.42, Rf 2.223 min., 99.2% purity.

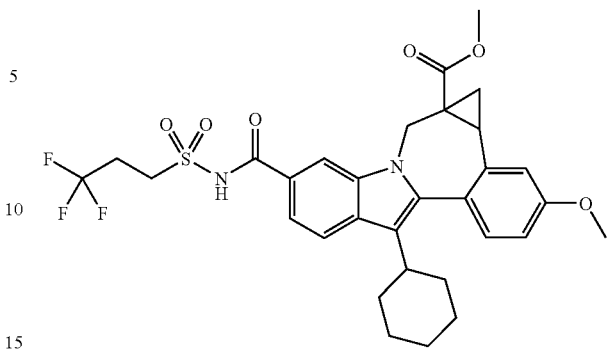

methyl 8-cyclohexyl-11-methoxy-5-(((3,3,3-trifluoropropyl)sulfonyl)carbamoyl)-1,12b-dihydrocyclopropa[d]indolo[2,1-a][2]benzazepine-1a(2H)-carboxylate. 1H NMR (300 MHz, CD3OD): δ ppm 0.19 (m, 0.35 H), 1.25 (m, 1.65 H), 1.41 (m, 2 H), 1.65 (m, 1 H), 1.76 (m, 2 H), 1.94 (m, 2 H), 2.04 (m, 1 H), 2.61-2.84 (m, 6 H), 2.88-2.96 (m, 1 H), 3.35-3.40 (m, 0.65 H), 3.48 (m, 2 H), 3.80 (m, 2 H), 3.86 (m, 3 H), 3.89-3.98 (m, 0.35 H), 5.18 (m, 0.35 H), 5.38 (m, 0.65 H), 6.96-7.01 (m, 1 H), 7.13 (m, 0.35 H), 7.20 (m, 0.65 H), 7.24-7.30 (m, 1 H), 7.58-7.69 (m, 1 H), 7.84-7.90 (m, 1 H), 8.13 (s, 0.35 H), 8.34 (s, 0.65 H.). LC/MS: m/z 619.32, Rf 2.188 min., 99.5% purity.

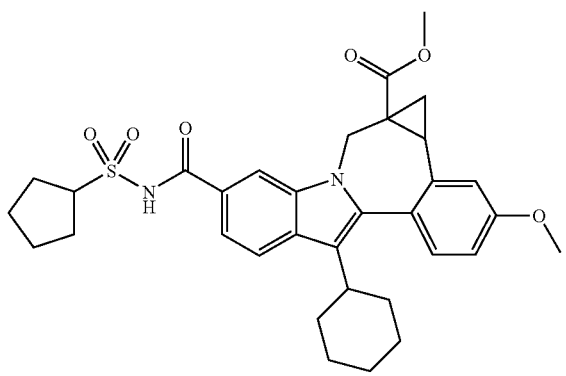

Methyl 8-cyclohexyl-5-((cyclopentylsulfonyl)carbamoyl)-11-methoxy-1,12b-dihydrocyclo propa[d]indolo[2,1-a][2]benzazepine-1a(2H)-carboxylate. 1H NMR (300 MHz, CD3OD): δ ppm 0.23 (m, 0.35 H), 1.27 (m, 2.65 H), 1.39 (m, 2 H), 1.60-1.79 (m, 7 H), 1.91-2.19 (m, 8 H), 2.67-2.97 (m, 2 H), 3.47 (m, 0.65 H), 3.50 (m, 3 H), 3.78-3.87 (m, 3 H), 4.10 (m, 0.35 H), 4.29 (m, 1 H), 5.22 (m, 0.35 H), 5.43 (m, 0.65 H), 6.98-7.02 (m, 1 H), 7.14 (m, 0.35 H), 7.21 (m, 0.65 H), 7.26-7.32 (m, 1 H), 7.55-7.65 (m, 1 H), 7.85-7.91 (m, 1 H), 8.10 (s, 0.35 H), 8.32 (s, 0.65 H). LC/MS: m/z 591.33, Rf 2.200 min., 100% purity.

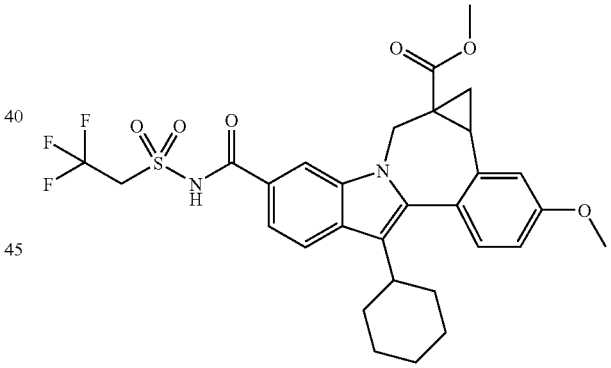

methyl 8-cyclohexyl-11-methoxy-5-(((2,2,2-trifluoroethyl)sulfonyl)carbamoyl)-1,12b-dihydro cyclopropa[d]indolo[2,1-a][2]benzazepine-1a(2H)-carboxylate. 1H NMR (300 MHz, CD3OD): δ ppm 0.13 (m, 0.35 H), 1.18 (m, 1.65 H), 1.38 (m, 2 H), 1.57-1.62 (m, 2 H), 1.73 (m, 2 H), 1.87 (m, 2 H), 1.96-2.05 (m, 1 H), 2.60-2.90 (m, 1.35 H), 3.17-3.22 (m, 0.65 H), 3.45 (m, 2 H), 3.74 (m, 1 H), 3.84 (m, 2 H), 4.04-4.10 (m, 3 H), 4.38-4.53 (m, 2 H), 5.06 (m, 0.35 H), 5.18 (m, 0.65 H), 6.90-6.96 (m, 1 H), 7.06 (m, 0.35 H), 7.13 (m, 0.65 H), 7.16-7.22 (m, 1 H), 7.63 (m, 0.65 H), 7.70-7.80 (m, 1.35 H), 8.14 (s, 0.35 H), 8.33 (s, 0.65 H.). LC/MS: m/z 605.29, Rf 2.178 min., 96.5% purity.

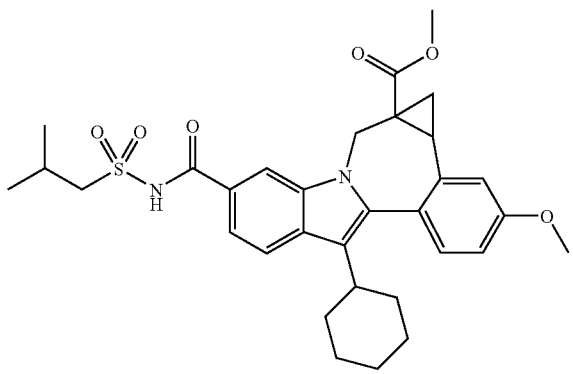

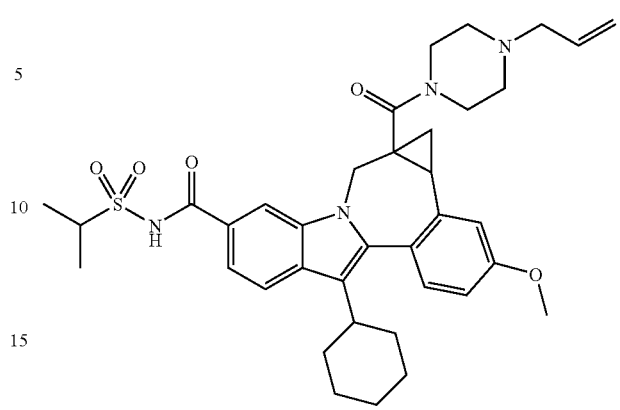

Methyl 8-cyclohexyl-5-((isobutylsulfonyl)carbamoyl)-11-methoxy-1,12b-dihydrocyclopropa[d]indolo[2,1-a][2]benzazepine-1a(2H)-carboxylate. 1H NMR (300 MHz, CD3OD): δ ppm 0.17 (m, 0.35 H), 1.09 (m, 6 H), 1.22 (m, 1.65 H), 1.38 (m, 2 H), 1.49-1.60 (m, 1 H), 1.73 (m, 2 H), 1.87 (m, 2 H), 1.96-2.05 (m, 2 H), 2.15-2.39 (m, 1 H), 2.61-2.87 (m, 2 H), 2.96 (d, J=6.22 Hz, 2 H), 3.19 (m, 2 H), 3.43 (m, 2 H), 3.70 (m, 2 H), 3.84 (m, 2 H), 5.06-5.11 (m, 1 H), 6.90-6.95 (m, 1 H), 7.05-7.11 (m, 1 H), 7.16-7.23 (m, 1 H), 7.67-782 (m, 2 H), 8.20 (s, 0.35 H), 8.39 (s, 0.65 H). LC/MS: m/z 579.30, Rf 2.190 min., 96.2% purity.

General procedure for the transformation of esters of formula I to corresponding amides. In a 100 mL round-bottomed flask was added 1 N sodium hydroxide (3 eq., 1.583 ml, 1.583 mmol) and bridged ester 1 (1 eq., 0.528 mmol) in methanol (4.00 ml) and THF (4.00 ml) to give a yellow solution. The mixture was stirred for 3 hours at room temperature. 3 equivalents of 1 N HCl was then added, the product diluted with ethyl acetate then extracted, washed with brine and dried over MgSO4. Filtration and subsequent evaporation of volatiles gave the carboxylic acids 2 in near quantitative yield. To a 0.10 mmol solution of carboxylic acid 2 in 1 mL of anhydrous N,N-Dimethylformamide (DMF) in a 2 dram vial equipped with a Teflon™ lined screw cap was added 0.3 mmol (3 eq.) of 2-(1H-Benzotriazole-1-yl)-1,1,3,3,-Tetramethyluronium Tetrafluoroborate (TBTU) in 1.0 mL of anhydrous DMF followed by the addition of 0.2 mmol (2 eq.) of amine 3 in 1.0 mL of anhydrous DMF and 0.4 mmol of neat N,N-diisopropylethylamine. The reaction was shaken on a VWR Vortex-Genie 2 Mixer overnight at room temperature. The reaction volumes were then reduced in a Savant Speedvac and the crude products were taken up in 1.2 mL of methanol and purified using a Shimadzu preparative HPLC employing methanol/water and 0.1% trifluoroacetic acid buffer with a Phenomenex Luna, C18, 30 mm×100 mm, 10 μm column at a gradient of 40-100% B and a flow rate of 40 mL/min. over 10 minutes with a 5-10 minute hold, to give carboxamides 4 as yellow amorphous solids (65%-70% yield). Post-purification LC/MS data was obtained on a Shimadzu analytical LC/Micromass Platform LC (ESI+) at 220 nm using the following set of conditions: Column I (Phenomenex 10 μm C18, 4.6×30 mm), Solvent system I (gradient of 0-100% B where B=90% HPLC grade methanol/0.1% trifluoroacetic acid/10% HPLC grade water), in 2 minutes with a 1 minute hold at a flow rate of 5 mL/minute.

(+/−)-8-cyclohexyl-N-(isopropylsulfonyl)-1,1a,2,12b-tetrahydro-11-methoxy-1a-(4-allylpiperazin-1-carbonyl)cycloprop[d]indolo[2,1-a][2]benzazepine-5-carboxamide. The product was purified by prep HPLC and isolated as a TFA salt. LC-MS retention time: 3.128 min; MS m/z (M+H) 659. The product was observed to exist as inter-converting rotamers by 1H NMR (400 MHz, METHANOL-d4) δ ppm 1.45 (11 H, m), 1.67 (1 H, m), 1.83 (2 H, m), 2.06 (4 H, m), 2.64 (1 H, dd, J=8.81, 5.79 Hz), 2.90-4.05 (10 H, m), 2.99 (1 H, m), 3.67 (1 H, d, J=15.61 Hz), 3.89 (3 H, s), 3.97 (1 H, m), 5.13 (1 H, d, J=15.36 Hz), 5.66 (3 H, m) 7.04 (1 H, dd, J=8.69, 2.64 Hz), 7.19 (1 H, d, J=2.52 Hz), 7.34 (1 H, d, J=8.56 Hz), 7.60 (1 H, d, J=8.56 Hz), 7.93 (1 H, d, J=8.56 Hz), 8.05 (1 H, s).

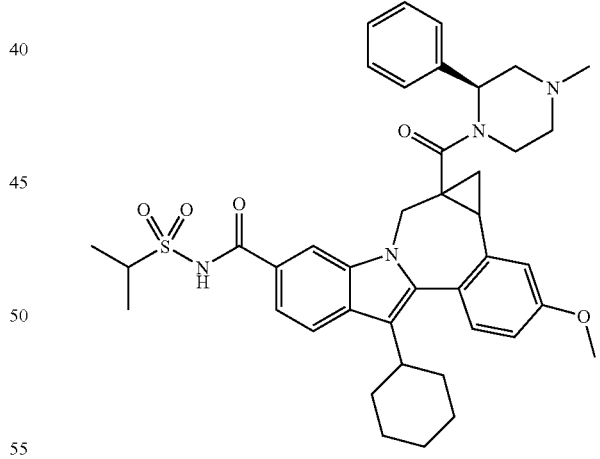

(+/−)-8-cyclohexyl-N-(isopropylsulfonyl)-1,1a,2,12b-tetrahydro-11-methoxy-1a-[(+)-4-methyl-2-phenylpylpiperazin-1-carbonyl]cycloprop[d]indolo[2,1-a][2]benzazepine-5-carboxamide. The product was prepared with (+)-1-methyl-3-phenylpiperazine. The product was purified by prep HPLC and isolated as TFA salt. LC-MS retention time: 3.210; MS m/z (M+H) 709. The product was observed to exist as inter-converting rotamers by 1H NMR.

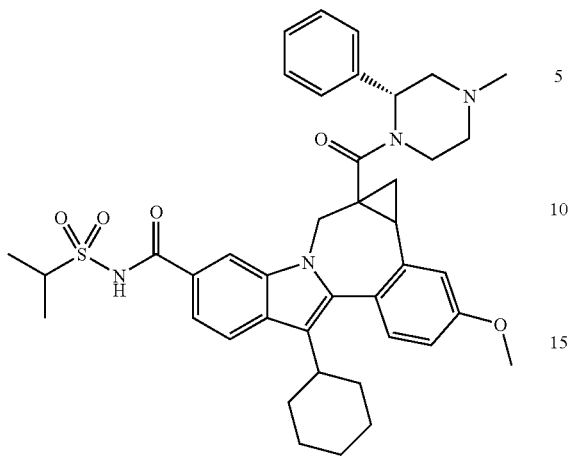

(+/−)-8-cyclohexyl-N-(isopropylsulfonyl)-1,1a,2,12b-tetrahydro-11-methoxy-1a-[(−)-4-methyl-2-phenylpylpiperazin-1-carbonyl]cycloprop[d]indolo[2,1-a][2]benzazepine-5-carboxamide. The product was prepared with (−)-1-methyl-3-phenylpiperazine. The product was purified by prep HPLC and isolated as TFA salt. LC-MS retention time: 3.201; MS m/z (M+H) 709. The product was observed to exist as inter-converting rotamers.

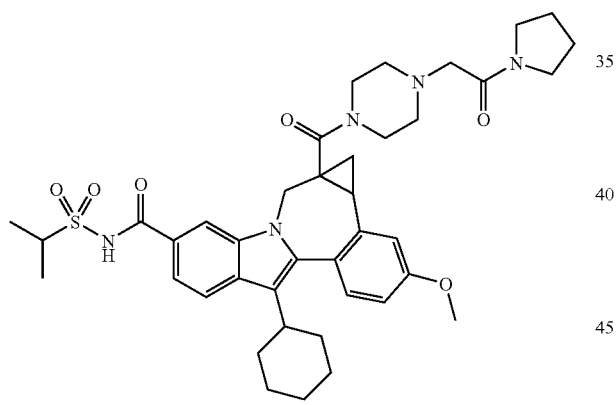

(+/−)-8-cyclohexyl-N-(isopropylsulfonyl)-1,1a,2,12b-tetrahydro-11-methoxy-1a-[4-(2-oxo-2-(pyrrolidin-1-yl)ethyl)piperazine-1-carbonyl]cycloprop[d]indolo[2,1-a][2]benzazepine-5-carboxamide. The product was purified by prep HPLC and isolated as TFA salt. LC-MS retention time: 3.145 min; MS m/z (M+H) 730. The product was observed to exist as inter-converting rotamers by 1H NMR (400 MHz, METHANOL-d$_4$) δ ppm 1.41 (11 H, m), 1.69 (1 H, m), 1.81 (2 H, br. s.), 2.04 (8 H, m), 2.62 (1 H, dd, J=9.07, 6.04 Hz), 2.98 (1 H, d, J=3.27 Hz), 3.48 (8 H, m), 3.66 (1 H, d, J=15.36 Hz), 3.89 (3 H, s), 3.95 (1 H, m), 4.21 (3 H, m), 5.14 (1 H, d, J=15.36 Hz), 7.03 (4 H, dd, J=8.31, 2.52 Hz), 7.19 (1 H, d, J=2.77 Hz), 7.33 (1 H, d, J=8.56 Hz), 7.59 (1 H, dd, J=8.31, 1.51 Hz), 7.92 (1 H, d, J=8.56 Hz), 8.08 (1 H, s).

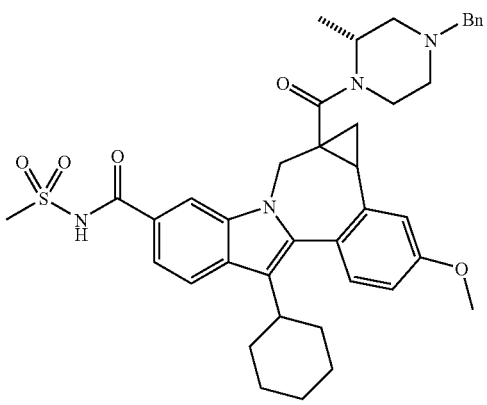

(+/−)-8-cyclohexyl-N-(methylsulfonyl)-1,1a,2,12b-tetrahydro-11-methoxy-1a-[(2R)-4-benzyl-2-methylpiperazine-1-carbonyl]cycloprop[d]indolo[2,1-a][2]benzazepine-5-carboxamide. The product was purified by prep HPLC and isolated as TFA salt. LC-MS retention time: 3.053 min; MS m/z 695 (M+H).

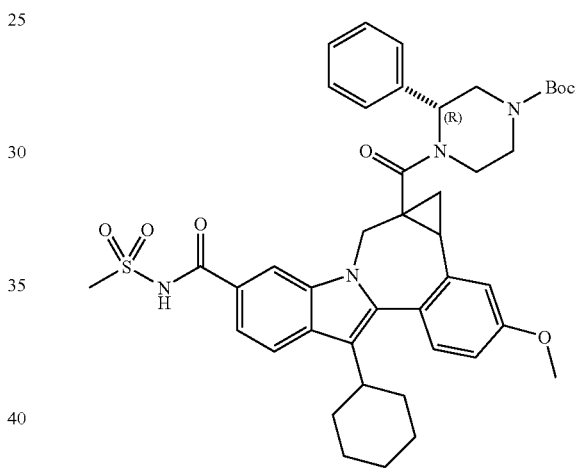

(+/−)-8-cyclohexyl-N-(methylsulfonyl)-1,1a,2,12b-tetrahydro-11-methoxy-1a-[(R)-4-(tert-butoxycarbonyl)-2-phenylpiperazine-1-carbonyl]cycloprop[d]indolo[2,1-a][2]benzazepine-5-carboxamide. The product was purified by Prep HPLC. LC-MS retention time: 3.610 min; MS mnz (M+H-Boc) 667.

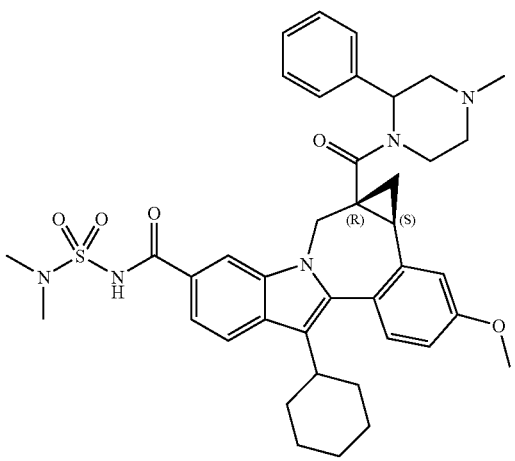

(+/−)-8-cyclohexyl-N-(N,N-dimethylsulfamoyl)-1,1a,2,12b-tetrahydro-11-methoxy-1a-[(+)-4-methyl-2-phenylpiperazine-1-carbonyl]cycloprop[d]indolo[2,1-a][2]benzazepine-5-carboxamide. The product was purified by prep HPLC and isolated as TFA salt. LC-MS retention time 3.183 min; MS m/z (M+H) 710.

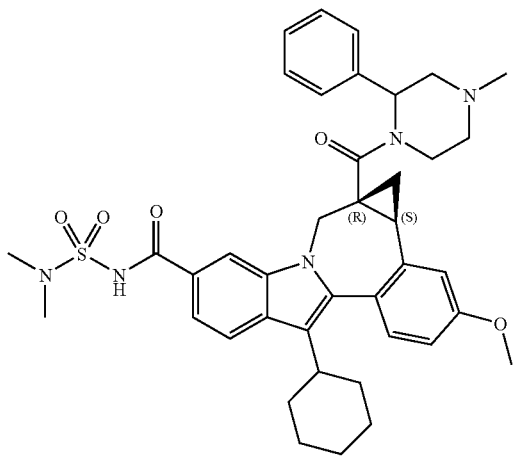

(+/−)-8-cyclohexyl-N-(N,N-dimethylsulfamoyl)-1,1a,2,12b-tetrahydro-11-methoxy-1a-[(−)-4-methyl-2-phenylpiperazine-1-carbonyl]cycloprop[d]indolo[2,1-a][2]benzazepine-5-carboxamide. The product was purified and isolated as TFA salt. LC-MS retention time 3.156 min; MS m/z (M+H) 710.

The following compounds were analyzed by following LCMS methods until noted: LCMS method 1: Start % B: 0, Final % B: 100; Gradient time: 3 min; Stop time: 4 min; Flow rate: 4 ml/min; Wavelenth: 220; Solvent A: 10% MeOH/90% $H_2O$/0.1% Trifluoroacetic Acid; Solvent B: 10% $H_2O$/90% MeOH/0.1% Trifluoroacetic Acid; Column: XBridge 4.6×50 mm S5. LCMS method 2: Start % B: 0, Final % B: 100; Gradient time: 3 min; Stop time: 5 min; Flow rate: 4 ml/min; Wavelength: 220; Solvent A: 10% MeOH/90% $H_2O$/0.1% Trifluoroacetic Acid; Solvent B: 10% $H_2O$/90% MeOH/0.1% Trifluoroacetic Acid; Column: XBridge 4.6×50 mm S5.

tetrahydro-2H-pyran-4-sulfonamide. A mixrue of 4-chlorotetrahydro-2H-pyran (1 g, 8.29 mmol) and potassium ethanethioate (0.947 g, 8.29 mmol) in DMF (15 mL) was stirred at 80° C. for 24 h. The reaction mixture was cooled down and partitioned between hexane and cold 1N Na OH. The organic layer was washed with brine, dried (MgSO4), removed the solvent to afford S-tetrahydro-2H-pyran-4-yl ethanethioate as a pale brown oil. 1H NMR (400 MHz, CHLOROFORM-d) δ ppm 1.68 (2 H, m), 1.90 (2 H, m), 2.32 (3 H, s), 3.55 (2 H, m), 3.68 (1 H, m), 3.91 (2 H, dt, J=11.83, 3.90 Hz). Into a solution of S-tetrahydro-2H-pyran-4-yl ethanethioate in DCm (3 mL) and water (3 mL) at −10° C., chlorine gas was bubbled for ~5 min slowly until persistent greenish color was maintained. The mixture was stirred for 0.5 h at r.t. and blown with air for 5 min and diluted with ether (5 mL). The mixture was added to concentrated ammonium hydroxide (5mL, 128 mmol) at 0° C. over 10 min. The mixture was stirred for 1 h and evaporated to dryness. The residue was taken up with EtOAc and filtered through 2" silica gel pad and eluted with EtOAc/hexane (80% to 100%) to afford tetrahydro-2H-pyran-4-sulfonamide as a brown solid (113 mg). 1H NMR (400 MHz, CHLOROFORM-d) δ ppm 1.88 (2 H, m), 2.08 (2 H, ddd, J=12.72, 3.65, 1.76 Hz), 3.15 (1 H, tt, J=12.06, 3.81 Hz), 3.40 (2 H, td, J=11.96, 2.27 Hz), 4.11 (2 H, dd, J=11.33, 4.28 Hz), 4.48 (2 H, br. s.).

isoxazolidine-2-sulfonamide. To a cold (0° C.) solution of chlorosulfonyl isocyanate (0.437 mL, 5.02 mmol) in CH2Cl2 (10 mL) was added tert-BuOH (0.480 mL, 5.02 mmol) and the mixture was stirred for 1 h at 0° C. Then HCl salt of isoxazolidine (0.5 g, 4.56 mmol) and TEA (1.399 mL, 10.04 mmol) were added consecutively and the mixture was stirred overnight. Rxn was diluted with EtOAc and washed with ice cold 1N HCl, brine and then dried (MgSO4). Isolated crude product was purified by Biotage 25M column to afford tert-butyl isoxazolidin-2-ylsulfonylcarbamate as a beige solid (0.82 g, 71%). 1H NMR (400 MHz, CHLOROFORM-d) δ ppm 1.50 (9 H, s), 2.38 (2 H, quin, J=7.37 Hz), 3.81 (2 H, m), 4.19 (2 H, t, J=7.30 Hz). To a cold (0-5° C.) solution of tert-butyl isoxazolidin-2-ylsulfonylcarbamate (0.82 g, 3.25 mmol) in DCM (2 mL) was added TFA (2 mL, 35.1 mmol) and the reaction mixture was stirred for 2 h at r.t and removed the solvent to afford isoxazolidine-2-sulfonamide (0.229 g, 46%). 1H NMR (500 MHz, CHLOROFORM-d) δ ppm 2.40 (2 H, quin, J=7.32 Hz), 3.65 (2 H, m), 4.20 (2 H, t, J=7.32 Hz), 4.83 (2 H, brs).

1-methylpiperidine-4-sulfonamide. To a suspension of magnesium (0.426 g, 17.51 mmol) in THF (50 mL) was added 1,2-dibromoethane (0.058 mL, 0.674 mmol) and stirred for 10 min and then 4-chloro-1-methylpiperidine (1.8 g, 13.47 mmol) in THF (4 mL) was added and the mixture was refluxed under nitrogen overnight. Cooled solution of the (1-methylpiperidin-4-yl)magnesium chloride was canulated into a cold (−78° C.) solution of sulfuryl chloride (1.3 mL, 16 mmol) in THF (10 mL). The mixture was stirred at 0° C. for 1.5 h and cooled to −78° C. and bubbled ammonia gas for 10 min and stirred at −78° C. for 10 min and allowed to warm to r.t. maintained under balloon pressure of NH3 for 2 h. Diluted with 100 mL ether, filtered off the solids and the filtrate was concentrated to afford a brown solid. Brown solid in THF was stirred with K2CO3 for 1h and filtered and concentrated to afford 1-methylpiperidine-4-sulfonamide as a beige solid. 1H NMR (500 MHz, DMSO-$d_6$) δ ppm 1.59 (2 H, m), 1.84 (2 H, m), 1.93 (2 H, m), 2.15 (3 H, s), 2.71 (1 H, ddd, J=12.13, 8.32, 3.66 Hz), 2.84 (2 H, m), 6.69 (2 H, brs).

The following table shows compounds that were prepared using similar chemistry to those described above and that were characterized using the following methods. Purification Method: Dionex LC; Chromeleon 6.70 sp1 LC software; HP 1100 quarternary pump for analytical; Varian prostar binary pump with 50 mL/min head for prep; Dionex UVD340U UV spectrometer; Sedex 75 ELS detector; Thermo-Finnigen MSQ Surveyor Plus mass spectrometer. LC Conditions: Column: Phenomenex Gemini 21.2×250 mm 5 um C18; Mobile Phase; A=Water; B=ACN; Modifier=0.1% TFA in A. Final Analysis Method: MassLynx 4.0 SP4 LC-MS software; CTC-Leap HTS-PAL autosampler; Agilent 1100 binary pump; Agilent 1100 photodiode array; Polymer Lab 2100 ELS detector (Evap. Temp.=45° C., Neb. Temp.=35° C.); Waters ZQ with ESCi mass spectrometer. LC Conditions: Column: Suppelco Ascentis C18 4.6×50 mm 2.7 micron; Mobile Phase: A=Water, 10 mM NH4OAc; B=CAN.

| Compound | Purity | Rt (min) |
|---|---|---|
| 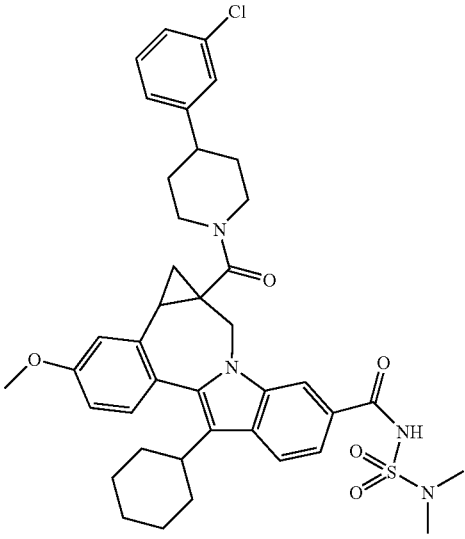<br>cycloprop[d]indolo[2,1-a][2]benzazepine-5-carboxamide, 1a-[[4-(3-chlorophenyl)-1-piperidinyl]carbonyl]-8-cyclohexyl-N-[(dimethylamino)sulfonyl]-1,1a,2,12b-tetrahydro-11-methoxy- | 97.4 | 4.12 |
| 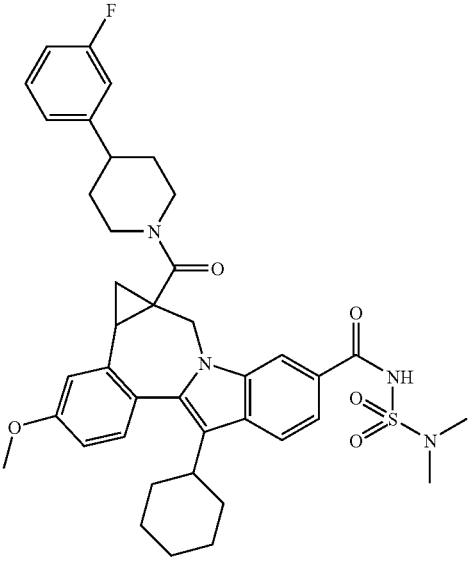<br>cycloprop[d]indolo[2,1-a][2]benzazepine-5-carboxamide, 8-cyclohexyl-N-[(dimethylamino)sulfonyl]-1a-[[4-(3-fluorophenyl)-1-piperidinyl]carbonyl]-1,1a,2,12b-tetrahydro-11-methoxy- | 95 | 3.92 |

-continued

| Compound | Purity | Rt (min) |
|---|---|---|
| 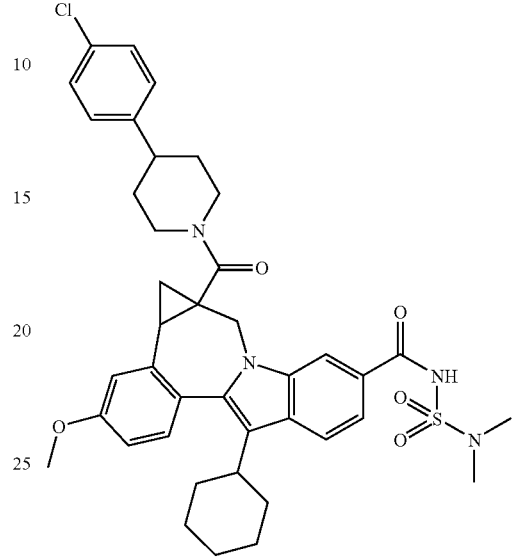<br>cycloprop[d]indolo[2,1-a][2]benzazepine-5-carboxamide, 1a-[[4-(4-chlorophenyl)-1-piperidinyl]carbonyl]-8-cyclohexyl-N-[(dimethylamino)sulfonyl]-1,1a,2,12b-tetrahydro-11-methoxy- | 95 | 4.14 |
| 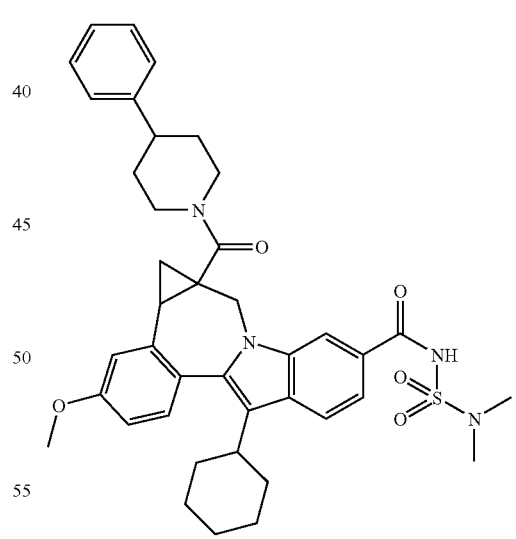<br>cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(4-phenyl-1-piperidinyl)carbonyl] | 95 | 3.91 |

-continued

| Compound | Purity | Rt (min) |
|---|---|---|
| 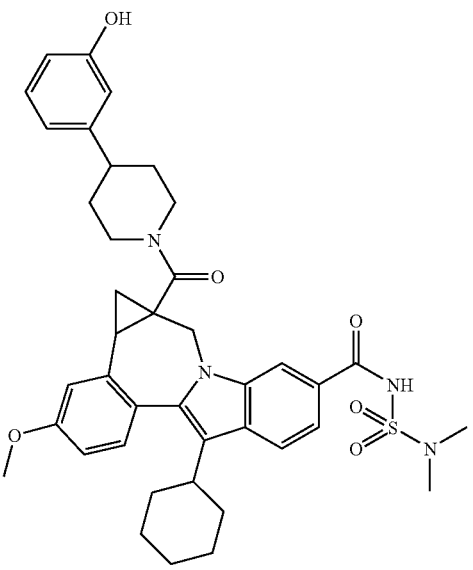 cycloprop[d]indolo[2,1-a][2]benzazepine-5-carboxamide, 8-cyclohexyl-N-[(dimethylamino)sulfonyl]-1,1a,2,12b-tetrahydro-1a-[[4-(3-hydroxyphenyl)-1-piperidinyl]carbonyl]-11-methoxy- | 95 | 3.27 |
| 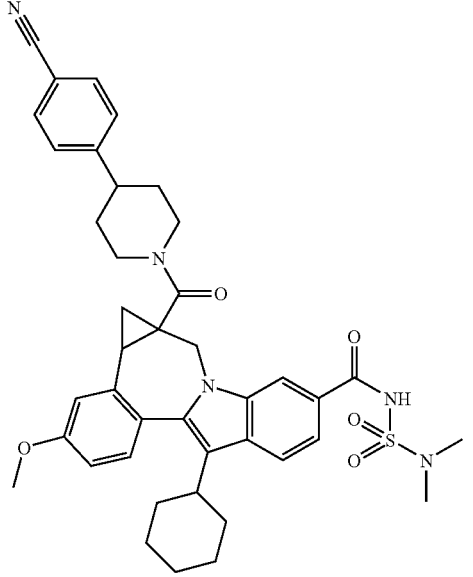 cycloprop[d]indolo[2,1-a][2]benzazepine-5-carboxamide, 1a-[[4-(4-cyanophenyl)-1-piperidinyl]carbonyl]-8-cyclohexyl-N-[(dimethylamino)sulfonyl]-1,1a,2,12b-tetrahydro-11-methoxy | 95 | 3.63 |

-continued

| Compound | Purity | Rt (min) |
|---|---|---|
| 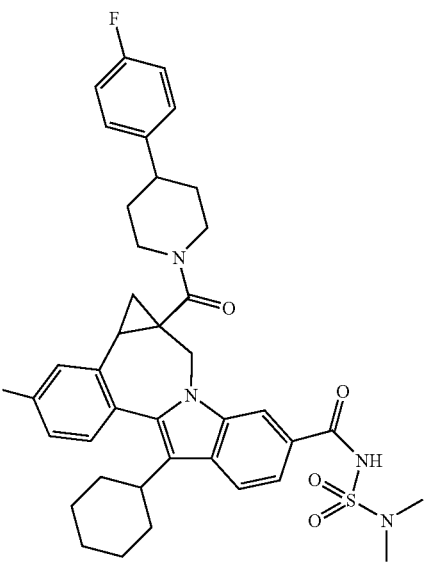 cycloprop[d]indolo[2,1-a][2]benzazepine-5-carboxamide,8-cyclohexyl-N-[(dimethylamino)sulfonyl]-1a-[[4-(4-fluorophenyl)-1-piperidinyl]carbonyl]-1,1a,2,12b-tetrahydro-11-methoxy- | 95.3 | 3.98 |
| cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(4-methoxyphenyl)-1-piperidinyl]carbonyl]- | 95 | 3.91 |

| Compound | Purity | Rt (min) |
|---|---|---|
| 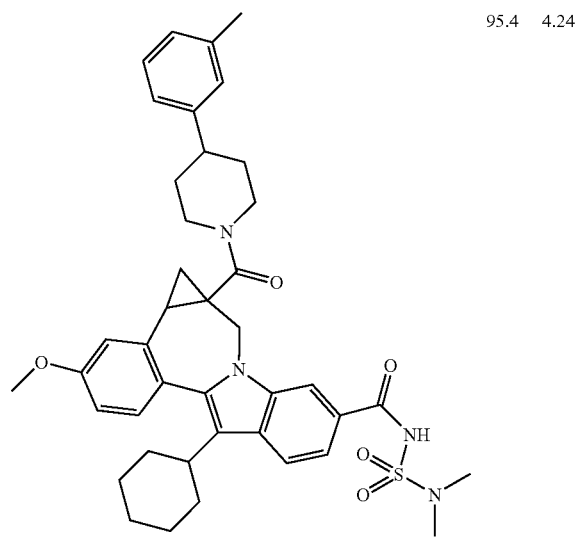 cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(4-methylphenyl)-1-piperidinyl]carbonyl]- | 95 | 4.23 |
| cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(3-methylphenyl)-1-piperidinyl]carbonyl]- | 95.4 | 4.24 |
| 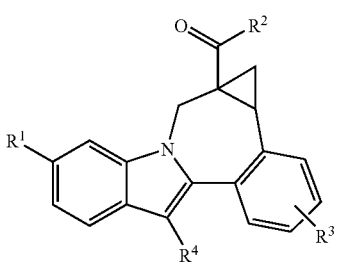 cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-[4-[(methylamino)carbonyl]phenyl]-1-piperidinyl]carbonyl]- | 96.2 | 2.99 |

What is claimed is:
1. A compound of formula I wherein:
$R^1$ is $CO_2R^5$ or $CONR^6R^7$;
$R^2$ is cycloalkoxy or bridged [2.1.1], [2.2.1], [2.2.2], [3.1.1], or [3.2.1] bicycloalkoxy, where the cycloalkyl or bridged bicycloalkyl moiety is substituted with 0-3 alkyl substituents;
or $R^2$ is $N(R^8)(R^9)$;
or $R^2$ is pyrrolidinyl, piperidinyl, piperazinyl, N-alkylpiperazinyl, N-(BOC)piperazinyl, N-benzylmethylpiperazinyl, homomorpholinyl, homopiperidinyl, morpholinyl, or thiomorpholinyl, and is substituted with 1 substituent selected from alkenyl, $R^{11}$, $(R^{11})$alkyl, $(R^{11}CO)$alkyl, pyrazinyl, pyrimidinyl, and phenyl where phenyl is substituted with 0-2 halo, alkyl, haloalkyl, cyano, hydroxy, alkoxy, haloalkoxy, CONH$_2$, CONH(alkyl), or CON(alkyl)$_2$ substituents;

or R$^2$ is homopiperazinyl or diazepanone, and is substituted with 0-2 substituents selected from the group consisting of halo, hydroxy, alkyl, hydroxyalkyl, alkoxyalkyl, amino, alkylamino, dialkylamino, aminoalkyl, alkylaminoalkyl, dialkylaminoalkyl, pyrrolidinyl, piperidinyl, piperazinyl, N-(alkyl)piperazinyl, morpholinyl, thiomorpholinyl, pyridinyl, pyrazinyl, pyrimidinyl, pyrimidinyloxy, phenyl substituted with 0-2 halo, alkyl, or alkoxy substituents, benzyl, (pyridinyl)methyl, benzyloxycarbonyl, alkylcarbonyl, alkoxycarbonyl, (R$^{11}$)alkyl, and (R$^{11}$CO)alkyl;

or R$^2$ is

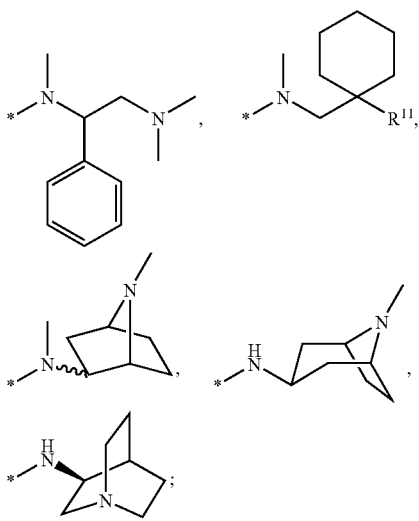

R$^3$ is hydrogen, halo, alkyl, alkenyl, hydroxy, benzyloxy, or alkoxy;

R$^4$ is C$_{5-7}$cycloalkyl;

R$^5$ is hydrogen or alkyl;

R$^6$ is hydrogen, alkyl, cycloalkyl, alkoxy, or SO$_2$R$^{10}$;

R$^7$ is hydrogen, alkyl, or cycloalkyl;

or NR$^6$R$^7$ taken together is pyrrolidinyl, piperidinyl, piperazinyl, N-(alkyl)piperazinyl, homomorpholinyl, homopiperidinyl, morpholinyl, or thiomorpholinyl;

R$^8$ is 4-piperidinyl, 4-(N-alkyl)piperidinyl, 3-(N-alkyl)pyrrolidinyl, (R$^{11}$)alkyl, (R$^{11}$CO)alkyl, (amino)cycloalkyl, (alkylamino)cycloalkyl, or (dialkylamino)cycloalkyl;

R$^9$ is hydrogen, alkyl, cycloalkyl, hydroxyalkyl, alkoxyalkyl, aminoalkyl, alkylaminoalkyl, or dialkylaminoalkyl;

R$^{10}$ is alkyl, haloalkyl, cycloalkyl, phenyl, amino, alkylamino, dialkylamino, benzylamino, or (benzyl)(alkyl)amino;

or R$^{10}$ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl; and R$^{11}$ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl;

or a pharmaceutically acceptable salt thereof.

2. A compound of claim 1 where

R$^1$ is CO$_2$R$^5$ or CONR$^6$R$^7$;

R$^2$ is cycloalkoxy or bridged [2.1.1], [2.2.1], [2.2.2], [3.1.1], or [3.2.1] bicycloalkoxy, where the cycloalkyl or bridged bicycloalkyl moiety is substituted with 0-3 alkyl substituents;

or R$^2$ is N(R$^8$)(R$^9$);

or R$^2$ is pyrrolidinyl, piperidinyl, piperazinyl, homomorpholinyl, homopiperidinyl, morpholinyl, or thiomorpholinyl, and is substituted with 1 substituent selected from R$^{11}$, (R$^{11}$)alkyl, (R$^{11}$CO)alkyl, pyrazinyl, pyrimidinyl, pyrimidinyloxy, and phenyl where phenyl is substituted with 0-2 halo, alkyl or alkoxy substituents;

or R$^2$ is homopiperazinyl or diazepanone, and is substituted with 0-2 substituents selected from the group consisting of halo, hydroxy, alkyl, hydroxyalkyl, alkoxyalkyl, amino, alkylamino, dialkylamino, aminoalkyl, alkylaminoalkyl, dialkylaminoalkyl, pyrrolidinyl, piperidinyl, piperazinyl, N-(alkyl)piperazinyl, morpholinyl, thiomorpholinyl, pyridinyl, pyrazinyl, pyrimidinyl, pyrimidinyloxy, phenyl substituted with 0-2 halo, alkyl, or alkoxy substituents, benzyl, (pyridinyl)methyl, benzyloxycarbonyl, alkylcarbonyl, alkoxycarbonyl, (R$^{11}$)alkyl, and (R$^{11}$CO)alkyl;

or R$^2$ is

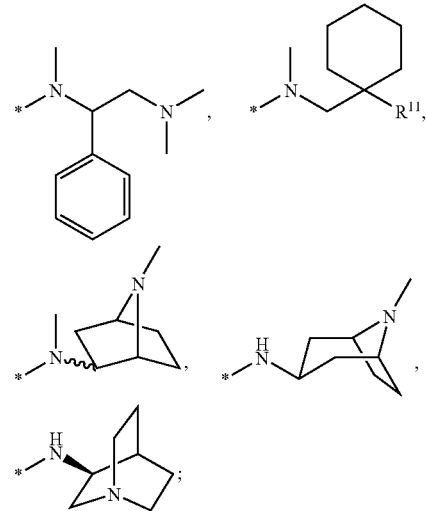

R$^3$ is hydrogen, halo, alkyl, alkenyl, hydroxy, benzyloxy, or alkoxy;

R$^4$ is C$_{5-7}$cycloalkyl;

R$^5$ is hydrogen or alkyl;

R$^6$ is hydrogen, alkyl, cycloalkyl, alkoxy, or SO$_2$R$^{10}$;

R$^7$ is hydrogen, alkyl, or cycloalkyl;

or NR$^6$R$^7$ taken together is pyrrolidinyl, piperidinyl, piperazinyl, N-(alkyl)piperazinyl, homomorpholinyl, homopiperidinyl, morpholinyl, or thiomorpholinyl;

R$^8$ is 4-piperidinyl, 4-(N-alkyl)piperidinyl, (R$^{11}$)alkyl, (R$^{11}$CO)alkyl, (amino)cycloalkyl, (alkylamino)cycloalkyl, or (dialkylamino)cycloalkyl;

R$^9$ is hydrogen, alkyl, cycloalkyl, hydroxyalkyl, alkoxyalkyl, aminoalkyl, alkylaminoalkyl, or dialkylaminoalkyl;

R$^{10}$ is alkyl, haloalkyl, cycloalkyl, phenyl, amino, alkylamino, dialkylamino, benzylamino, or (benzyl)(alkyl)amino;

or R¹⁰ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl; and R¹¹ is azetidinyl, pyrrolidinyl, piperidinyl, piperazinyl, homomorpholinyl, homopiperidinyl, morpholinyl, or thiomorpholinyl, and is substituted with 0-2 substituents selected from halo and alkyl;

or a pharmaceutically acceptable salt thereof.

3. A compound of claim 1 where $R^1$ is carboxy.

4. A compound of claim 1 where $R^1$ is CONR⁶R⁷, R⁶ is SO₂R¹⁰, and R⁷ is hydrogen.

5. A compound of claim 1 where $R^2$ is NR⁸R⁹.

6. A compound of claim 1 where $R^2$ is pyrrolidinyl, piperidinyl, piperazinyl, N-alkylpiperazinyl, N-(BOC)piperazinyl, N-benzylmethylpiperazinyl, homomorpholinyl, homopiperidinyl, morpholinyl, or thiomorpholinyl, and is substituted with 1 substituent selected from alkenyl, R¹¹, (R¹¹)alkyl, (R¹¹CO)alkyl, pyrazinyl, pyrimidinyl, and phenyl where phenyl is substituted with 0-2 halo, alkyl or alkoxy substituents.

7. A compound of claim 1 where $R^3$ is hydrogen.

8. A compound of claim 1 where $R^3$ is halo, alkyl, or alkoxy.

9. A compound of claim 1 where $R^4$ is cyclohexyl.

10. A compound selected from the group consisting of

-continued

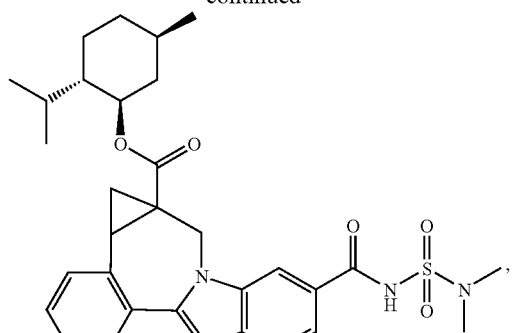

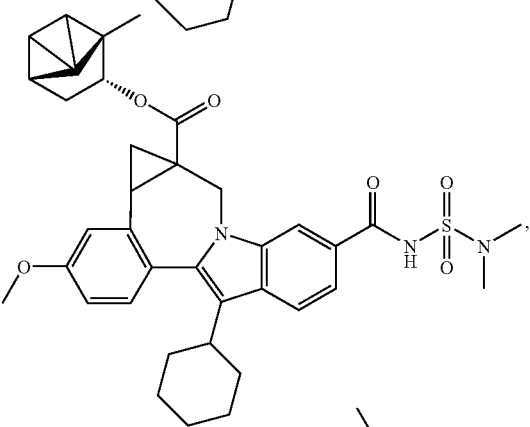

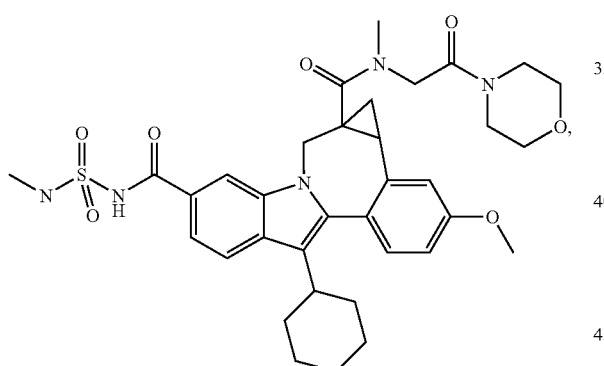

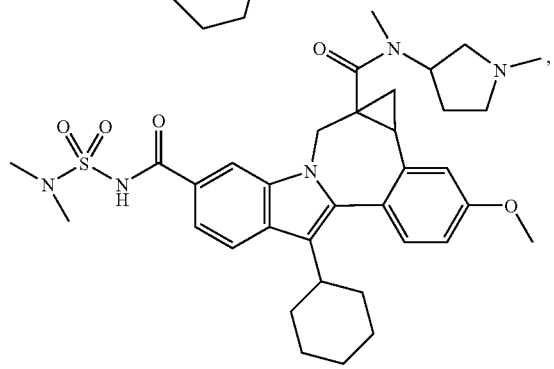

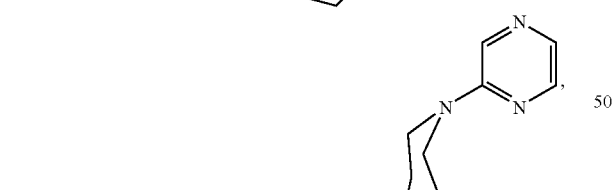

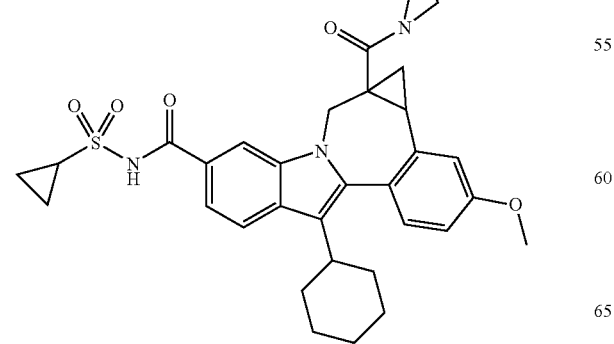

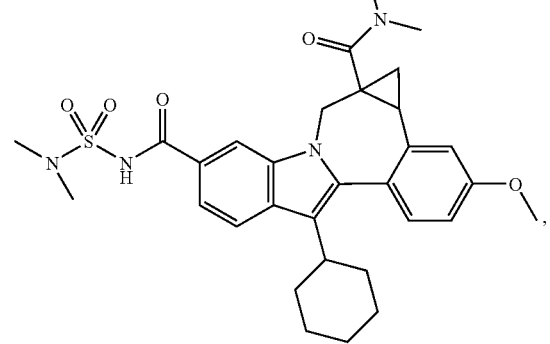

137
-continued
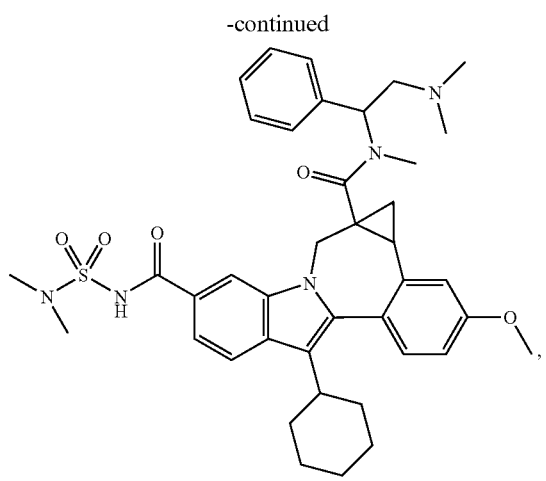
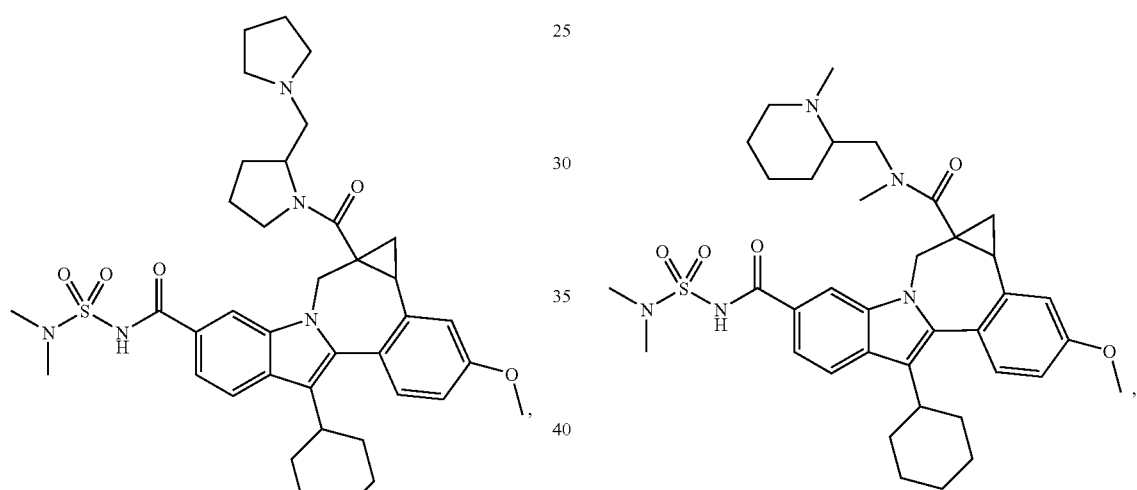
138
-continued
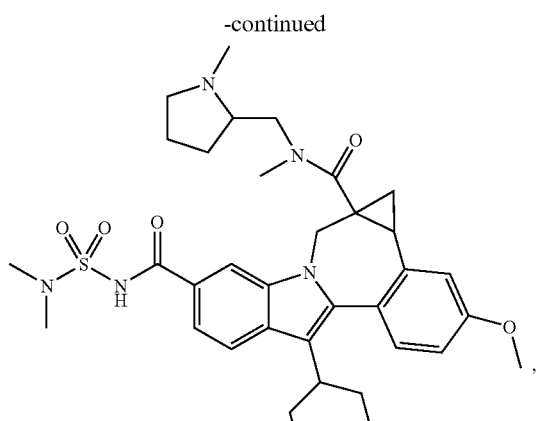
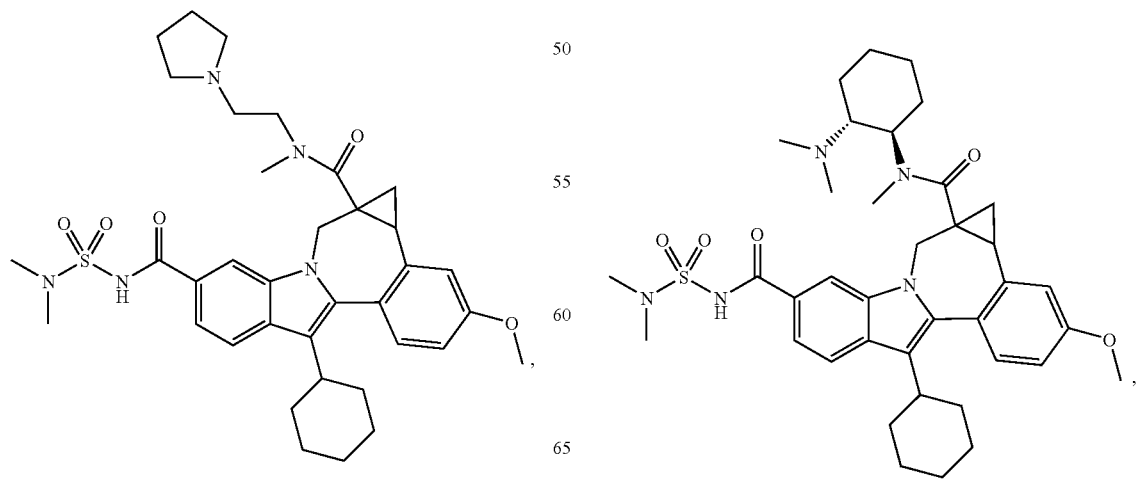

-continued
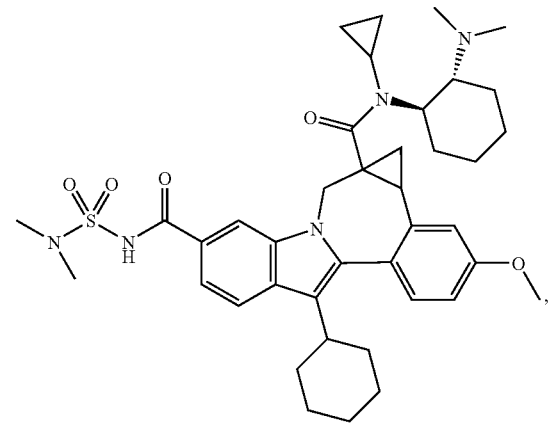
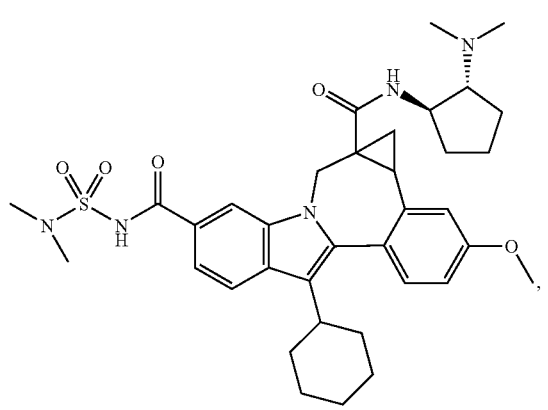
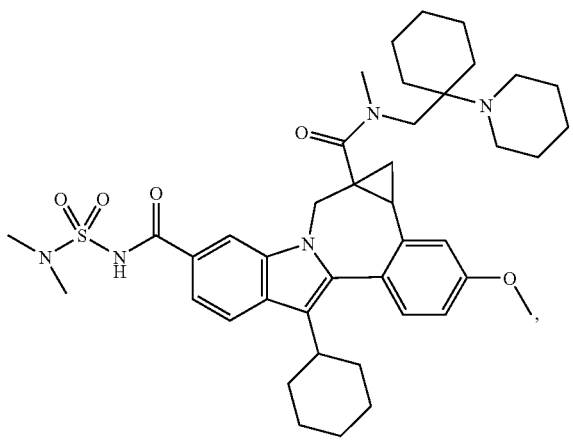
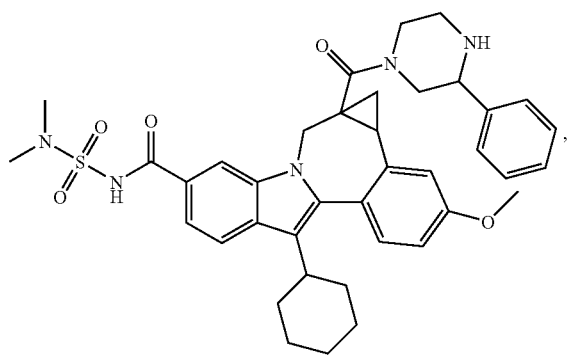
-continued
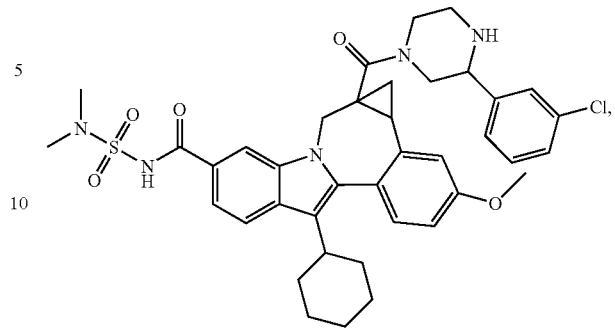
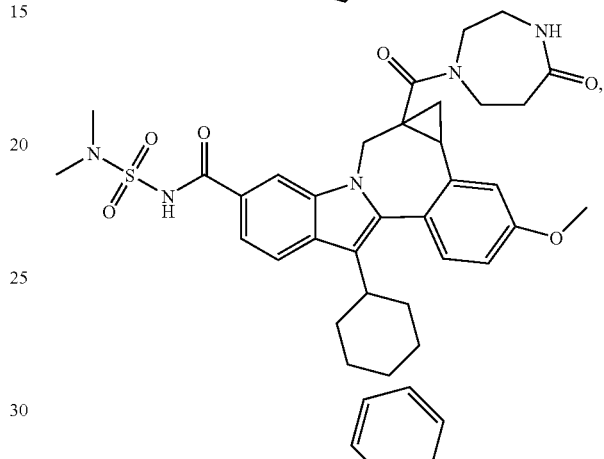
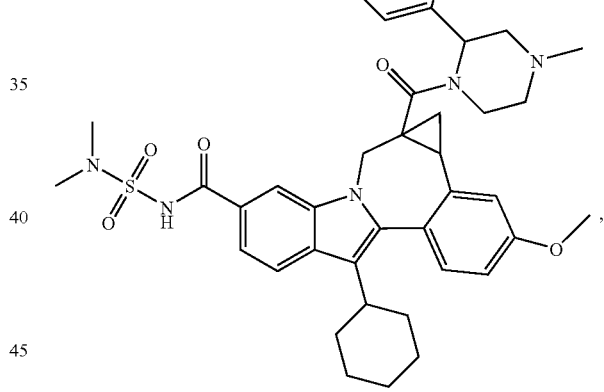
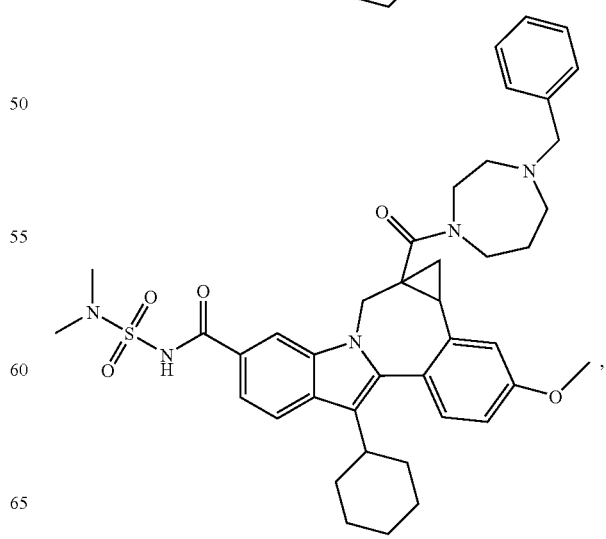

-continued
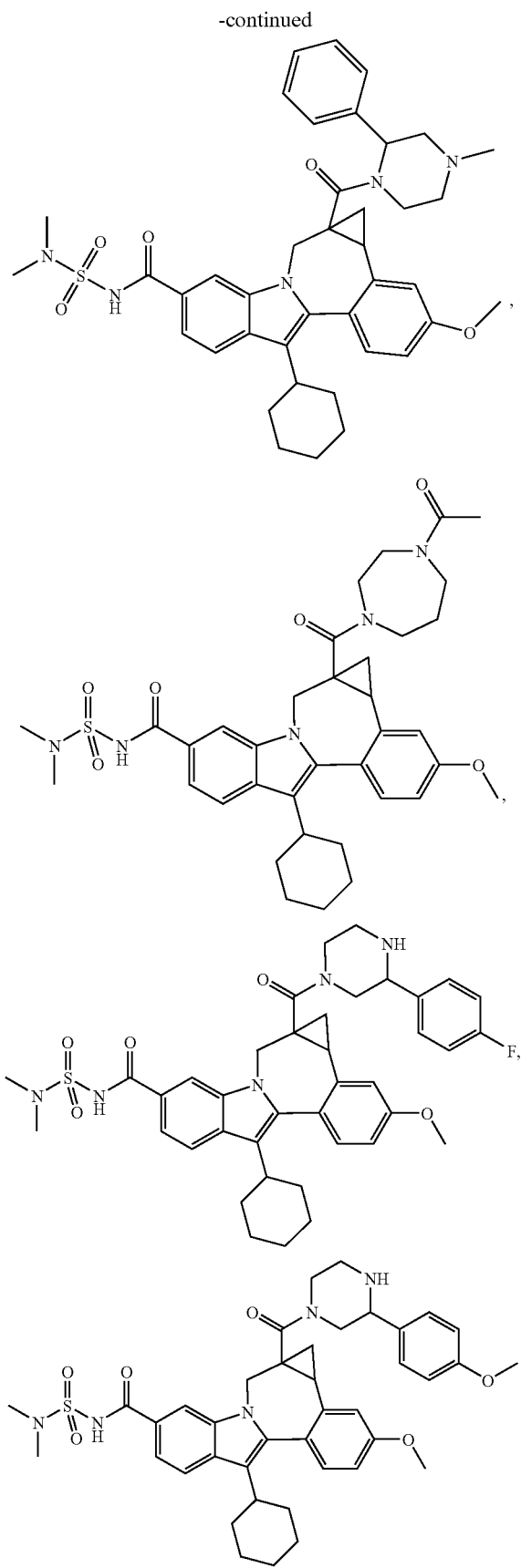
-continued
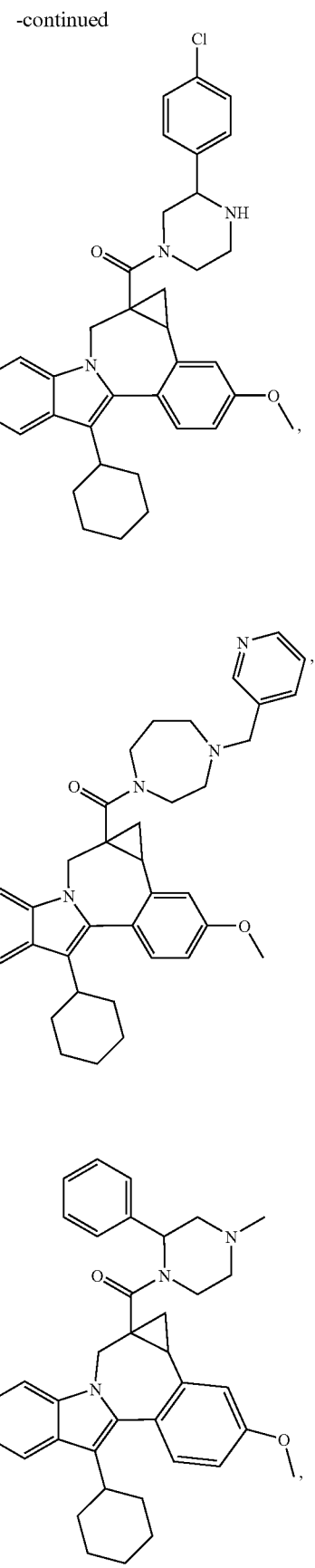

143
-continued
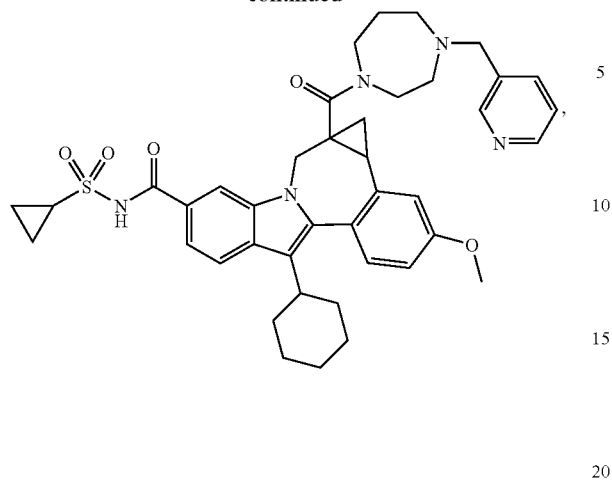
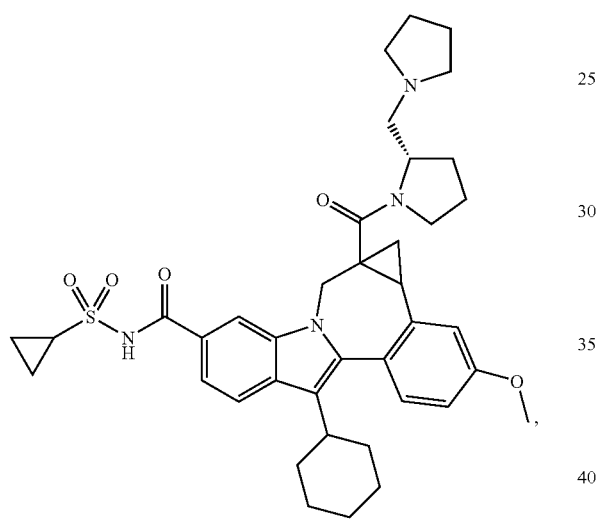
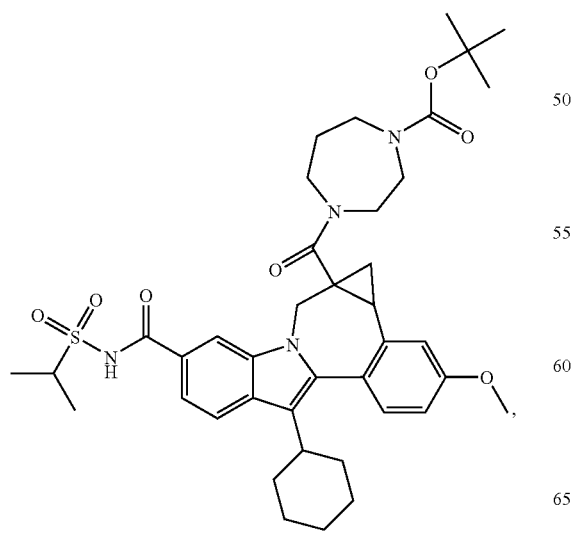
144
-continued
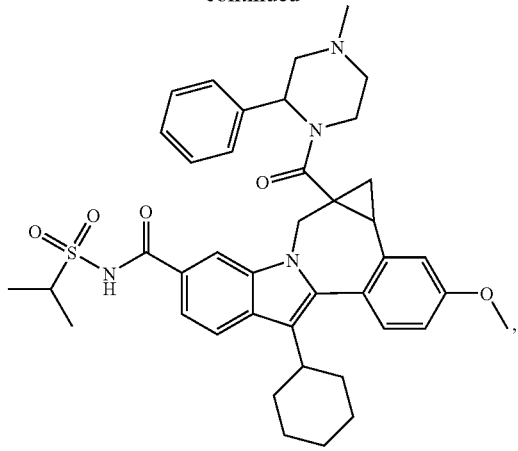
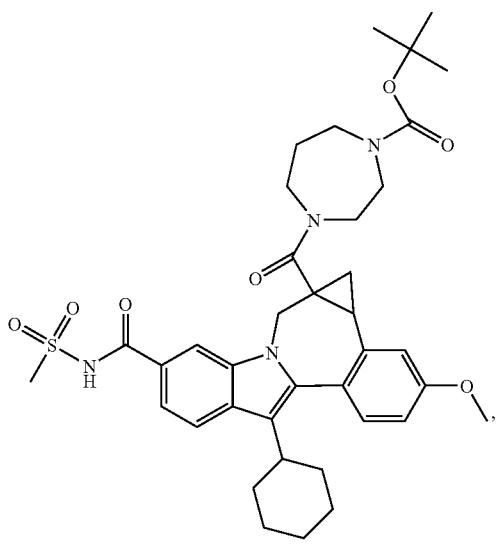
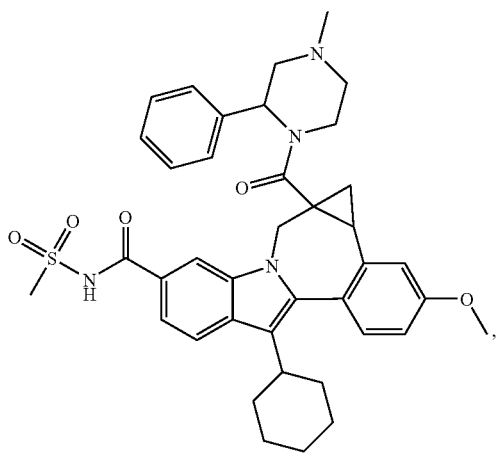

145
-continued
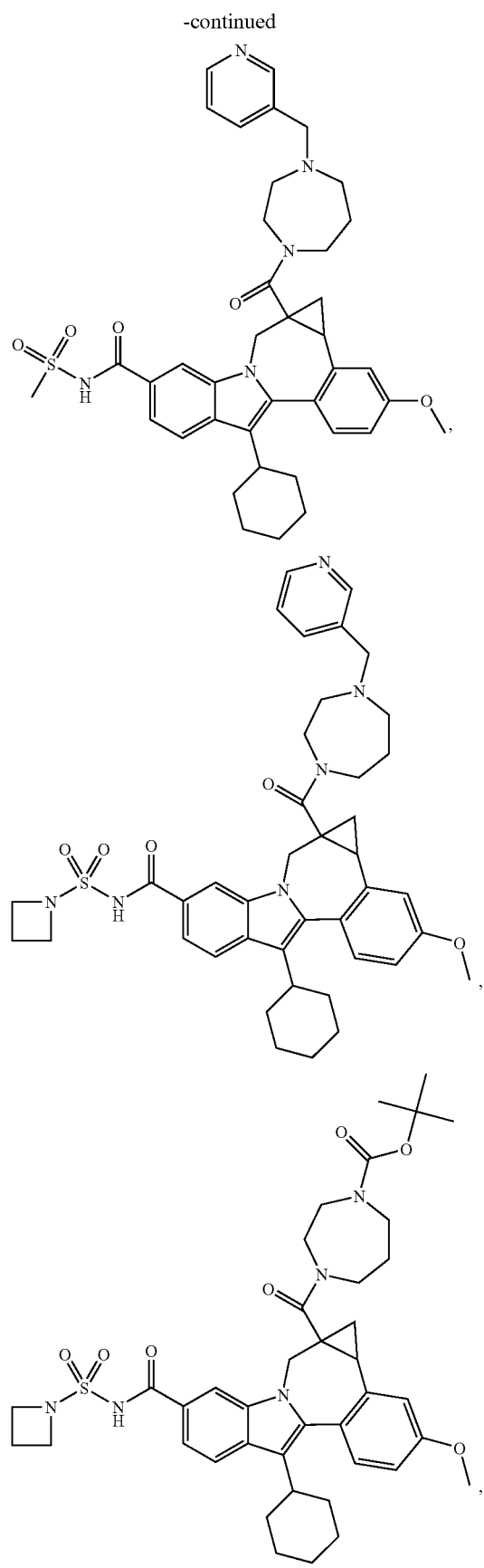
146
-continued
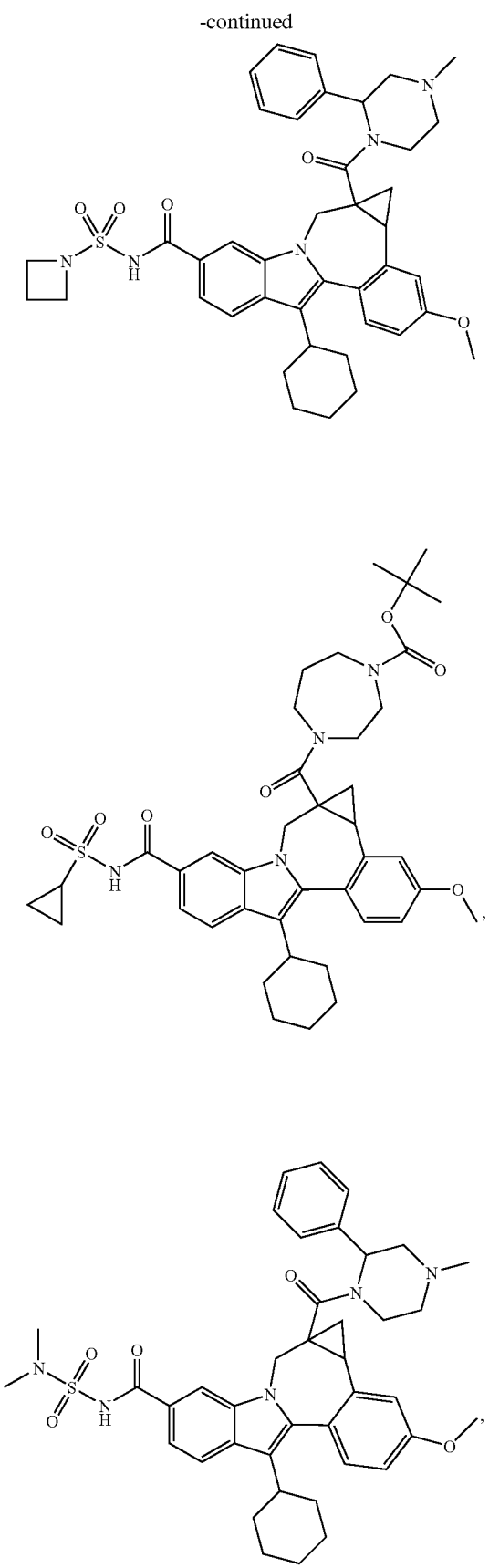

-continued
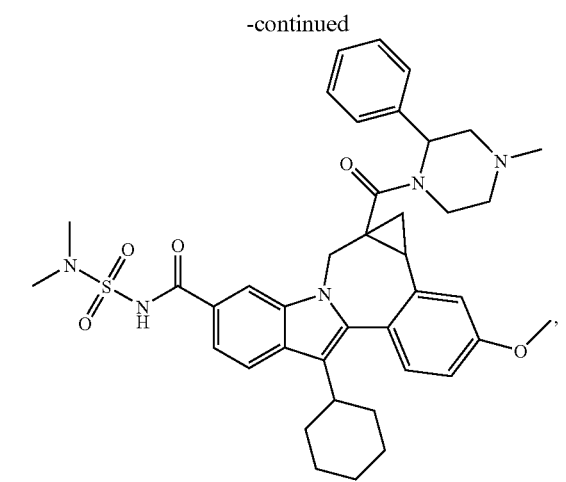
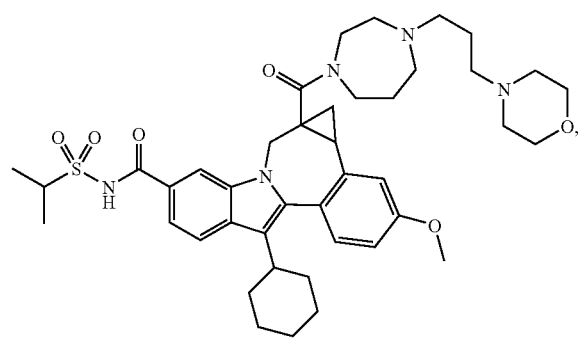
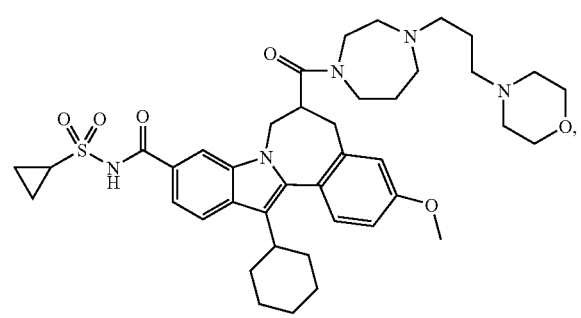
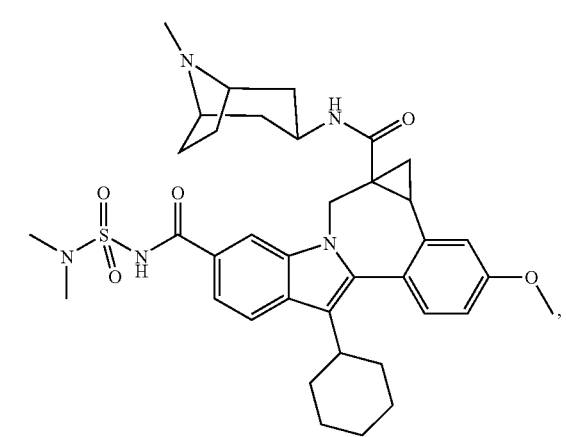
-continued
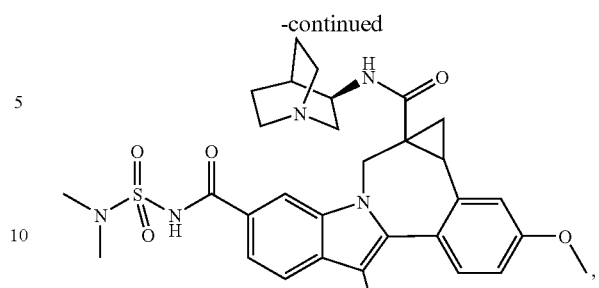
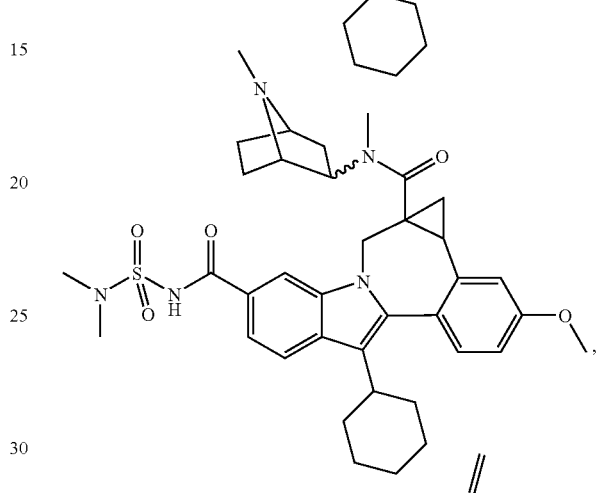
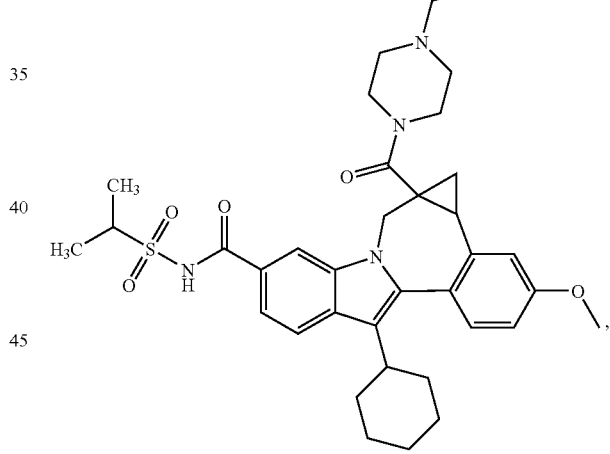
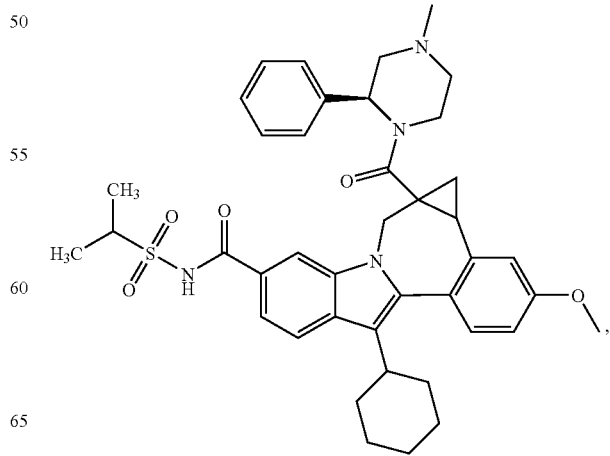

149
-continued
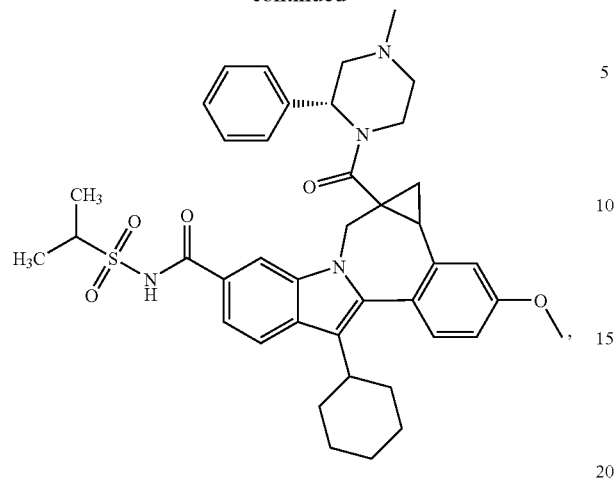
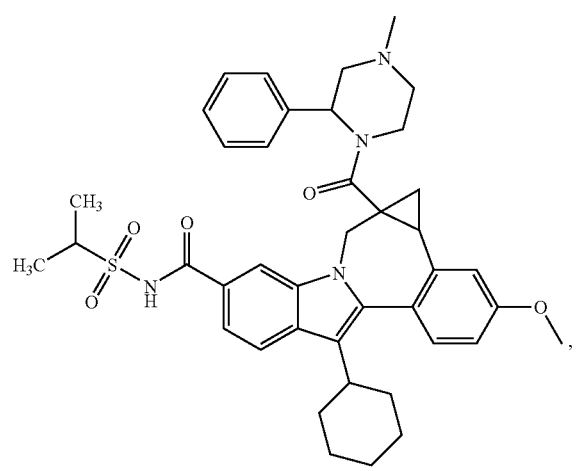
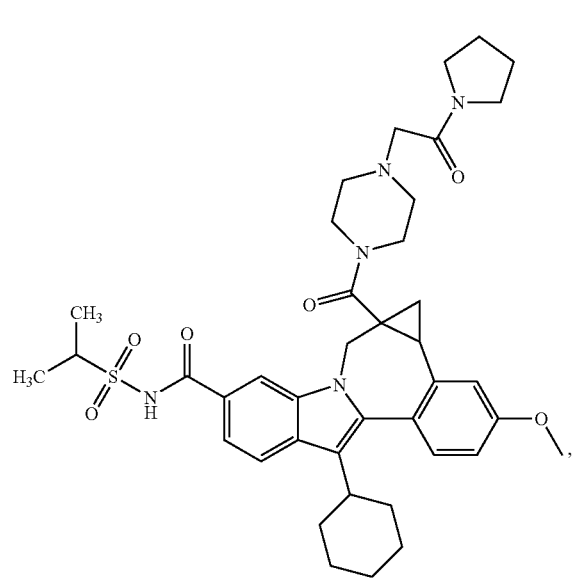
150
-continued
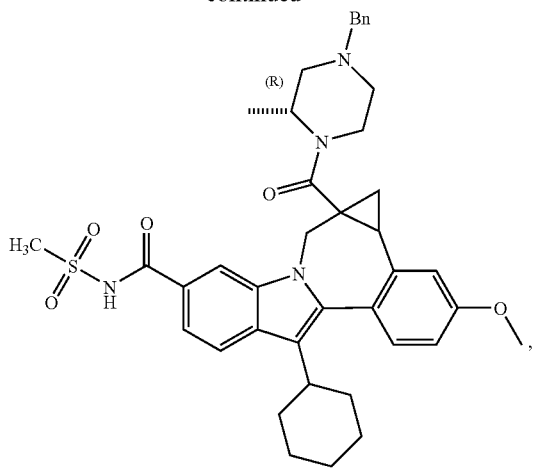
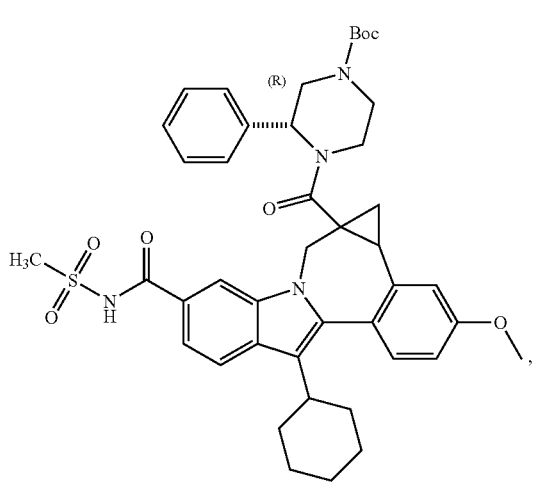
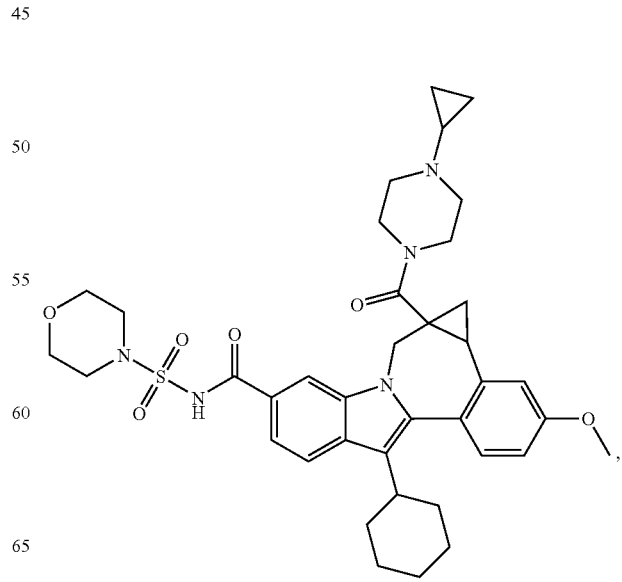

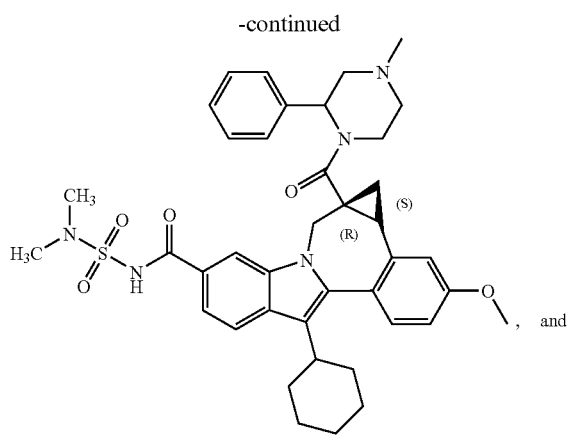
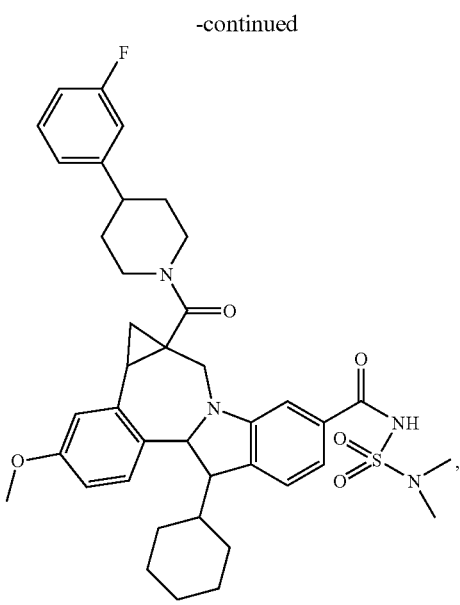
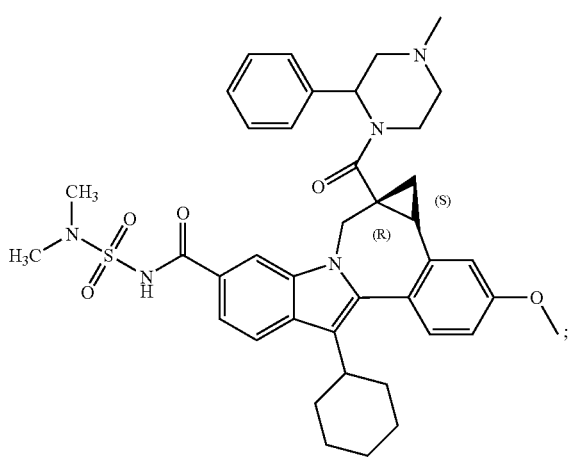
or a pharmaceutically acceptable salt thereof.
11. A compound of claim 1 selected from the group consisting of
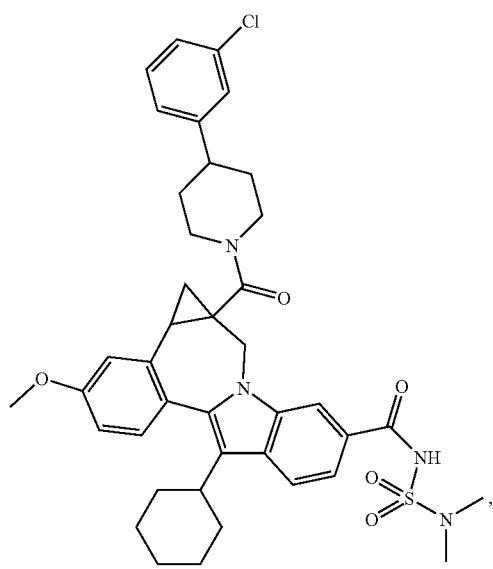
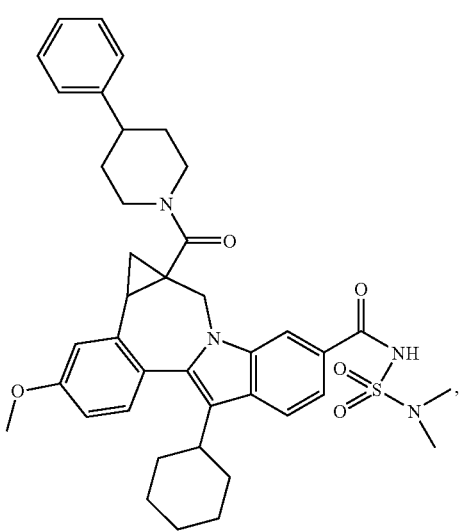

153
-continued
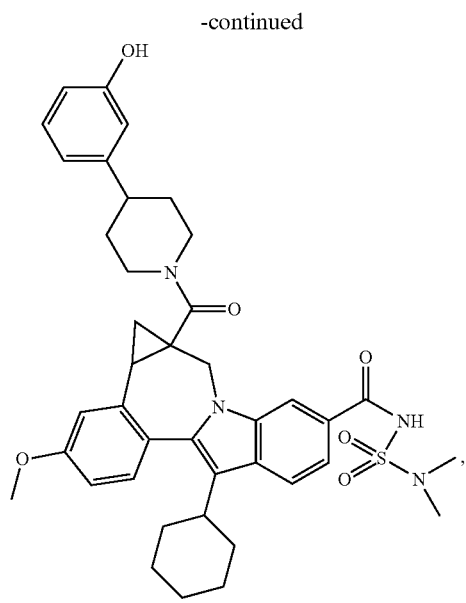
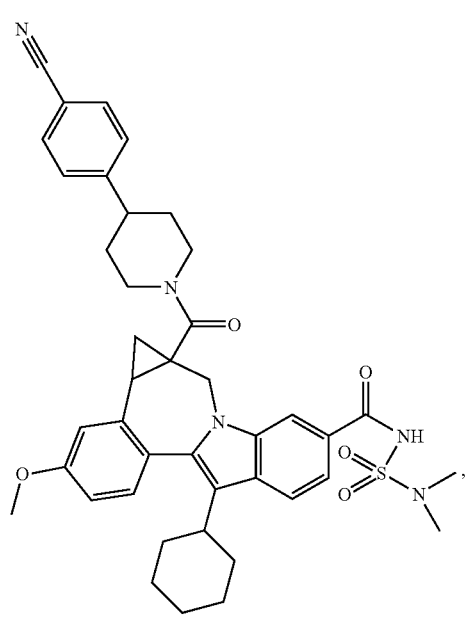
154
-continued
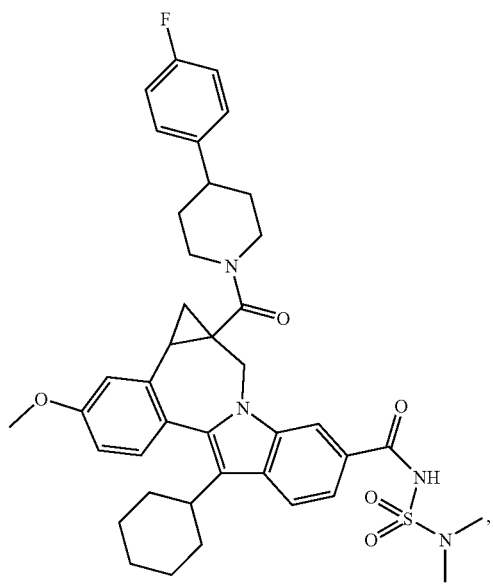
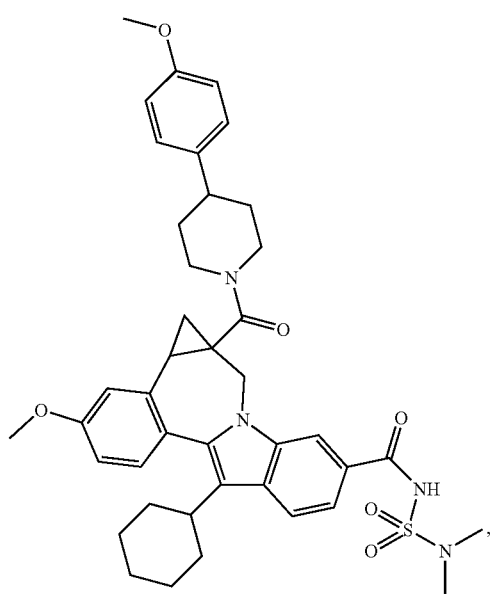

-continued
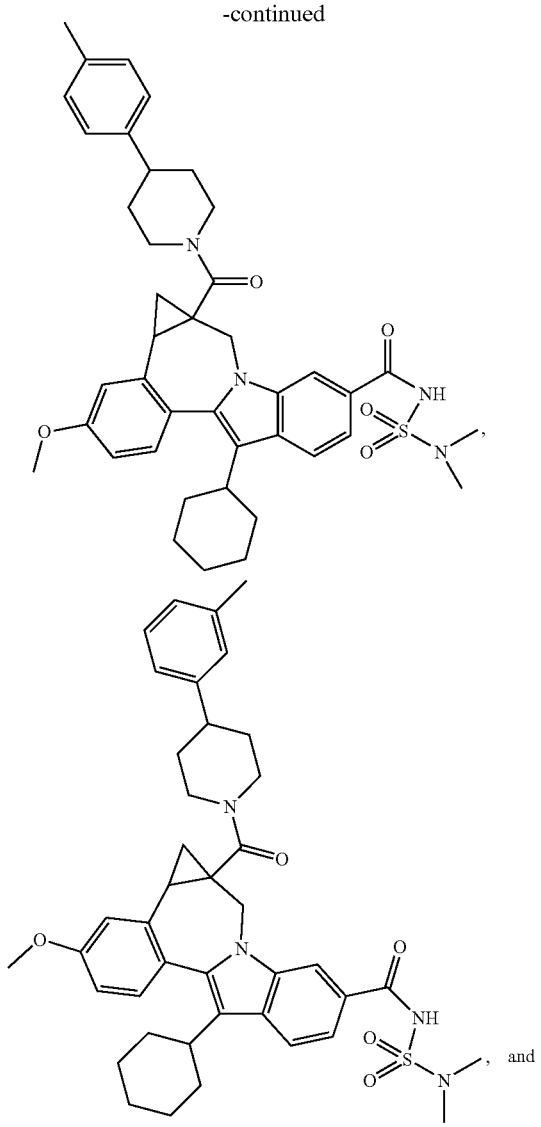
, and
-continued
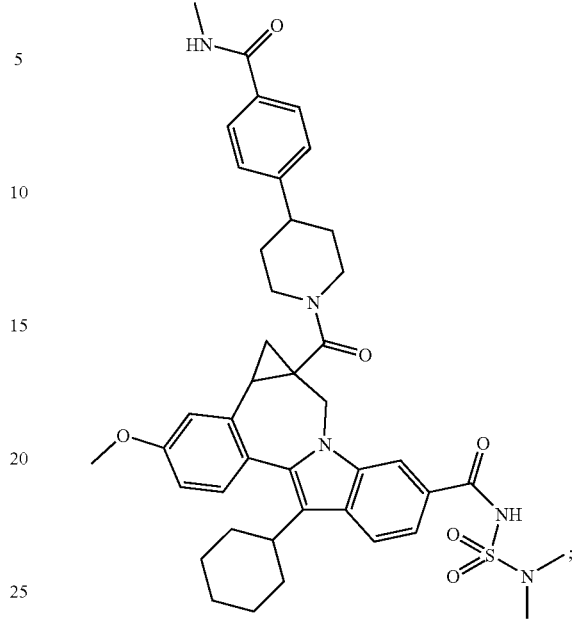
or a pharmaceutically acceptable salt thereof.
12. A composition comprising a compound of claim 1, or a pharmaceutically acceptable salt thereof, and a pharmaceutically acceptable carrier.
13. A method of treating hepatitis C infection comprising administering a therapeutically effective amount of a compound of claim 1 to a patient.
* * * * *

UNITED STATES PATENT AND TRADEMARK OFFICE
CERTIFICATE OF CORRECTION

PATENT NO.       : 7,538,102 B2
APPLICATION NO.  : 12/046030
DATED            : May 26, 2009
INVENTOR(S)      : Kap-Sun Yeung et al.

Page 1 of 1

It is certified that error appears in the above-identified patent and that said Letters Patent is hereby corrected as shown below:

In the Claims:

Claim 2:

Column 134, line 12, before "and phenyl", delete "pyrimidinyloxy,".

Claim 10:

Column 135, lines 33 to 46, change

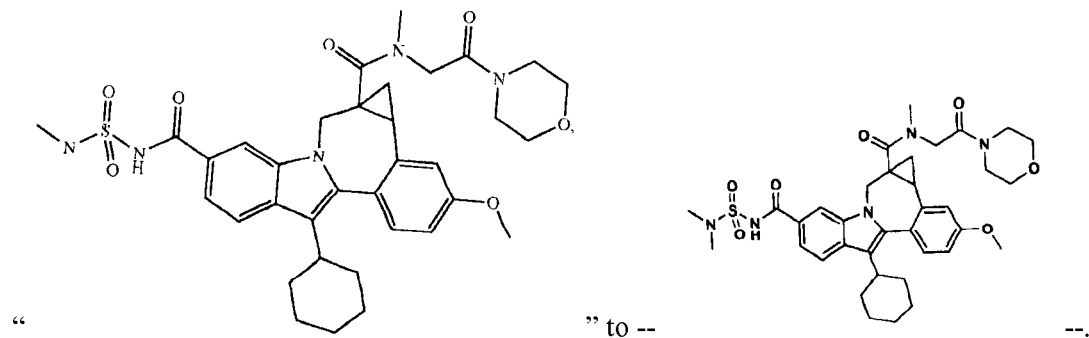

" to -- --.

Column 136, lines 3 to 19, change

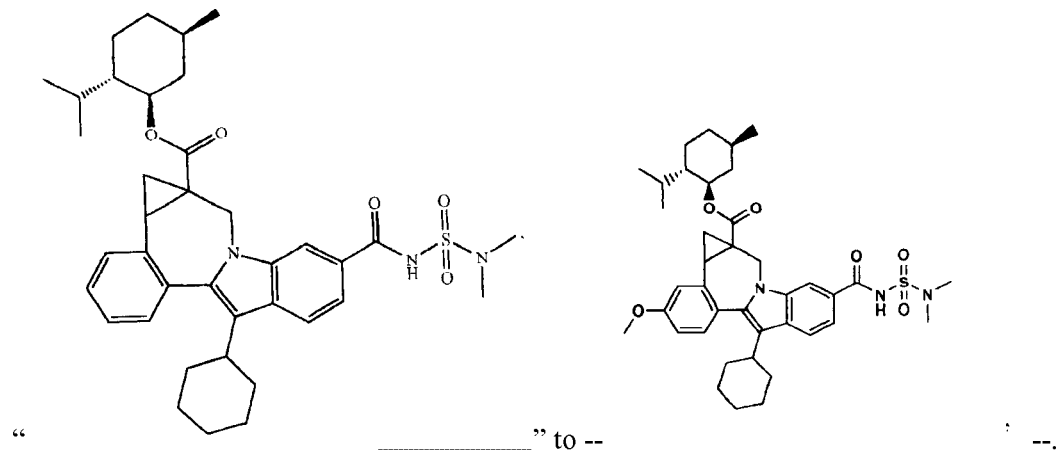

" to -- --.

Signed and Sealed this
Eighth Day of November, 2011

David J. Kappos
*Director of the United States Patent and Trademark Office*